(12) United States Patent
Johnson et al.

(10) Patent No.: US 8,163,758 B2
(45) Date of Patent: Apr. 24, 2012

(54) PHENYL SUBSTITUTED PYRAZINOYLGUANIDINE SODIUM CHANNEL BLOCKERS POSSESSING BETA AGONIST ACTIVITY

(75) Inventors: Michael Ross Johnson, Chapel Hill, NC (US); Andrew J. Hirsh, Durham, NC (US); Richard C. Boucher, Chapel Hill, NC (US); Jianzhong Zhang, Rensselaer, NY (US)

(73) Assignee: Parion Sciences, Inc., Durham, NC (US)

( * ) Notice: Subject to any disclaimer, the term of this patent is extended or adjusted under 35 U.S.C. 154(b) by 313 days.

(21) Appl. No.: 12/304,006

(22) PCT Filed: Jun. 11, 2007

(86) PCT No.: PCT/US2007/070861
§ 371 (c)(1),
(2), (4) Date: Dec. 9, 2008

(87) PCT Pub. No.: WO2007/146869
PCT Pub. Date: Dec. 21, 2007

(65) Prior Publication Data
US 2011/0008268 A1   Jan. 13, 2011

Related U.S. Application Data

(60) Provisional application No. 60/812,077, filed on Jun. 9, 2006.

(51) Int. Cl.
A61K 31/4965 (2006.01)
(52) U.S. Cl. .................. 514/255.06; 544/407
(58) Field of Classification Search ............ 514/255.06; 544/407
See application file for complete search history.

(56) References Cited

U.S. PATENT DOCUMENTS

| | | | |
|---|---|---|---|
| 6,858,614 B2 | 2/2005 | Johnson | |
| 6,858,615 B2 | 2/2005 | Johnson | |
| 6,903,105 B2 | 6/2005 | Johnson | |
| 6,995,160 B2 | 2/2006 | Johnson | |
| 7,026,325 B2 | 4/2006 | Johnson | |
| 7,030,117 B2 | 4/2006 | Johnson | |
| 7,064,129 B2 | 6/2006 | Johnson et al. | |
| 7,186,833 B2 | 3/2007 | Johnson | |
| 7,189,719 B2 | 3/2007 | Johnson | |
| 7,192,958 B2 | 3/2007 | Johnson | |
| 7,192,959 B2 | 3/2007 | Johnson | |
| 7,192,960 B2 | 3/2007 | Johnson | |
| 7,241,766 B2 | 7/2007 | Johnson | |
| 7,247,636 B2 | 7/2007 | Johnson | |
| 7,247,637 B2 | 7/2007 | Johnson et al. | |
| 7,317,013 B2 | 1/2008 | Johnson | |
| 7,332,496 B2 | 2/2008 | Johnson | |
| 7,345,044 B2 | 3/2008 | Johnson | |
| 7,368,447 B2 | 5/2008 | Johnson et al. | |
| 7,368,450 B2 | 5/2008 | Johnson | |
| 7,368,451 B2 | 5/2008 | Johnson et al. | |
| 7,375,107 B2 | 5/2008 | Johnson | |
| 7,388,013 B2 | 6/2008 | Johnson et al. | |
| 7,399,766 B2 | 7/2008 | Johnson | |
| 7,410,968 B2 | 8/2008 | Johnson et al. | |
| 2005/0080093 A1 | 4/2005 | Johnson et al. | |
| 2005/0090505 A1 | 4/2005 | Johnson et al. | |
| 2006/0052395 A1 | 3/2006 | Johnson et al. | |
| 2006/0142306 A1 | 6/2006 | Johnson | |
| 2006/0142581 A1 | 6/2006 | Johnson | |
| 2007/0032509 A1 | 2/2007 | Johnson et al. | |
| 2007/0265280 A1 | 11/2007 | Johnson | |
| 2008/0076782 A1 | 3/2008 | Johnson | |
| 2008/0090841 A1 | 4/2008 | Johnson et al. | |
| 2008/0096896 A1 | 4/2008 | Johnson | |
| 2008/0103148 A1 | 5/2008 | Johnson | |
| 2008/0167466 A1 | 7/2008 | Johnson et al. | |
| 2008/0171879 A1 | 7/2008 | Johnson | |
| 2008/0171880 A1 | 7/2008 | Johnson et al. | |
| 2008/0176863 A1 | 7/2008 | Johnson et al. | |

(Continued)

FOREIGN PATENT DOCUMENTS

WO   WO 2005/018644 A1   3/2005

(Continued)

OTHER PUBLICATIONS

U.S. Appl. No. 10/920,527, filed Aug. 18, 2004, Hopkins.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.

(Continued)

*Primary Examiner* — James O Wilson
*Assistant Examiner* — Douglas M Willis
(74) *Attorney, Agent, or Firm* — Oblon, Spivak, McClelland, Maier & Neustadt, L.L.P.

(57) ABSTRACT

Provided is class of sodium channel blockers. One example of such a compound is shown by the following formula:

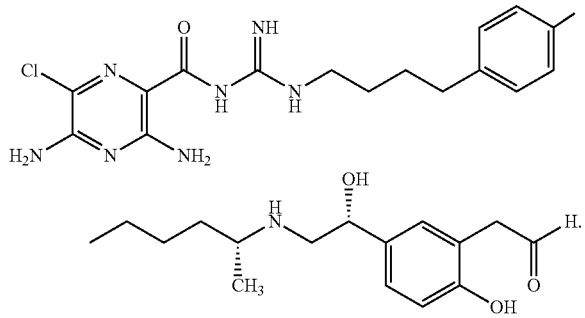

The compounds are useful for promoting hydration of mucosal surfaces and treating a variety of disease conditions.

3 Claims, 4 Drawing Sheets

U.S. PATENT DOCUMENTS

| | | |
|---|---|---|
| 2008/0177072 A1 | 7/2008 | Johnson |
| 2008/0200476 A1 | 8/2008 | Johnson |
| 2008/0249109 A1 | 10/2008 | Johnson et al. |
| 2008/0293740 A1 | 11/2008 | Johnson et al. |

FOREIGN PATENT DOCUMENTS

| | | |
|---|---|---|
| WO | WO 2008/030217 A2 | 3/2008 |
| WO | WO 2008/030217 A3 | 3/2008 |

OTHER PUBLICATIONS

U.S. Appl. No. 60/845,171, filed Sep. 18, 2006, Johnson, et al.
U.S. Appl. No. 11/696,003, filed Apr. 3, 2007, Johnson.
U.S. Appl. No. 11/573,413, filed Feb. 8, 2007, Johnson.
U.S. Appl. No. 11/573,421, filed Feb. 8, 2007, Johnson.
U.S. Appl. No. 60/909,818, filed Apr. 3, 2007, Johnson, et al.
U.S. Appl. No. 11/852,003, filed Sep. 7, 2007, Johnson. et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson,et al.
U.S. Appl. No. 11/835,902, filed Aug. 8, 2007, Johnson. et al.
U.S. Appl. No. 61/030,313, filed Feb. 21, 2008, Johnson.
U.S. Appl. No. 61/031,466, filed Feb. 26, 2008, Johnson.
U.S. Appl. No. 12/049,993, filed Mar. 17, 2008, Johnson.
U.S. Appl. No. 12/171,814, filed Jul. 11, 2008, Johnson. et al.
U.S. Appl. No. 12/171,867, filed Jul. 11, 2008, Johnson. et al.
U.S. Appl. No. 12/171,897, filed Jul. 11, 2008, Johnson. et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 12/249,175, filed Oct. 10, 2008, Boucher, et al.
U.S. Appl. No. 12/304,042, filed Dec. 9, 2008, Johnson.
U.S. Appl. No. 12/304,040, filed Dec. 9, 2008, Johnson.
U.S. Appl. No. 12/939,579, filed Nov. 4, 2010, Johnson, et al.
U.S. Appl. No. 12/393,252, filed Feb. 26, 2009, Johnson.
Office Action issued Jun. 24, 2011 in Europe Application No. 07 784 388.6.
U.S. Appl. No. 60/909,802, filed Apr. 3, 2007, Johnson, et al.
U.S. Appl. No. 12/501,654, filed Jul. 13, 2009, Boucher, et al.
U.S. Appl. No. 12/876,615, filed Sep. 7, 2010, Johnson, et al.
Australian Examination Report issued Nov. 18, 2011, in Patent Application No. 2007257781.
Strader et al. "Structural basis of β-adrenergic receptor function", FASEB, vol. 3, pp. 1825-1832, (1989).

Figure 4: Tautomeric Forms of Formula I Compounds
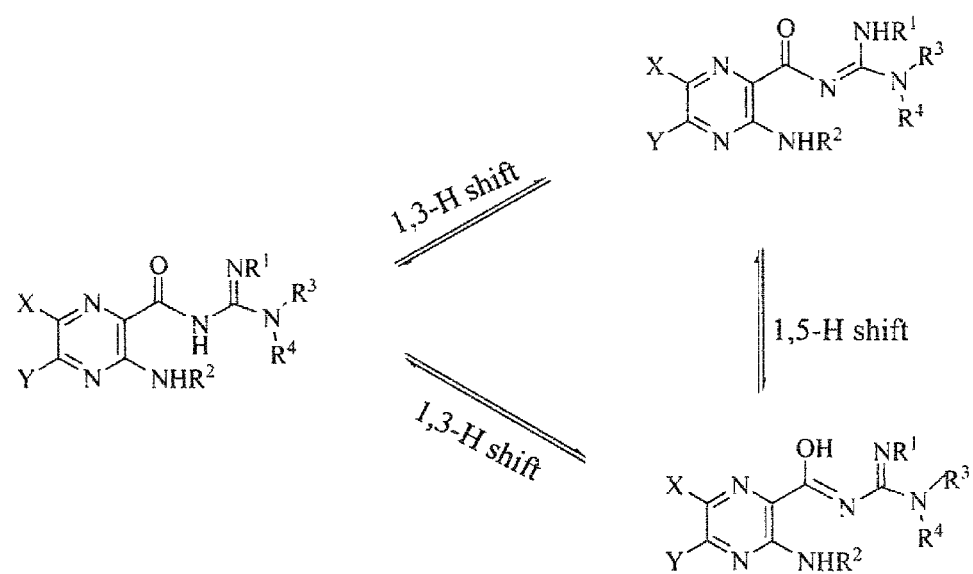

PHENYL SUBSTITUTED PYRAZINOYLGUANIDINE SODIUM CHANNEL BLOCKERS POSSESSING BETA AGONIST ACTIVITY

CONTINUING APPLICATION DATA

This application is a National Stage of International application No. PCT/US07/70861, filed on Jun. 11, 2007, incorporated herein by reference; which application claims priority to U.S. provisional application Ser. No. 60/812,077, filed 9 Jun. 2006.

BACKGROUND OF THE INVENTION

1. Field of the Invention

The present invention relates to sodium channel blockers possessing beta-adrenergic receptor agonist activity. The present invention also includes a variety of methods of treatment using these inventive sodium channel blockers/beta-adrenergic receptor agonists.

2. Description of the Background

The mucosal surfaces at the interface between the environment and the body have evolved a number of "innate defenses", i.e., protective mechanisms. A principal form of such an innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion) and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption and simultaneously activating beta-adrenergic receptors thereby causing liquid secretion. The epithelial protein that mediates the rate-limiting step of $Na^+$ and liquid absorption is the epithelial $Na^+$ channel (ENaC). ENaC and beta-adrenergic receptors are positioned on the apical surface of the epithelium, i.e. the mucosal surface-external environment interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers containing beta-adrenergic receptor agonist activity designed to exhibit the increased potency, reduced mucosal absorption, and slow dissociation ("unbinding" or detachment) from ENaC and the beta-adrenergic receptor required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health subjects effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules are organized into a well defined "mucus layer" which normally traps inhaled bacteria and are transported out of the lung via the actions of cilia which beat in a watery, low viscosity solution termed the "periciliary liquid" (PCL). In the disease state, there is an imbalance in the quantities of mucus and ASL on airway surfaces. This imbalance results in a relative reduction in ASL which leads to mucus concentration, a reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, inhaled β-agonists, steroids, anti-cholinergic agents, and oral theophyllines and phosphodiesterase inhibitors are all in current use. However, none of these drugs alone effectively treat the fundamental problem of the failure to clear mucus from the lung. Similarly, in cystic fibrosis, the same spectrum of pharmacologic agents are used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics (e. "TOBI") designed to augment the lungs' own killing mechanisms to rid the adherent mucus plaques of bacteria. A general principle of the body is that if the initiating lesion is not treated, in this case mucus retention/obstruction, bacterial infections become chronic and increasingly refractory to antimicrobial therapy. Thus, a major unmet therapeutic need for both CB and CF lung diseases is an effective means of re-hydrating airway mucus restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However; these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diurectics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete Cl– (and liquid) in the proximal small intestine, combined with increased $Na^+$ (and liquid) absorption in the terminal ileum leads to the distal intestinal obstruction syndrome (DIOS) in older patients, excessive $Na^+$ (and volume) absorption in the descending colon produces chronic constipation and diverticulitis.

SUMMARY OF THE INVENTION

It is an object of the present invention to provide compounds that have both sodium channel blocking activity and beta-adrenergic receptor agonist activity in the same molecule.

It is an object of the present invention to provide compounds that are more potent and/or absorbed less rapidly from mucosal surfaces, and/or are less reversible as compared to known compounds.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) when absorbed from musosal surfaces after administration to the mucosal surfaces, are converted in vivo into metabolic derivatives thereof which have reduced efficacy in blocking sodium channels and beta-adrenergic receptor agonist activity as compared to the administered parent compound.

It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide methods of treatment that take advantage of the pharmacological properties of the compounds described above.

In particular, it is an object of the present invention to provide methods of treatment which rely on rehydration of mucosal surfaces.

Any of the compounds described herein can be a pharmaceutically acceptable salt thereof, and wherein the above compounds are inclusive of all racemates, enantiomers, diastereomers, tautomers, polymorphs and pseudopolymorphs thereof. Polymorphs are different physical forms—different crystal forms that have differing melting ranges, show differing differential scanning calorimetry (DSC) tracings and exhibit different X-Ray powder diffraction (XRPD) spectra. Pseudopolymorphs are different solvated physical forms—different crystal forms that have differing melting ranges as solvates, show differing differential scanning calorimetry (DSC) tracings as solvates and exhibit different X-Ray powder diffraction (XRPD) spectra as solvates.

The present invention also provides pharmaceutical compositions which contain a compound described above.

The present invention also provides a method of promoting hydration of mucosal surfaces, comprising:
administering an effective amount of a compound represented by formula (I) to a mucosal surface of a subject.

The present invention also provides a method of restoring mucosal defense, comprising:
topically administering an effective amount of compound represented by formula (I) to a mucosal surface of a subject in need thereof.

The present invention also provides a method of blocking ENaC and exerting beta-adrenergic receptor agonism comprising:
contacting sodium channels and at the same time activating beta-adrenergic receptors (beta agonists) with an effective amount of a compound represented by formula (I).

The objects of the resent invention may be accomplished with a class of pyrazinoylguanidine compounds representing a compound represented by formula (I):

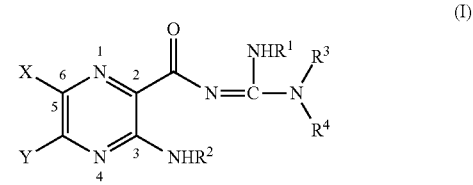

wherein
X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or —N($R^2$)$_2$;

$R^1$ is hydrogen or lower alkyl;

each $R^2$ is, independently, —$R^7$, —(CH$_2$)$_m$—O$R^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

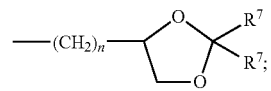

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

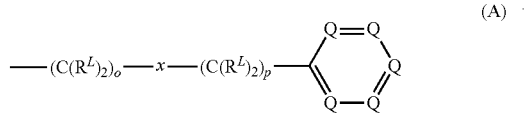
(A)

wherein each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

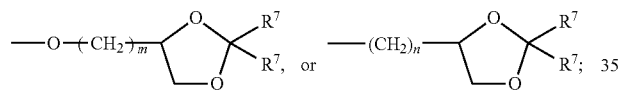

each o is, independently, an integer from 0 to 10;

each p is an integer from 0 to 10;

with the proviso that the sum of o and p in each contiguous chain from 1 to 10;

each x is, independently, O, $NR^{10}$, $C(=O)$, CHOH, $C(=N-R^{10})$, $CHNR^7R^{10}$, or represents a single bond;

wherein each $R^5$ is, independently,

Link $-(CH_2)_n-CR^{11}R^{11}$-CAP, Link $-(CH_2)_n(CHOR^8)(CHOR^8)_n-CR^{11}R^{11}$-CAP, Link $-(CH_2CH_2O)_m-CH_2-CR^{11}R^{11}$-CAP, Link $-(CH_2CH_2O)_m-CH_2CH_2-CR^{11}R^{11}$-CAP, Link $-(CH_2)_n-(Z)_g-CR^{11}R^{11}$-CAP, Link $-(CH_2)_n(Z)_g-(CH_2)_m-CR^{11}R^{11}$-CAP, Link $-(CH_2)_n-NR^{13}-CH_2(CHOR^8)(CHOR^8)_n-CR^{11}R^{11}$-CAP, Link $-(CH_2)_n-(CHOR^8)_mCH_2-NR^{13}-(Z)_g-CR^{11}R^{11}$-CAP, Link $-(CH_2)_nNR^{13}-(CH_2)_m(CHOR^8)_nCH_2NR^{13}-(Z)_g-CR^{11}R^{11}$-CAP, Link $-(CH_2)_m-(Z)_g-(CH_2)_m-CR^{11}R^{11}$-CAP, Link $NH-C(=O)-NH-(CH_2)_m-CR^{11}R^{11}$-CAP, Link $-(CH_2)_m-C(=O)NR^{13}-(CH_2)_m-CR^{11}R^{11}$-CAP, Link $-(CH_2)_n-(Z)_g-(CH_2)_m-(Z)_g-CR^{11}R^{11}$-CAP, Link $-Z_g-(CH_2)_m-$Het-$(CH_2)_m-CR^{11}R^{11}$-CAP, wherein Link is, independently, $-O-$, $(CH_2)_n-$, $-O(CH_2)_m-$, $-NR^{13}-C(=O)-NR^{13}$, $-NR^{13}-C(=O)-(CH_2)_m-$, $-C(=O)NR^{13}-(CH_2)_m$, $-(CH_2)_n-Z_g-(CH_2)_n$, $-S-$, $-SO_2-$, $SO_2NR^7$, $SO_2NR^{10}-$, -Het-, wherein each CAP is, independently,

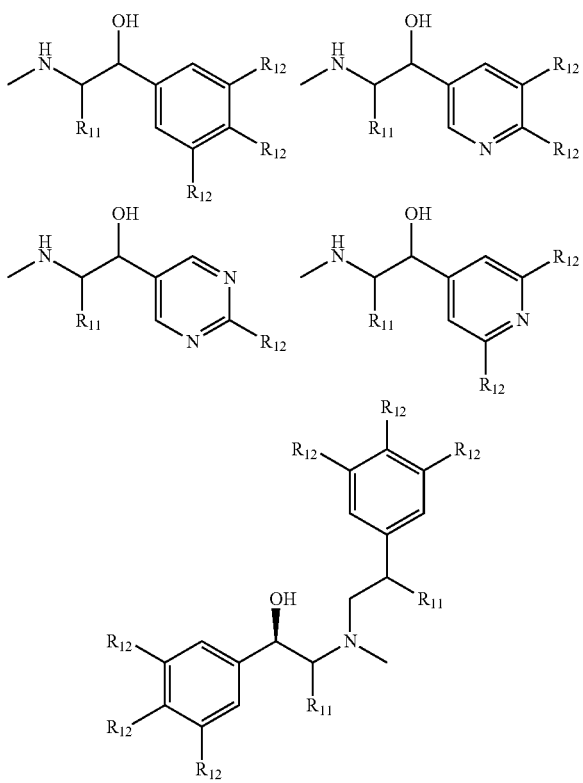

each $R^6$ is, independently, $-R^7$, $-OR^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

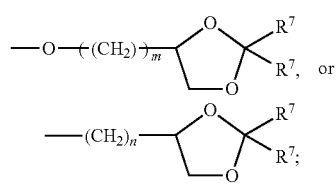

where when two $R^6$ are $-OR^{11}$ and are located adjacent to each other on a phenyl ring, alkyl moieties of the two $R^6$ may be bonded together to form a methylenedioxy group; with the proviso that when at least two $-CH_2OR^8$ are located adjacent to each other, the $R^8$ groups may be joined to form a cyclic mono- or di-substituted 1,3-dioxane or 1,3-dioxolane, each $R^7$ is, independently, hydrogen lower alkyl, phenyl, or substituted phenyl;

each $R^8$ is, independently, hydrogen, lower alkyl, $-C(=O)-R^{11}$, glucuronide, 2-tetrahydropyranyl, or

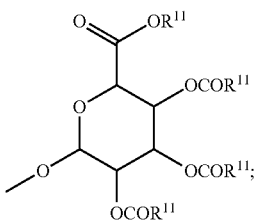

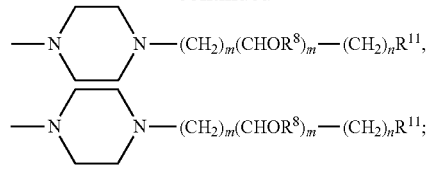

each R⁹ is, independently, —CO₂R¹³, —CON(R¹³)₂, —SO₂CH₂R¹³, or —C(=O)R¹³;

each R¹⁰ is, independently, —H, —SO₂CH₃, —CO₂R⁷, —C(=O)NR⁷R⁹, —C(=O)R⁷, or —(CH₂)ₘ—(CHOH)ₙ—CH₂OH;

each Z is, independently, CHOH, C(=O), —(CH₂)ₙ—, —CHNR¹³R¹³, C=NR¹³, or NR¹³;

each R¹¹ is, independently, hydrogen, lower alkyl, phenyl lower alkyl or substituted phenyl lower alkyl;

each R¹² is independently, —(CH₂)ₙ—SO₂CH₃, —(CH₂)ₙ—CO₂R¹³, —(CH₂)ₙ—C(=O)NR¹³R¹³, —(CH₂)ₙ—C(=O)R¹³, —(CH₂)ₙ—(CHOH)ₙ—CH₂OH, —NH—(CH₂)ₙ—SO₂CH₃, —NH—(CH₂)ₙ—C(=O)R¹¹, —NH—C(=O)—NH—C(=O)R¹¹, —C(=O)NR¹³R¹³, —OR¹¹, —NH—(CH₂)ₙ—R¹⁰, —Br, —Cl, —F, —I, SO₂NHR¹¹, —NHR¹³, —NH—C(=O)—NR¹³R¹³, NH—(CH₂)ₙ—SO₂CH₃, NH—(CH₂)ₙ—C(=O)R¹¹, —NH—C(=O)—NH—C(=O)R¹¹, —C(=O)NR¹³R¹³, —OR¹¹, —(CH₂)ₙ—NHR¹³, —NH—C(=O)—NR¹³R¹³, or —NH—(CH₂)ₙ—C(=O)—R¹³;

each R¹³ is, independently, hydrogen, lower alkyl, phenyl, substituted phenyl, —SO₂CH₃, —CO₂R⁷, —C(=O)NR⁷R⁷, —C(=O)NR⁷SO₂CH₃, —C(=O)NR⁷—CO₂R⁷, —C(=O)NR⁷—C(=O)NR⁷R⁷, —C(=O)NR⁷—C(=O)R⁷, —C(=O)NR⁷—(CH₂)ₘ—(CHOH)ₙ—CH₂OH, —C(=O)R⁷, —(CH₂)ₘ(CHOH)ₙ—CH₂OH, —(CH₂)ₘ—NR⁷R¹⁰, —(CH₂)ₘ—NR⁷R⁷R⁷, —(CH₂)ₘ—(CHOR⁸)ₘ—(CH₂)ₘNR⁷R⁷, —(CH₂)ₘ—NR¹⁰R¹⁰, —(CH₂)ₘ—(CHOR⁸)ₘ—(CH₂)ₘ NR⁷R⁷R⁷,

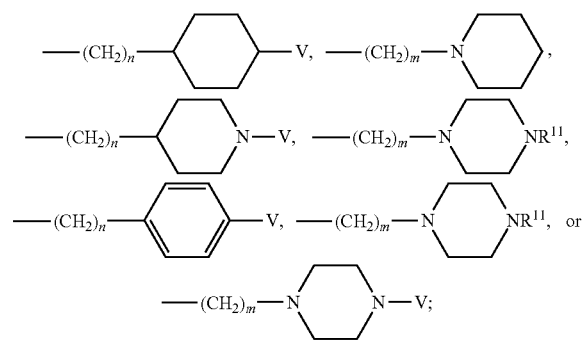

with the proviso that NR¹³R¹³ can be joined on itself to form one of the following:

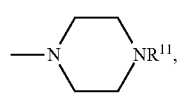

—N⌒N—(CH₂)ₘ(CHOR⁸)ₘ—(CH₂)ₙR¹¹,

—N⌒N—(CH₂)ₘ(CHOR⁸)ₘ—(CH₂)ₙR¹¹;

each Het is independently, —NR¹³, —S—, —SO—, —SO₂—; —O—, —SO₂NR¹³—, —NHSO₂—, —NR¹³CO—, —CONR¹³—;

each g is, independently, an integer from 1 to 6:

each m is, independently, an integer from 1 to 7;

each n is, independently, an integer from 0 to 7;

each Q is, independently, C—R⁵, C—R⁶, or a nitrogen atom, wherein at least one Q is CR⁵ and at most three Q in a ring are nitrogen atoms;

each V is, independently, —(CH₂)ₘ—NR⁷R¹⁰, —(CH₂)ₘ—NR⁷R⁷,

—(CH₂)ₘ—N⁺R¹¹R¹¹R¹¹,

—(CH₂)ₙ—(CHOR⁸)ₘ—(CH₂)ₘNR⁷R¹⁰, —(CH₂)ₙ—NR¹⁰R¹⁰—(CH₂)ₙ—(CHOR⁸)ₘ—(CH₂)ₘNR⁷R⁷,

—(CH₂)ₙ—(CHOR⁸)ₘ—(CH₂)ₘN⁺R¹¹R¹¹R¹¹ with the proviso that when V is attached directly to a nitrogen atom, then V can also be, independently, R⁷, R¹⁰, or (R¹¹)₂, wherein for any of the above compounds when two —CH₂OR⁸ groups are located 1,2- or 1,3- with respect to each other the R⁸ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all racemates, enantiomers, diastereomers, tautomers, polymorphs and pseudopolymorphs thereof.

The present invention also provides a method of promoting mucus clearance in mucosal surfaces, comprising:
administering an effective amount of a compound represented by formula to a mucosal surface of a subject.

The present invention also provides a method of treating chronic bronchitis, comprising:
administering an effective amount of a compound represented by formula (I) a subject in need thereof.

The present invention also provides a method of treating cystic fibrosis, comprising:
administering an effective amount of compound represented by formula (I) to a subect in need thereof.

The present invention also provides a method of treating rhinosinusitis, comprising:
administering an effective amount of a compound represented by a formula (I) to a subject in need thereof.

The present invention also provides a method of treating nasal dehydration, comprising:
administering an effective amount of a compound represented by for to the nasal passages of a subject in need thereof.

In a specific embodiment, the nasal dehydration is brought on by administering oxygen to the subject.

The present invention also provides a method of treating sinusitis, comprising:

administering an effective amount of a compound represented by formula (I) to a subject in need thereof.

The present invention also provides a method of treating pneumonia, comprising:

administering an effective amount of a compound represented by formula (I) to a subject in need thereof.

The present invention also provides a method of preventing ventilator-induced pneumonia, comprising:

administering an effective compound represented by formula to a subject by means of a ventilator.

The present invention also provides a method of treating asthma, comprising:

administering an effective amount of a compound represented by formula (I) to a subject in need thereof.

The present invention also provides a method of treating primary ciliary dyskinesia, comprising:

administering an effective amount of a compound represented by formula (I) to a subject in need thereof.

The present invention also provides a method of treating otitis media, comprising:

administering an effective amount of a compound represented by formula (I) to a subject in need thereof.

The present invention also provides a method of inducing sputum for diagnostic purposes, comprising:

administering an effective amount of compound represented by formula (I) to a subject in need thereof.

The present invention also provides a method of treating chronic obstructive pulmonary disease, comprising:

administering an effective amount of a compound represented by formula (I) to a subject in need thereof.

The present invention also provides a method of treating emphysema, comprising:

administering an effective amount of a compound represented by formula (I) to a subject in need thereof.

The present invention also provides a method of treating dry eye, comprising:

administering an effective amount of a compound represented by formula (I) to the eye of the subject in need thereof.

The present invention also provides a method of promoting ocular hydration, comprising:

administering an effective amount of a compound represented by formula (I) to the eye of the subject.

The present invention also provides a method of promoting corneal hydration, comprising:

administering an effective amount of a compound represented by formula (I) to the eye of the subject.

The present invention also provides a method of treating Sjögren's disease, comprising:

administering an effective amount of compound represented by formula (I) to a subject in need thereof.

The present invention also provides a method of treating vaginal dryness, comprising:

administering an effective amount of a compound represented by formula (I) to the vaginal tract of a subject in need thereof.

The present invention also provides a method of treating dry skin, comprising:

administering an effective amount of a compound represented by formula (I) to the skin of a subject in need thereof.

The present invention also provides a method of treating dry mouth (xerostomia), comprising:

administering an effective amount of compound represented by formula (I) to the mouth of the subject in need thereof.

The present invention also provides a method of treating distal intestinal obstruction syndrome, comprising:

administering an effective amount of compound represented by formula to a subject in need thereof.

The present invention also provides a method of treating esophagitis, comprising:

administering an effective amount of a compound represented by formula (I) to a subject in need thereof.

The present invention also provides a method of treating constipation, comprising:

administering an effective amount of a compound represented by formula (I) to a subject in need thereof. In one embodiment of this method, the compound is administered either orally or via a suppository or enema.

The present invention also provides a method of treating chronic diverticulitis comprising:

administering an effective amount of a compound represented by formula to a subject in need thereof.

BRIEF DESCRIPTION OF THE FIGURES

FIG. 4 shows the tautomers of the compounds of formula I.

DETAILED DESCRIPTION OF THE INVENTION

Figure 1:
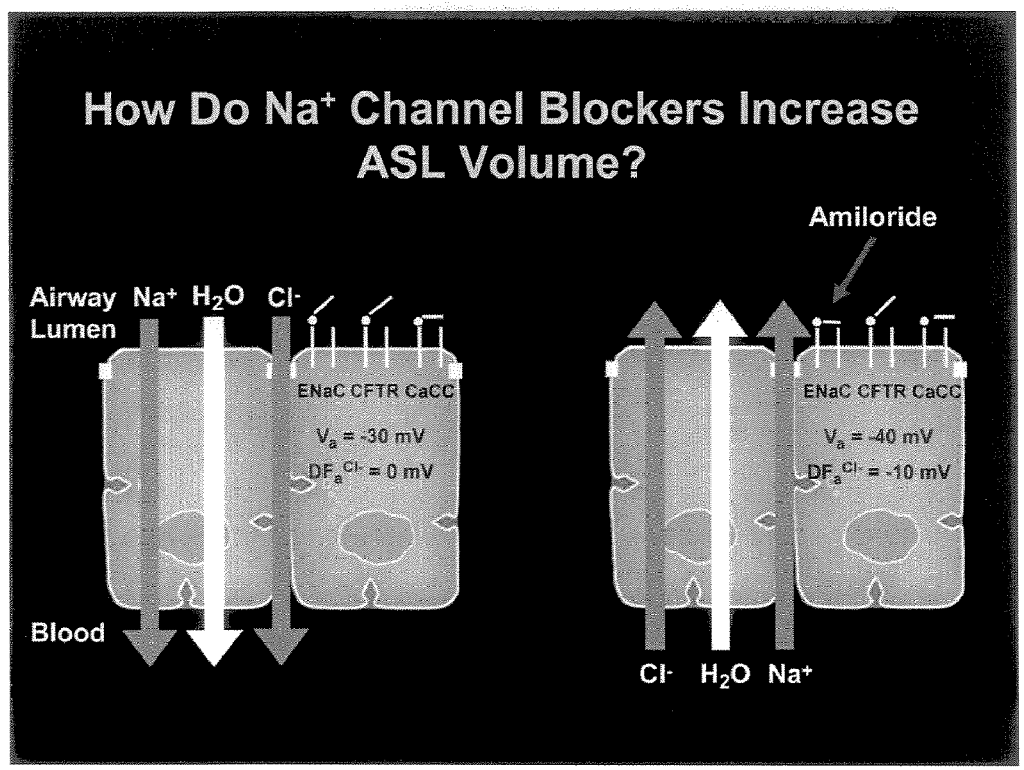
FIG. 1 shows the baseline activity of sodium channels before and after blockade with amiloride.

The present invention is based on the discovery that the compounds of formula (I) also possess both sodium channel blocking activity and beta agonist activity in the same molecule.

The present invention is also based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels and acting as beta-adrenergic receptor agonists as compared to the parent administered compound, after they are absorbed from mucosal surfaces after administration. This important property means that the compounds will have a lower tendency to cause undesired side-effects by blocking sodium channels and activating beta-receptors located at other untargeted locations in the body of the recipient, e.g., in the kidneys and heart.

Mono drug therapy leaves most major diseases such as chronic bronchitis and cystic fibrosis inadequately treated. It is therefore often necessary to discover and develop novel drugs or combination of drugs which treat and modulate multiple targets simultaneously (polypharmacology) with the goal of enhancing efficacy or improving safety relative to single target drugs. There are three possible ways to achieve this. 1) Combining therapeutic "cocktails" of two or more individual drugs; the benefits of this approach are often lessened by poor patient compliance. 2). A multiple component drug ("fixed combination" or multiple component drug) that contains two or more agents in a single tablet, liquid formulation, inhaler or dry powder device. This can sometimes improve patient compliance versus multiple component drugs but adds the complexity of carefully dosing so as to minimize multiple metabolic pathways. 3). A single molecular entity which can simultaneously modulate multiple drug targets (designed multiple ligands). The advantage of a multiple ligand over the first two approaches is that it improves compliance, enhances efficacy, it targets a known set of deficiencies in multiple systems with a single new chemical entity, it often lacks the unpredictable differences in the pharmacokinetic and pharmacodynamic variability between patients, it is often easier to formulate and potentially lowers the risk of drug-drug interactions compared to drug cocktails and multiple component drugs. It was therefore our goal to discover multiple ligands that have both sodium channel blocking activity as well as beta agonist activity.

The addition of beta-adrenergic receptor agonist activity to a sodium channel blocker will significantly increase the capacity to hydrate airway surfaces in subjects in need of hydration for therapeutic purposes. The mechanism by which beta-agonist activity adds to the hydration capacity of Na channel blockers alone, or beta-agonists alone, is described in the following diagrams that describe the electrochemical gradients for ion flows and the net secretion that results from these forces in airway epithelia.

As shown in FIG. 1, under baseline conditions human airway epithelia absorb NaCl and $H_2O$. Active $Na^+$ absorption drives this process. $Cl^-$ is absorbed passively with $Na^+$ to preserve electroneutrality. As there is no net driving force for $Cl^-$ to move across the apical cell membrane, $Cl^-$ is absorbed paracellularly in response to the transepithelial electric potential. Water moves cellularly and paracellularly in response to the osmotic gradients generated by NaCl absorption.

Application of a $Na^+$ channel blocker (as an example amiloride is shown) inhibits the entry of $Na^+$ into the cell which: (1) abolishes $Na^+$ absorption and (2) hyperpolarizes the apical cell membrane (Va). The hyperpolarization of Va generates an electrochemical driving force favoring $Cl^-$ secretion $Na^+$ now follows in the secretory direction via the paracellular path). The rate of $Cl^-$ secretion is proportional to the activity of the apical membrane $Cl^-$ channels which are typically 30-50% maximally active under basal conditions. In summary, application of a $Na^+$ channel blocker inhibits $Na^+$ absorption and triggers a modest amount of secretion. Note again that water will follow transcellularly in response to the secreted NaCl.

Figure 2:
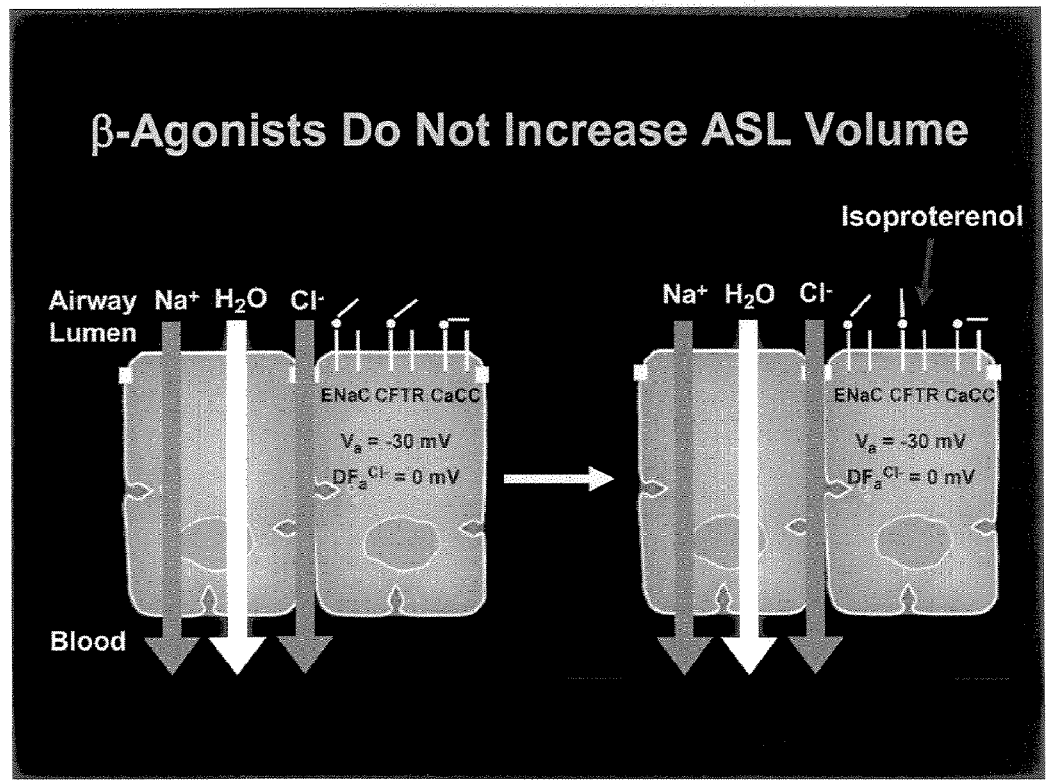
FIG. 2 shows the activity of sodium channels before and after the addition of a beta-agonist.

In contrast, as depicted in FIG. 2, addition of a beta-agonist (as an example isoproterenol is shown) alone to human airway epithelia produces no changes in $Na^+$ absorption or $Cl^-$ secretion. The reason for this absence of effect is that there is no electrochemical driving force for to move across the cell (See the following references: Intracellular Cl– activity and cellular Cl– pathways in cultured human airway epithelium. Am J. Physiol. 1989 May; 256 (5 Pt 1):C1033-44. Willumsen N J, Davis C W, Boucher R C Cellular Cl– transport in cultured cystic fibrosis airway epithelium. Am J. Physiol. 1989 May; 256 (5 Pt 1):C1045-53. Willumsen N J, Davis C W, Boucher R C Activation of an apical Cl– conductance by Ca2+ ionophores in cystic fibrosis airway epithelia. Am J. Physiol. 1989 February; 256 (2 Pt 1):C226-33. Willumsen N J, Boucher R C). Thus, a beta-agonist mediated activation of an apical membrane $Cl^-$ channel, usually CFTR via changes in cAMP, produces no change in the rate of movement of $Cl^-$ across the barrier and, hence, no change in transepithelial sodium chloride or water secretion.

Figure 3:
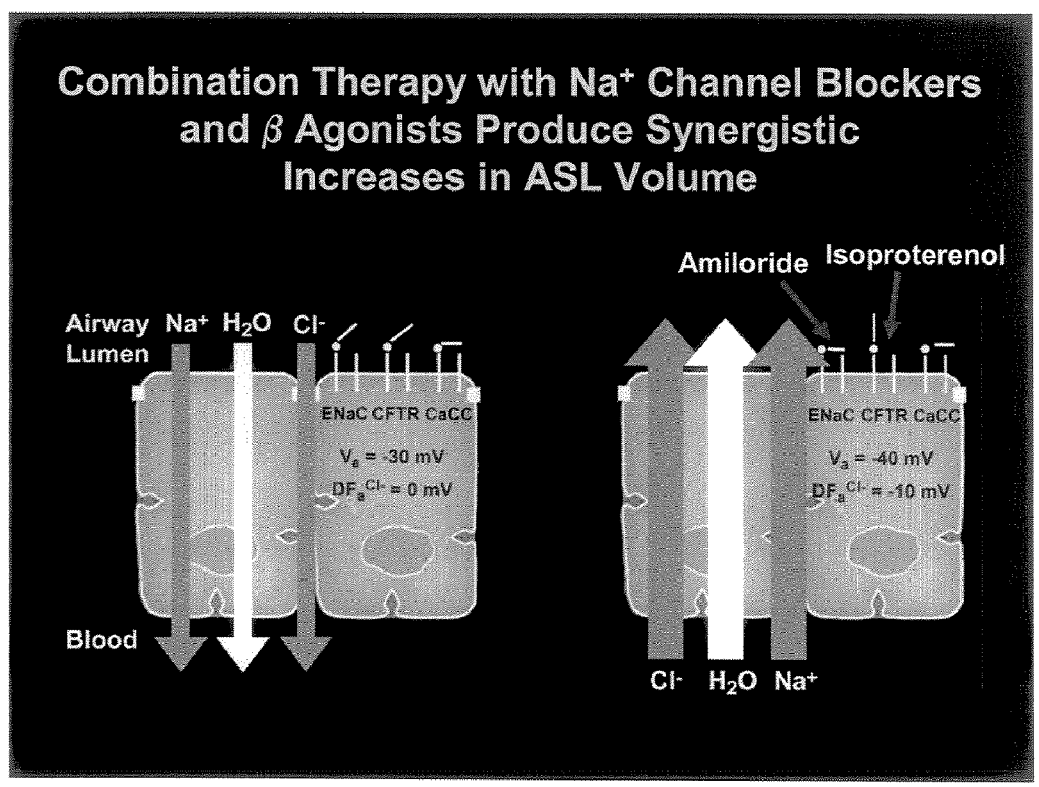
FIG. 3 shows the mechanism underlying the additivity of a Na channel blocker and a beta-agonist.

However, when a Na channel blocker is administered with a beta-agonist, additivity between these two classes of compounds is achieved with the result being accelerated $Cl^-$ (and $Na^+$, $H_2O$) secretion. The mechanism underlying the additivity is shown in FIG. 3. In the presence of a Na channel blocker, an electrochemical gradient for CF secretion is generated (also see FIG. 1). Now when a beta-agonist is present, it converts the apical membrane CFTR from ~30% basal activity to ~100% activity via beta-agonist induced increase in cAMP that ultimately activates CFTR via PKA (protein kinase A). Because there is an electrochemical driving force favoring $Cl^-$ secretion as a result of ENaC blockade, the increase in $Cl^-$ channel activity translates into increasing $Cl^-$ (and $Na^+$, $H_2O$) secretion. Thus, the hydration capacity of the epithelia is greatly enhanced by the presence of both $Na^+$ channel blocker and beta-adrenergic receptor agonist activities in the environment bathing the human airway epithelia as compared to just $Na^+$ channel blocker or beta-adrenergic receptor agonist by themselves. A discovery of this invention is that administration of both activities contained within the same molecule to the epithelium is at least as effective as sequential administration of a Na channel blocker followed by a beta-agonist and therefore has the advantages cited earlier.

The compounds of formula I exist primarily as a combination of the three tautomers shown FIG. 4, FIG. 4 shows the three tautomers represented in formula I that exist in solution. Previous studies by Smith et al. have shown that the free base exists primarily as the acylimino tautomer, whereas the physiologically active species exists as the protonated form of the acylamino tautomer (FIG. 1, ref R L Smith et. Al. Journal of the American Chemical Society, 1979, 101, 191-201). These structural representations have been used to represent amiloride and its analogs in both the patent and scientific literature. We use both the acylamino and acylimino representations for convenience throughout this patent with the understanding that the structures are in reality a hybrid of the three forms with the actual amount of each dependent on the pH, the cite of action and the nature of the substituents.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or $—N(R^2)_2$. The alkyl moiety of the lower alkoxy groups is the same as described above. Examples of mononuclear aryl include phenyl groups. The phenyl group may be unsubstituted or substituted as described above. The preferred identity of Y is —N(R$^2$)$_2$. Particularly preferred are such compounds where each R$^2$ is hydrogen.

R$^1$ may be hydrogen or lower alkyl. Hydrogen is preferred for R$^1$.

Each R$^2$ may be, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

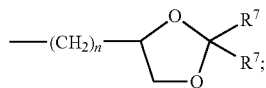

Hydrogen and lower alkyl, particularly C$_1$-C$_3$ alkyl are preferred for R$^2$. Hydrogen is particularly preferred.

R$^3$ and R$^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of R$^3$ and R$^4$ is a group represented by formula (A).

Preferred compounds are those where one of R$^3$ and R$^4$ is hydrogen and the other is represented by formula (A).

In formula (A), the moiety —(C(R$^L$)$_2$)$_o$-x-(C(R$^L$)$_2$)$_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Accordingly, the sum of o and p can be 1, 2, 3, 4, 5, 6, 7, 8, 9 or 10, or any subrange therebetween. Preferably, the sum of o and p is from 2 to 6. In a particularly preferred embodiment, the sum of o and p is 4.

The linking group in the alkylene chain, x, may be, independently, O, NR$^{10}$, C(=O), CHOH, C(=N—R$^{10}$), CHNR$^7$R$^{10}$, or represents a single bond. Therefore, when x represents a single bond, the alkylene chain bonded to the ring is represented by the formula —(C(R$^L$)$_2$)$_{o+p}$—, in which the sum o+p is from 1 to 10.

Each R$^L$ may be, independently, —R$^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_n$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

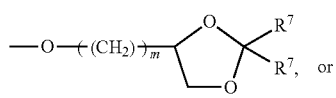

-continued

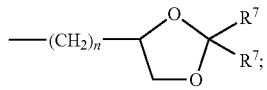

The preferred R$^L$ groups include —H, —N(R$^7$)$_2$, especially where each R$^7$ is hydrogen.

In the alkylene chain in formula (A), it is preferred that when one R$^L$ group bonded to a carbon atoms is other than hydrogen, then the other R$^L$ bonded to that carbon atom is hydrogen, i.e., the formula —CHR$^L$—. It is also preferred that at most two R$^L$ groups in an alkylene chain are other than hydrogen, where in the other R$^L$ groups in the chain are hydrogens. Even more preferably, only one R$^L$ group in an alkylene chain is other than hydrogen, where in the other R$^L$ groups in the chain are hydrogens. In these embodiments, it is preferable that x represents a single bond.

In another particular embodiment of the invention, all of the R$^L$ groups in the alkylene chain are hydrogen. In these embodiments, the alkylene chain is represented by the formula —(CH$_2$)$_o$-x-(CH$_2$)$_p$—.

As discussed above, each R$^5$ is, independently,

Link —(CH$_2$)$_n$—CR$^{11}$R$^{11}$-CAP, Link —(CH$_2$)$_n$(CHOR$^8$)(CHOR$^8$)$_n$—CR$^{11}$R$^{11}$-CAP, Link —(CH$_2$CH$_2$O)$_m$—CH$_2$—CR$^{11}$R$^{11}$-CAP, Link —(CH$_2$CH$_2$O)$_m$—CH$_2$CH$_2$—CR$^{11}$R$^{11}$-CAP, Link —(CH$_2$)$_n$—(Z)$_g$—CR$^{11}$R$^{11}$-CAP, Link —(CH$_2$)$_n$(Z)$_g$—(CH$_2$)$_m$—CR$^{11}$R$^{11}$-CAP, Link —(CH$_2$)$_n$—NR$^{13}$—CH$_2$(CHOR$^8$)(CHOR$^8$)$_n$—CR$^{11}$R$^{11}$-CAP, Link —(CH$_2$)$_n$—(CHOR$^8$)$_m$CH$_2$—NR$^{13}$—(Z)$_g$—CR$^{11}$R$^{11}$-CAP, Link —(CH$_2$)$_n$NR$^{13}$—(CH$_2$)$_m$(CHOR$^8$)$_n$CH$_2$NR$^{13}$—(Z)$_g$—CR$^{11}$R$^{11}$-CAP, Link —(CH$_2$)$_m$—(Z)$_g$—(CH$_2$)$_m$—CR$^{11}$R$^{11}$-CAP, Link NH—C(=O)—NH—(CH$_2$)$_m$—CR$^{11}$R$^{11}$-CAP, Link —(CH$_2$)$_m$—C(=O)NR$^{13}$—(CH$_2$)$_m$—CR$^{11}$R$^{11}$-CAP, Link —(CH$_2$)$_n$—(Z)$_g$—(CH$_2$)$_m$—(Z)$_g$—CR$^{11}$R$^{11}$-CAP, Link —Z$_g$—(CH$_2$)$_m$-Het-(CH$_2$)$_m$—CR$^{11}$R$^{11}$-CAP.

As discussed above, each Link is, independently,

—O—, (CH$_2$)$_n$—, —O(CH$_2$)$_m$—, —NR$^{13}$—C(=O)—NR$^{13}$, NR$^{13}$—C(=O)—(CH$_2$)$_m$—, —C(=O)NR$^{13}$—(CH$_2$)$_m$, —(CH$_2$)$_n$—Z$_g$—(CH$_2$)$_n$—, —S—, —SO—, SO$_2$NR$^7$—, SO$_2$NR$^{10}$—, -Het-.

Each CAP is, independently,

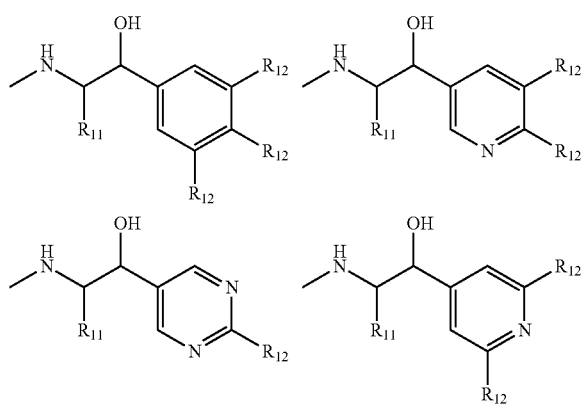

-continued

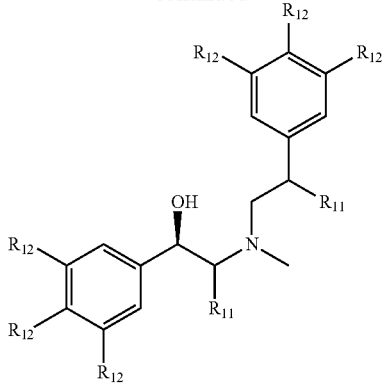

Each $R^6$ is, independently, $-R^7$, $-OR^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_m-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

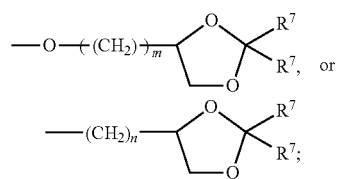

where when two $R^6$ are $-OR^{11}$ and are located adjacent to each other on a phenyl ring, the alkyl moieties of the two $R^6$ may be bonded together to form a methylenedioxy group; with the proviso that when at least two $-CH_2OR^8$ are located adjacent to each other, the $R^8$ groups may be joined to form a cyclic mono- or di-substituted 1,3-dioxane or 1,3-dioxolane, Each $R^7$ is, independently, hydrogen lower alkyl, phenyl, or substituted phenyl.

Each $R^8$ is, independently, hydrogen, lower alkyl, $-C(=O)-R^{11}$, glucuronide, 2-tetrahydropyranyl, or

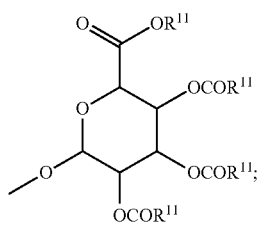

Each $R^9$ is, independently, $-CO_2R^{13}$, $-CON(R^{13})_2$, $-SO_2CH_2R^{13}$, or $-C(=O)R^{13}$.

Each $R^{10}$ is, independently, $-H$, $-SO_2CH_3$, $-CO_2R^7$, $-C(=O)NR^7R^9$, $-C(=O)R^7$, or $-(CH_2)_m-(CHOH)_n-CH_2OH$.

Each Z is, independently, CHOH, C(=O), $-(CH_2)_n-$, CHNR$^{13}$R$^{13}$, C=NR$^{13}$, or NR$^{13}$.

Each $R^{11}$ is, independently, hydrogen, lower alkyl, phenyl lower alkyl or substituted phenyl lower alkyl.

each $R^{12}$ is independently, $-(CH_2)_n-SO_2CH_3$, $-(CH_2)_n-CO_2R^{13}$, $-(CH_2)_n-C(=O)NR^{13}R^{13}$, $-(CH_2)_n-C(=O)R^{13}$, $-(CH_2)_n-(CHOH)_n-CH_2OH$, $-NH-(CH_2)_n-SO_2CH_3$, $NH-(CH_2)_n-C(=O)R^{11}$, $NH-C(=O)-NH-C(=O)R^{11}$, $-C(=O)NR^{13}R^{13}$, $-OR^{11}$, $-NH-(CH_2)_n-R^{10}$, $-Br$, $-Cl$, $-F$, $-I$, $SO_2NHR^{11}$, $-NHR^{13}$, $-NH-C(=O)-NR^{13}R^{13}$, $NH-(CH_2)_n-SO_2CH_3$, $NH-(CH_2)_n-C(=O)R^{11}$, $-NH-C(=O)-NH-C(=O)R^{11}$, $-C(=O)NR^{13}R^{13}$, $-OR^{11}$, $-(CH_2)_n-NHR^{13}$, $-NH-C(=O)-NR^{13}R^{13}$, or $-NH-(CH_2)_n-C(=O)-R^{13}$.

Each $R^{13}$ is, independently, hydrogen, lower alkyl, phenyl, substituted phenyl, $-SO_2CH_3$, $-CO_2R^7$, $-C(=O)NR^7R^7$, $-C(=O)NR^7SO_2CH_3$, $-C(=O)NR^7-CO_2R^7$, $-C(=O)NR^7-C(=O)NR^7R^7$, $-C(=O)NR^7-C(=O)R^7$, $-C(=O)NR^7-(CH_2)_m-(CHOH)_n-CH_2OH$, $-C(=O)R^7$, $-(CH_2)_m-(CHOH)_n-CH_2OH$, $-(CH_2)_m-NR^7R^{10}$,

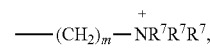

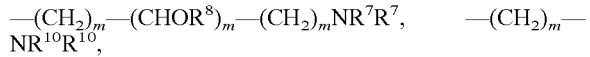

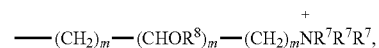

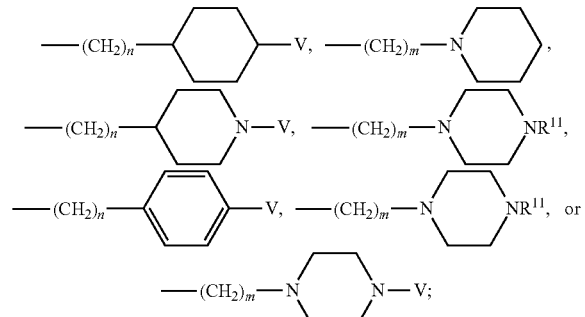

with the proviso that NR$^{13}$R$^{13}$ can be joined on itself to form a ring comprising one of the following:

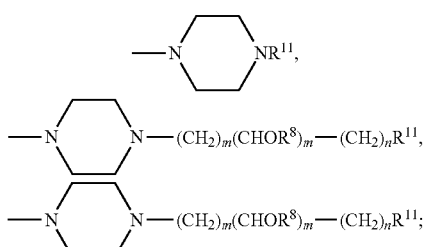

Each Het is independently, $-NR^{13}$, $-S-$, $-SO-$, $-SO_2-$, $-O-$, $-SO_2NR^{13}-$, $-NHSO_2-$, $-NR^{13}CO-$, or $-CONR^{13}-$.

Each g is, independently, an integer from 1 to 6.
Each m is, independently, an integer from 1 to 7.
Each n is, independently, an integer from 0 to 7.
Each Q is, independently, C—$R^5$, C—$R^6$, or a nitrogen atom, wherein at least one Q is C—$R^5$, and where at most three Q in a ring are nitrogen atoms;
Each V is, independently, —$(CH_2)_m$—$NR^7R^{10}$, —$(CH_2)_m$—$NR^7R^7$,

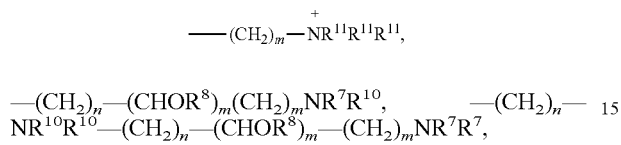

—$(CH_2)_n$—$(CHOR^8)_m(CH_2)_mNR^7R^{10}$, —$(CH_2)_n$—$NR^{10}R^{10}$—$(CH_2)_n$—$(CHOR^8)_m$—$(CH_2)_mNR^7R^7$,

—$(CH_2)_n$—$(CHOR^8)_m$—$(CH_2)_m\overset{+}{N}R^{11}R^{11}R^{11}$ with the proviso that when V is attached directly to a nitrogen atom, then V can also be, independently, $R^7$, $R^{10}$, or $(R^{11})_2$;

In one embodiment of the invention, when two —$CH_2OR^8$ groups are located 1,2- or 1,3- with respect to each other the $R^8$ groups may be joined to form a cyclic mono- or di-substituted 1,3-dioxane or 1,3-dioxolane;

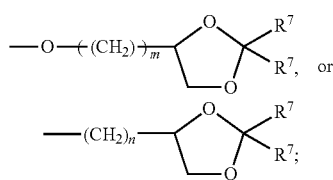

In the present invention, when two $R^6$ are —$OR^{11}$ and are located adjacent to each other on a phenyl ring, the alkyl moieties of the two $R^6$ may be bonded together to form a methylenedioxy group.

In the present invention, when at least two —$CH_2OR^8$ are located adjacent to each other, the $R^8$ groups may be joined to form a cyclic mono- or di-substituted 1,3-dioxane or 1,3-dioxolane.

In addition, one of more of the $R^6$ groups can be one of the $R^5$ groups which fall within the broad definition of $R^6$ set forth above.

When two $R^6$ are —$OR^{11}$ and are located adjacent to each other on a phenyl ring, the alkyl moieties of the two $R^6$ groups may be bonded together to form a methylenedioxy group, i.e., a group of the formula —O—$CH_2$—O—.

As discussed above, $R^6$ may be hydrogen. Therefore, 1, 2, 3, or 4 $R^6$ groups may be other than hydrogen. Preferably at most 3 of the $R^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Q in formula (A) is C—$R^5$, C—$R^6$, or a nitrogen atom, in which at least one Q is C—$R^5$ where at most three Q in a ring are nitrogen atoms. Thus, there may be 1, 2, or 3 nitrogen atoms in a ring. Preferably, at most two Q are nitrogen atoms. More preferably, at most one Q is a nitrogen atom.

In one particular embodiment, the nitrogen atom is at the 3-position of the ring. In another embodiment of the invention, each Q is either C—$R^5$ or C—$R^6$, i.e., there are no nitrogen atoms in the ring. In another embodiment, one Q is C—$R^5$.

More specific examples of suitable groups represented by formula (A) are shown in formulas (B)-(E) below:

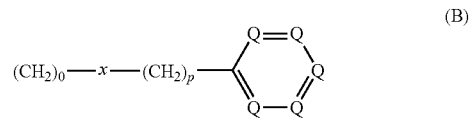

(B)

where o, x, p, $R^5$, and $R^6$, are as defined above;

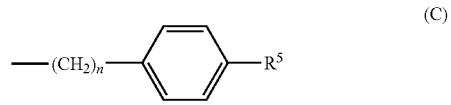

(C)

where n is an integer from 1 to 10 and $R^5$ is as defined above;

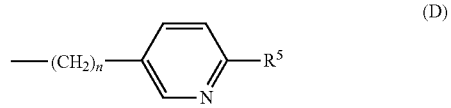

(D)

where n is an integer from 1 from 10 and $R^5$ is as defined above;

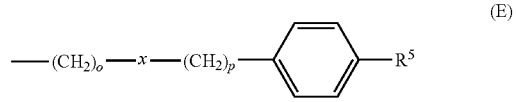

(E)

where o, x, p, and $R^5$ are as defined above.

In a preferred embodiment of the invention, Y is —$NH_2$.
In another preferred embodiment, $R^2$ is hydrogen.
In another preferred embodiment, $R^1$ is hydrogen.
In another preferred embodiment, X is chlorine.
In another preferred embodiment, $R^3$ is hydrogen.
In another preferred embodiment, $R^L$ is hydrogen
In another preferred embodiment, o is 4.
In another preferred embodiment, p is 0.
In another preferred embodiment, the sum of o and p is 4.
In another preferred embodiment, x represents a single bond.
In another preferred embodiment, $R^6$ is hydrogen.
In another preferred embodiment, at most one Q is a nitrogen atom.
In another preferred embodiment, no Q is a nitrogen atom.
In a preferred embodiment of the present invention:
X is halogen;
Y is —$N(R^7)_2$;
$R^1$ is hydrogen or $C_1$-$C_3$ alkyl;
$R^2$ is —$R^7$, —$OR^7$, $CH_2OR^7$, or —$CO_2R^7$;
$R^3$ is a group represented by formula (A); and
$R^4$ is hydrogen, a group represented by formula (A), or lower alkyl;

In another preferred embodiment of the present invention:
X is chloro or bromo;
Y is —N(R$^7$)$_2$;
R$^2$ is hydrogen or C$_1$-C$_3$ alkyl;
at most three R$^6$ are other than hydrogen as described above;
at most three R$^L$ are other than hydrogen as described above; and
at most 2 Q are nitrogen atoms.

In another preferred embodiment of the present invention:
Y is —NH$_2$;

In another preferred embodiment of the present invention:
R$^4$ is hydrogen;
at most one R$^L$ is other than hydrogen as described above;
at most two R$^6$ are other than hydrogen as described above; and
at most 1 Q is a nitrogen atom.

In another preferred embodiment of the present invention the compound of formula (1) is represented by the formula

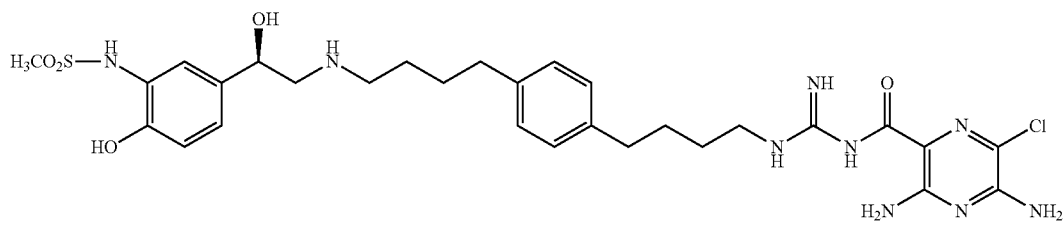

In another preferred embodiment of the present invention the compound of formula (1) is represented by the formula:

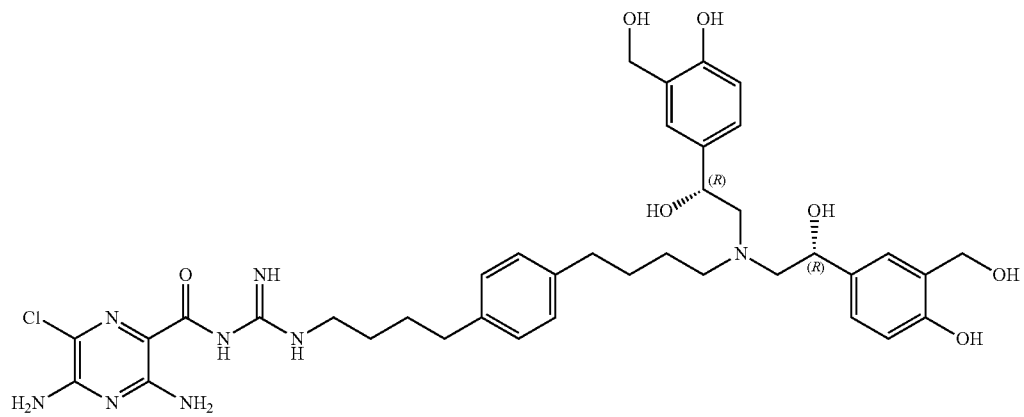

In another preferred embodiment of the present invention the compound of formula (1) is represented by the formula:

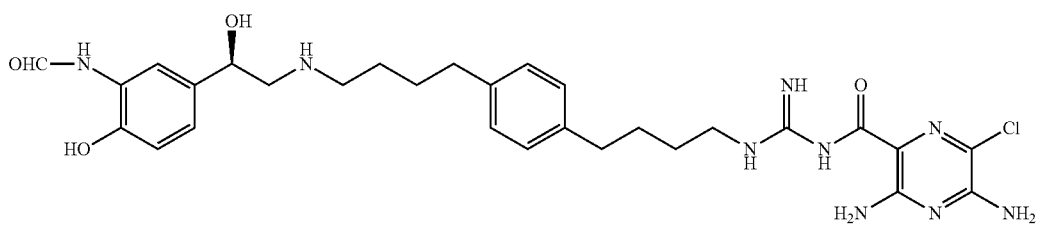

In another preferred embodiment of the present invention the compound of formula (1) is represented by the formula:

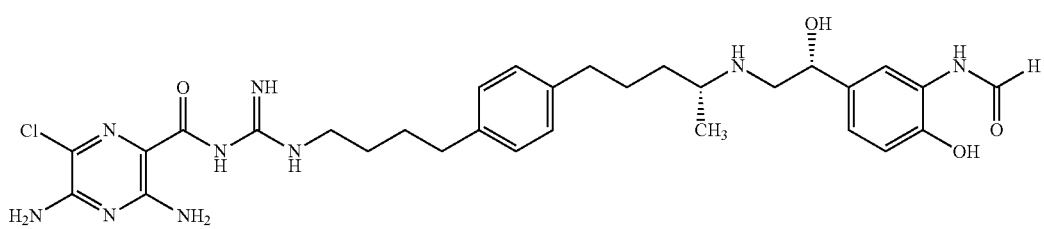

In another preferred embodiment of the present invention h compound of formula (1) is represented by the formula:
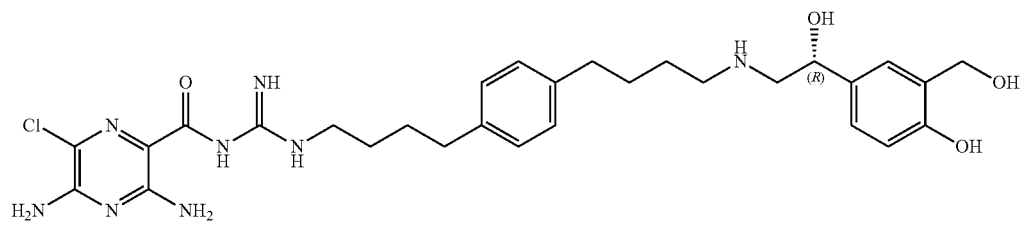
In another preferred embodiment of the present invention the compound of formula (1) is represented by the formula:
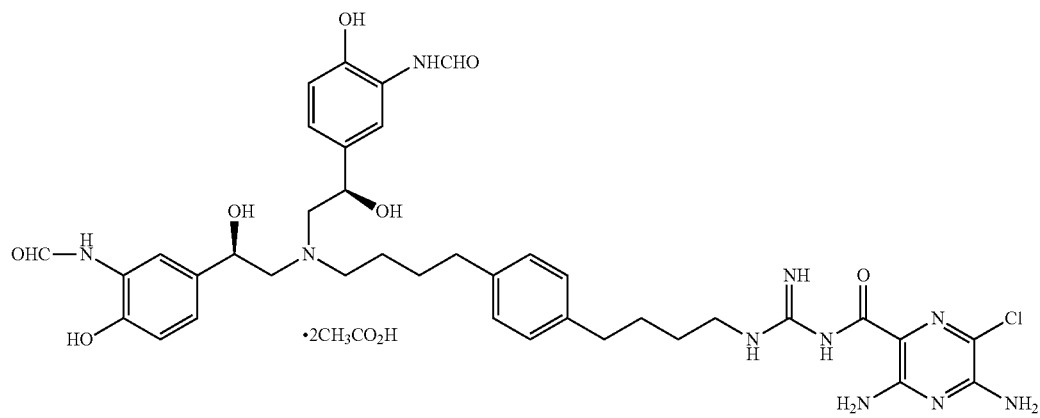
In another preferred embodiment of the present invention the compound of formula (1) is represented by the formula:
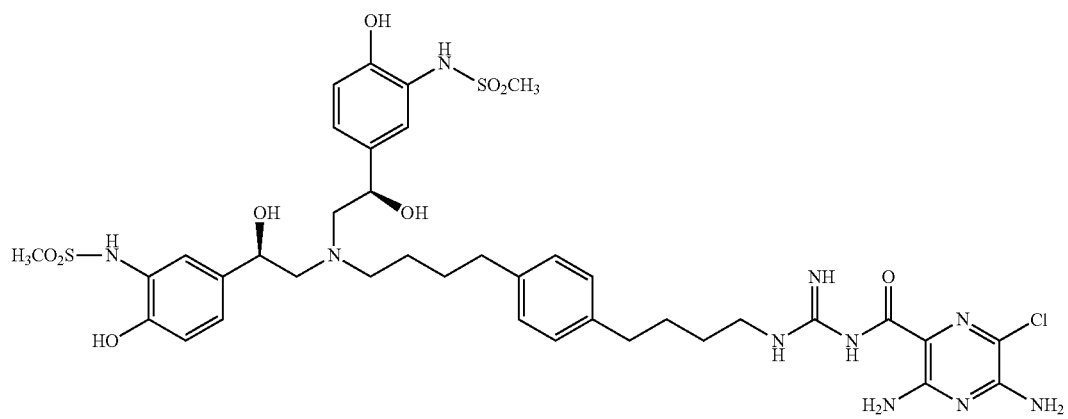

In another preferred embodiment of the present invention the compound of formula (1) is represented by the formula:

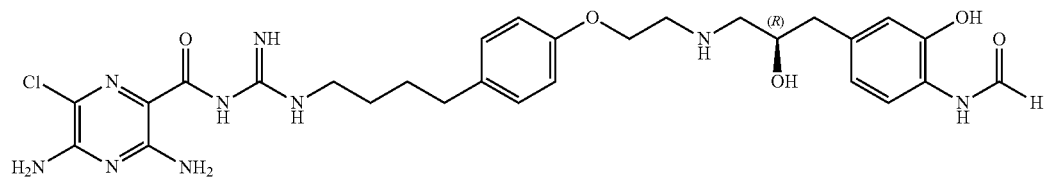

In another preferred embodiment of the present invention the compound of formula (1) is represented by the formula:

In another preferred embodiment of the present invention the compound of formula (1) is represented by the formula:

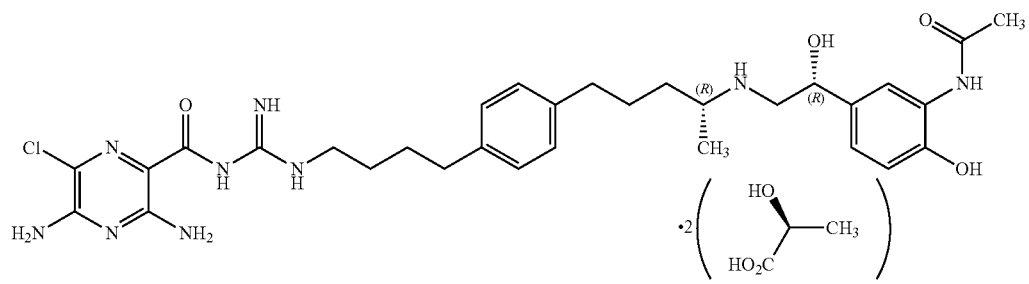

In another preferred embodiment of the present invention the compound of formula (1) is represented by the formula:

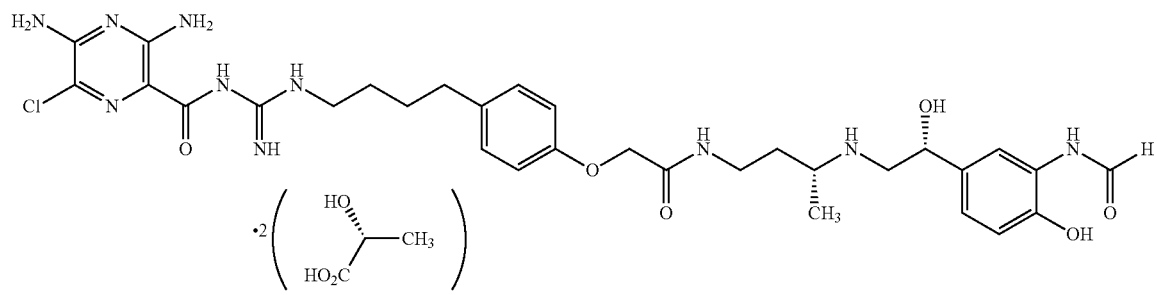

In another preferred embodiment of the present invention the compound of formula (1) is represented by the formula:

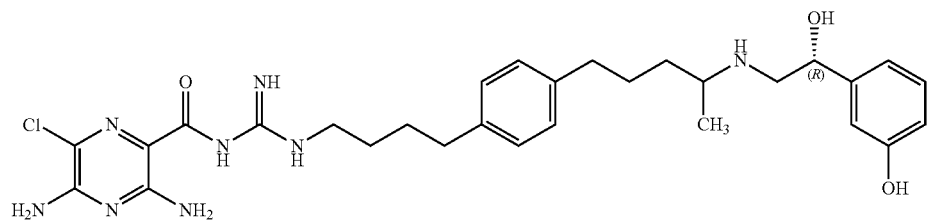

In another preferred embodiment of the present invention the compound of formula (1) is represented by the formula:

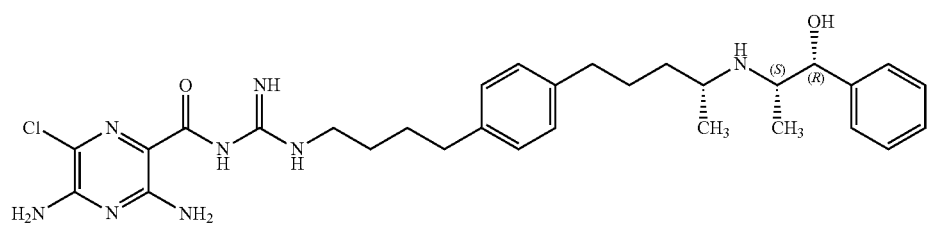

In another preferred embodiment of the present invention the compound of formula (1) is represented by the formula:

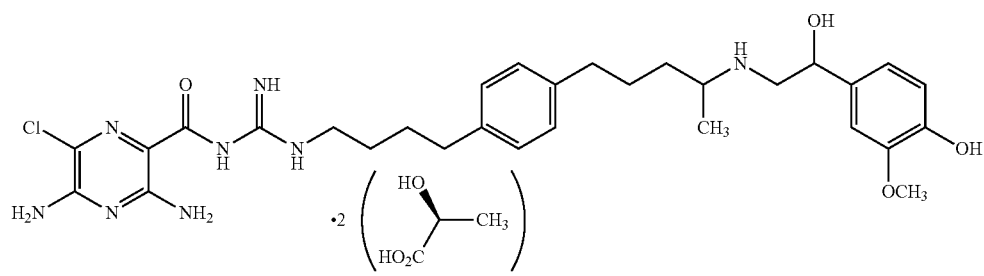

In another preferred embodiment of the present invention the compound of formula (1) is represented by the formula:

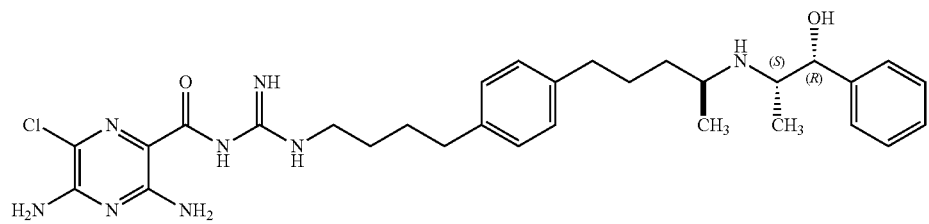

In another preferred embodiment of the present invention the compound of formula (1) is represented by the formula:

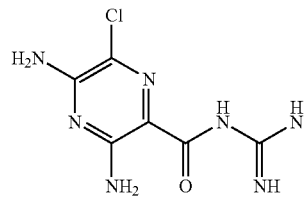 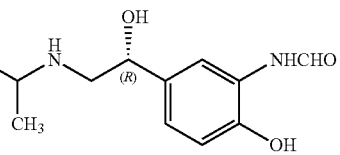

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, tautomers and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers and as beta receptor agonists. By blocking epithelial sodium channels as well as activating beta-receptors present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., *staphylococcus* infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral (vaginal) surfaces, ocular surfaces or surfaces of the eye, the inner ear and the middle ear. For example, the active compounds of the present invention may be administered by any suitable means, including locally/topically, orally, or rectally, in an effective amount.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution yet serves as a depot of drug which gradually becomes bioavailable as it slowly dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656,256, and U.S. Pat. No. 5,292,498, each of which is incorporated herein by reference.

Bronchodilators can also be used in combination with compounds of the present invention. These bronchodilators include, hut are not limited to, anticholinergic agents including but not limited to ipratropium bromide, as well as compounds such as theophylline and aminophylline. These compounds may be administered in accordance with known techniques, either prior to or concurrently with the active compounds described herein.

Ionic and organic osmolytes can also be used in combination with compounds of the present invention. Ionic osmolytes useful include any salt consisting of a pharmaceutically acceptable anion and a pharmaceutical cation. Organic osmolytes include, but are not limited to, sugars, sugar alcohols and organic osmolytes. Detailed examples of ionic and non-ionic osmolytes are given in U.S. Pat. No. 6,926,911 incorporated herein by reference. A particularly useful ionic osmolyte is hypertonic sodium chloride or sodium nitrite. A particularly useful organic osmolyte is the reduced sugar mannitol.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 may be used to ensure retention in the nasal cavity.

In the manufacture of a formulation according to the invention, active agents or the physiologically acceptable salts or free bases thereof are typically admixed with, inter cilia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by a suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Nolctar Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^{4}$ M.

In another embodiment, they are administered by administering an aerosol suspension of respirable or non-respirable particles (preferably non-respirable particles) comprised of active compound, which the subject inhales through the nose. The respirable or non respirable particles may be liquid or solid. The quantity of active agent included may b an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 ($19^{th}$ ed. 1995), incorporated herein by reference. Pharmaceutical formulations suitable for nasal administration may be prepared as described in U.S. Pat. Nos. 4,389,393 to Schor, 5,707,644 to Illum; 4,294,829 to Suzuki; and 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% v/v of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below:

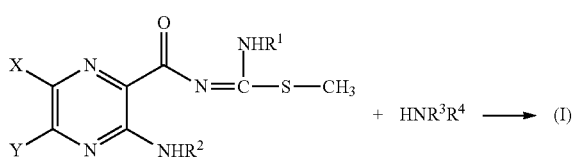 + HNR³R⁴ ⟶ (I)

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Other methods useful for the preparation of these compounds, especially for the preparation of the novel HNR³R⁴ fragment are described in, for example, U.S. Pat. No. 6,858,614, U.S. Pat. No. 6,858,615, and U.S. Pat. No. 6,903,105, incorporated herein by reference. Schemes 1 to 9 are representative of, but not limited to, procedures used to prepare the sodium channel blockers/beta adrenergic agonists described herein.

Scheme 1. Synthesis of Compound 12

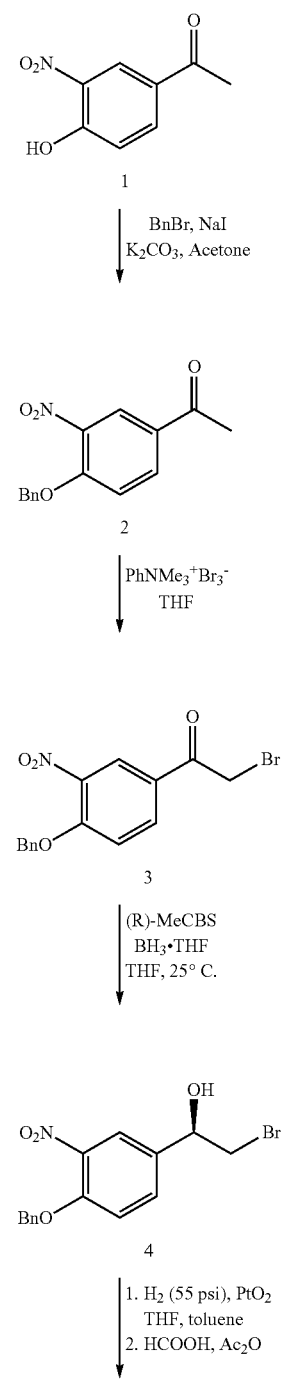

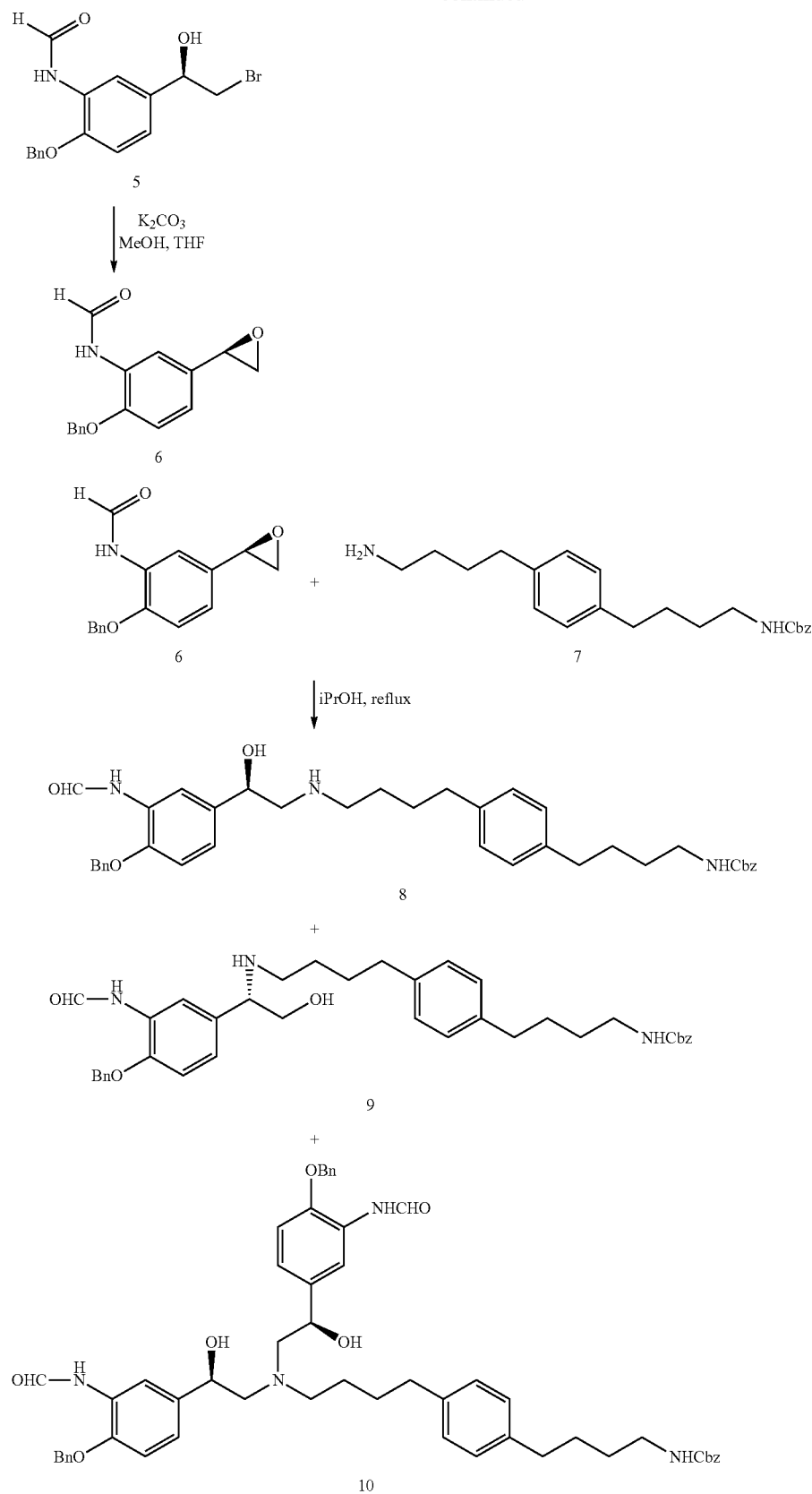

-continued
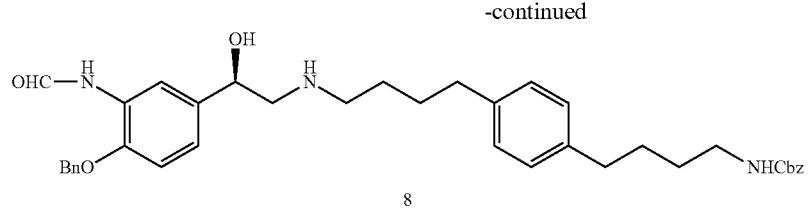
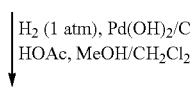
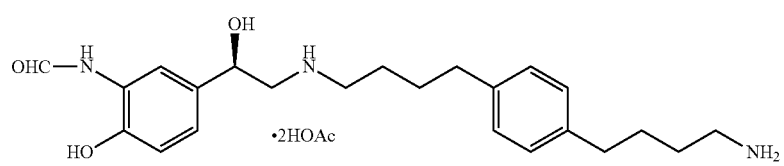
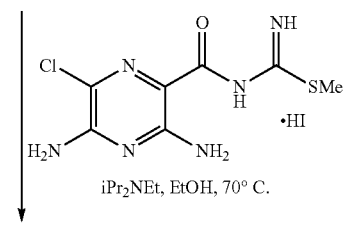
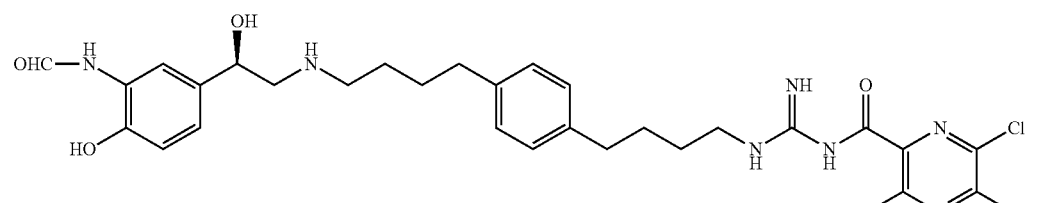
Scheme 2. Synthesis of Compound 14
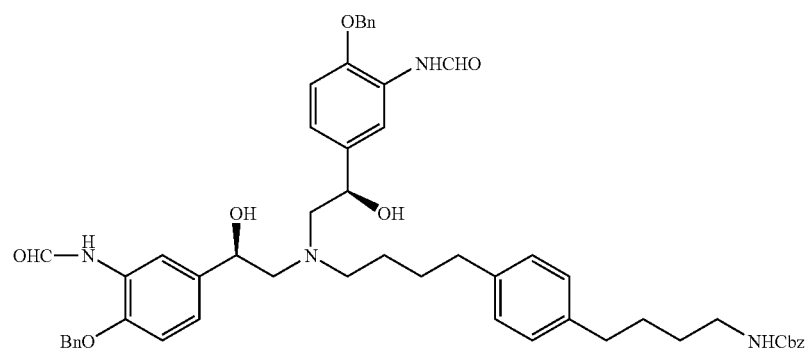
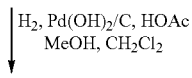

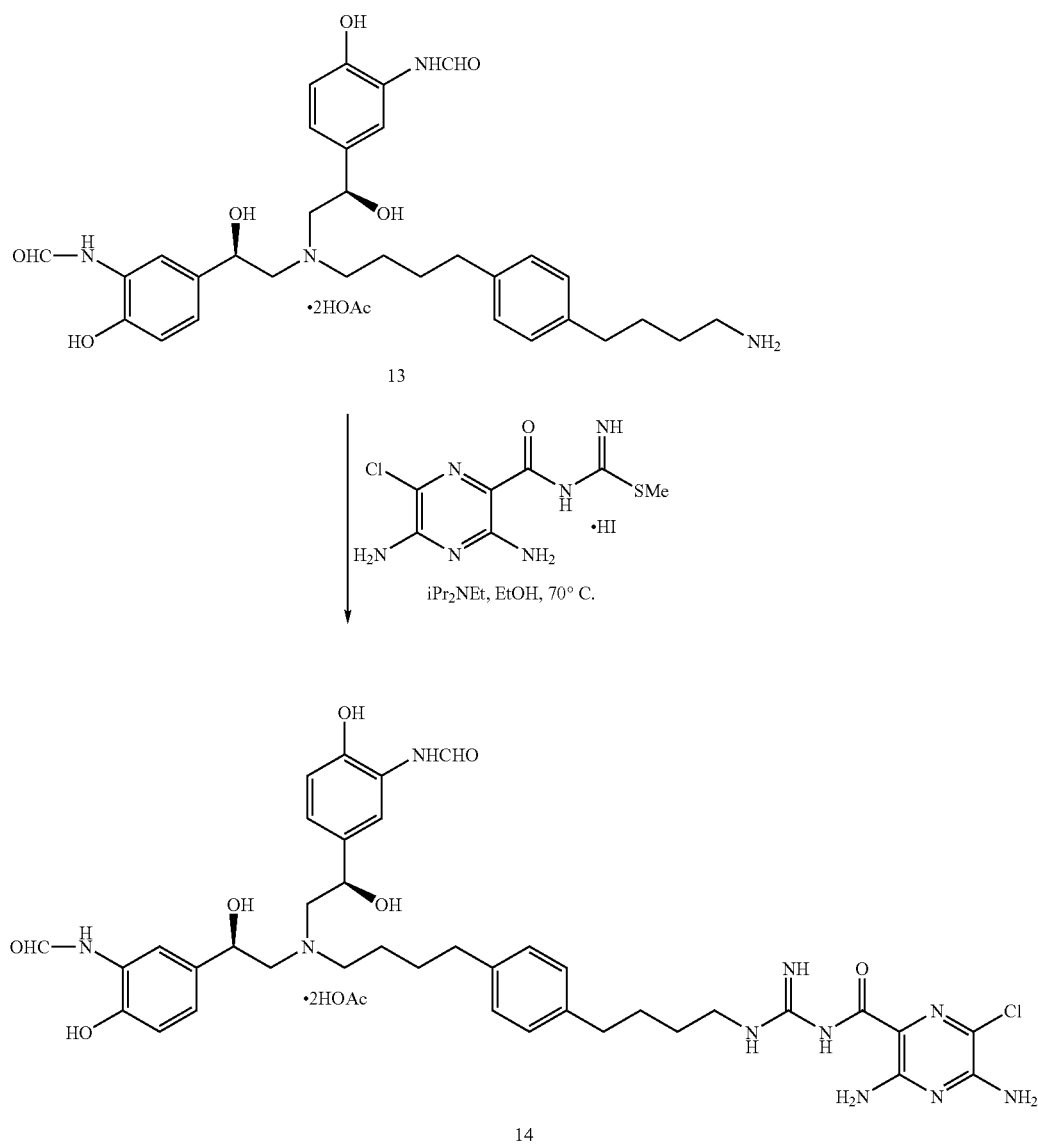
Scheme 3: Synthesis of Compound 19
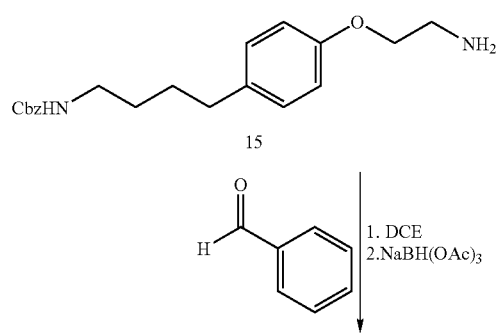

-continued
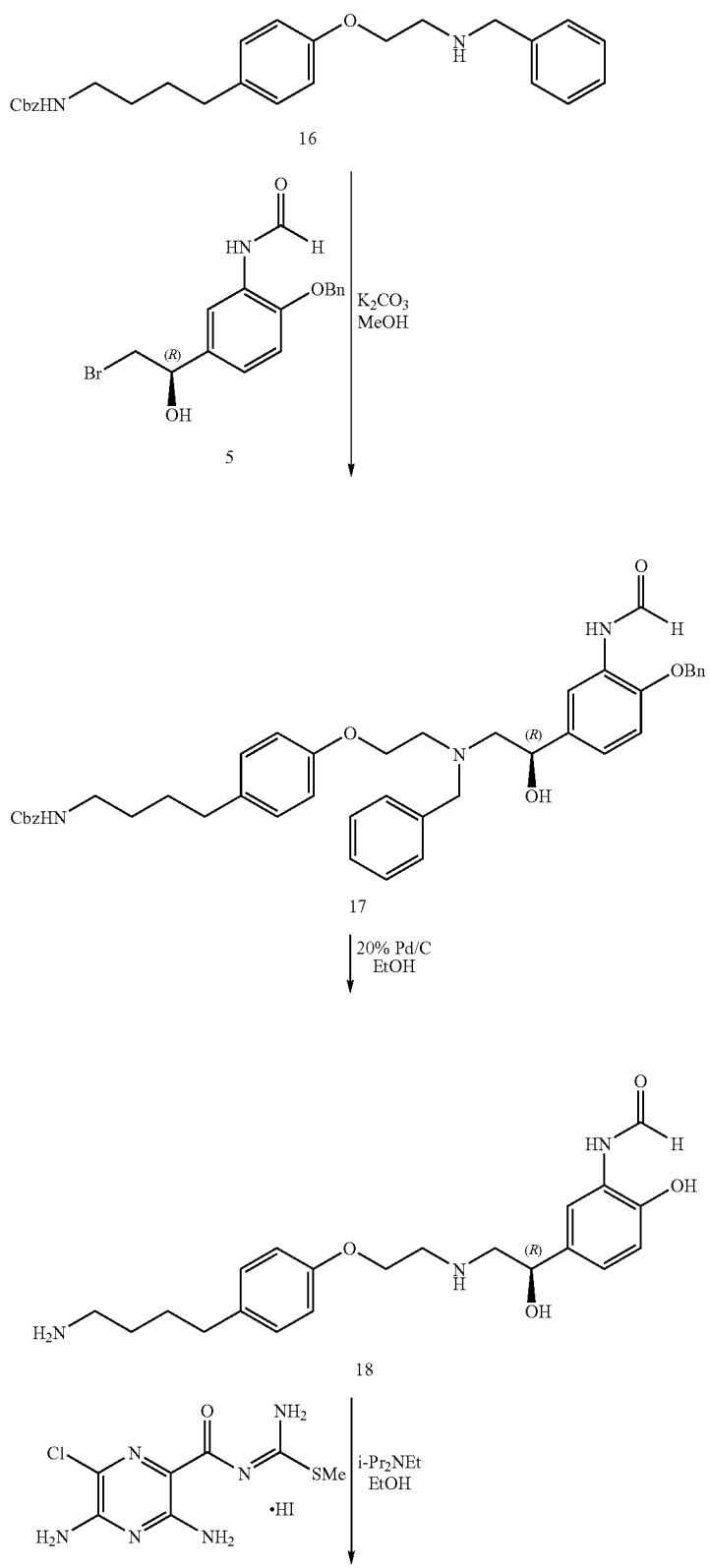

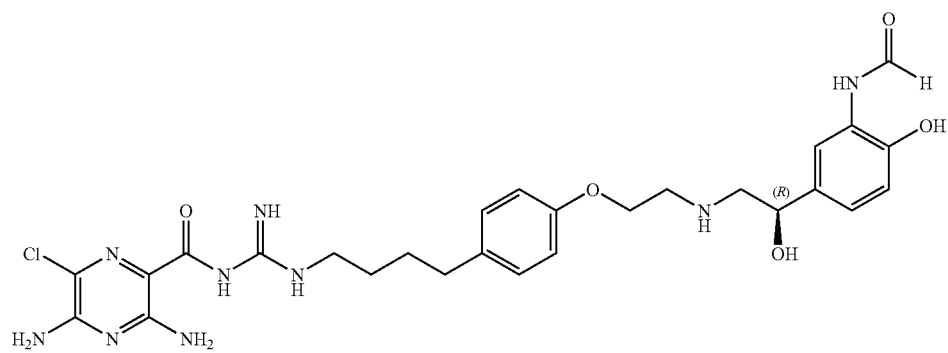
19
Scheme 4. Synthesis of Compound 30
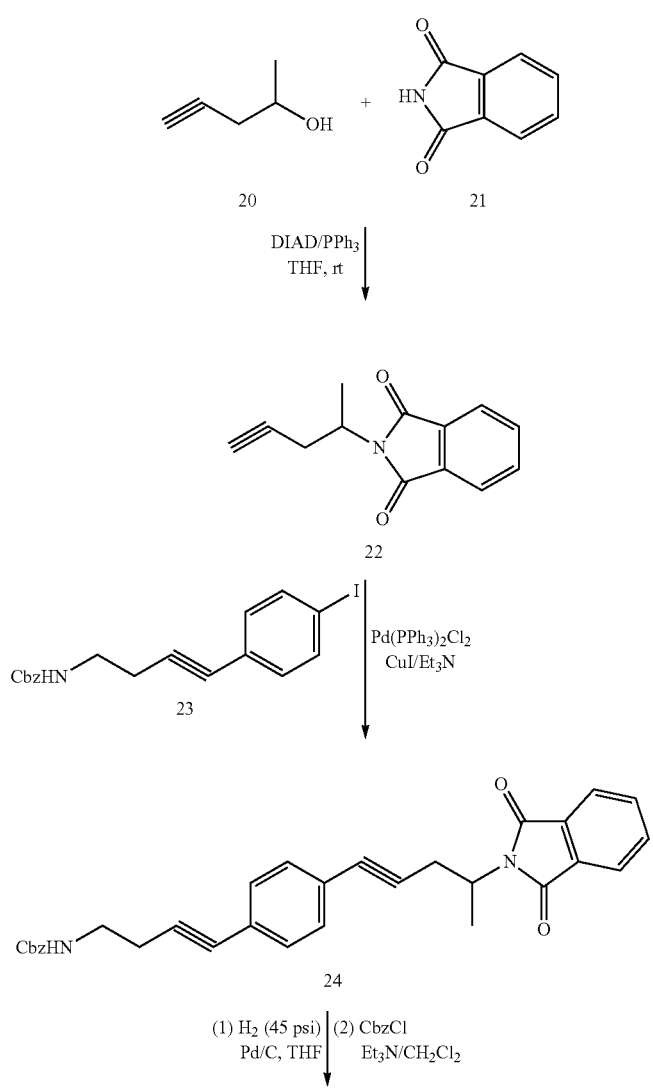

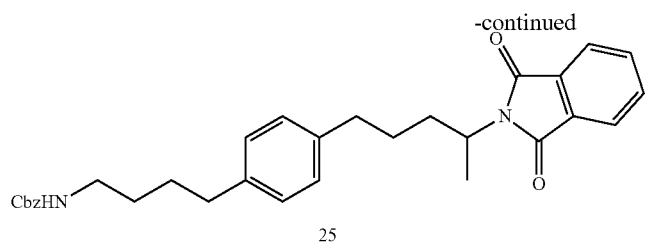
25
NH₂NH₂
EtOH
reflux
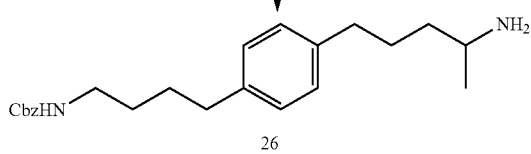
26
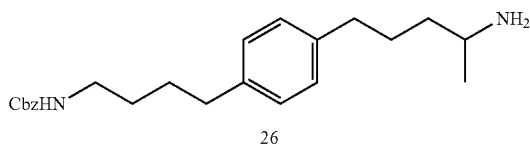
26
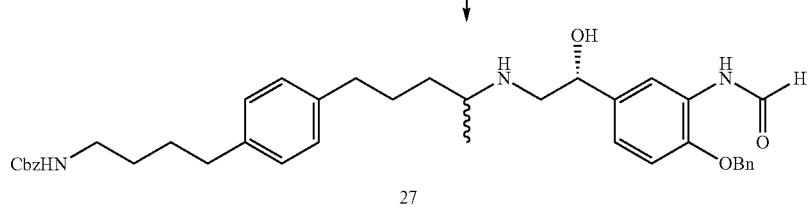
5
K₂CO₃/CHCl₃
reflux
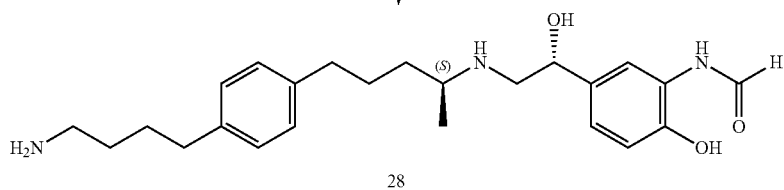
27
H₂ (1 atm) | EtOH
Pd/C
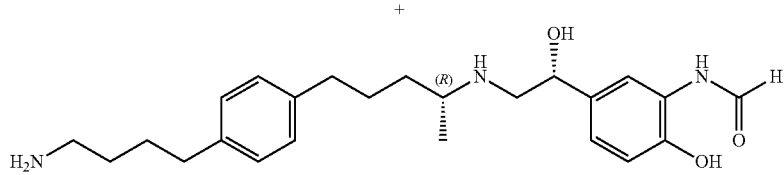
28
+
29
EtOH/DIPEA

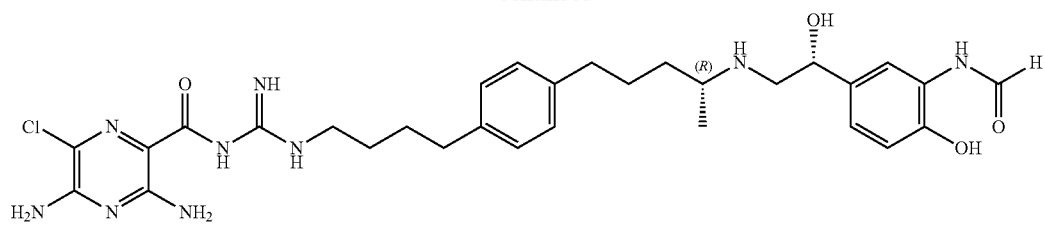
30
Scheme 5. Synthesis of Compound 40
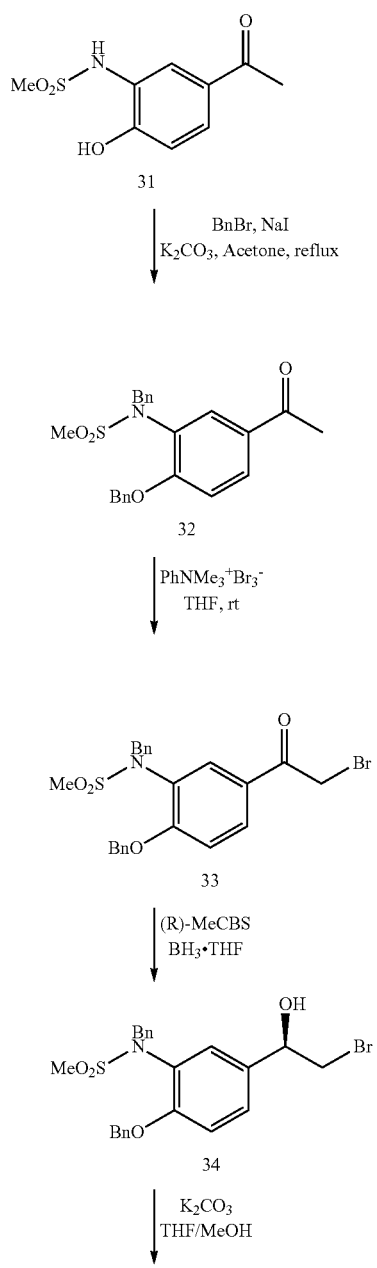

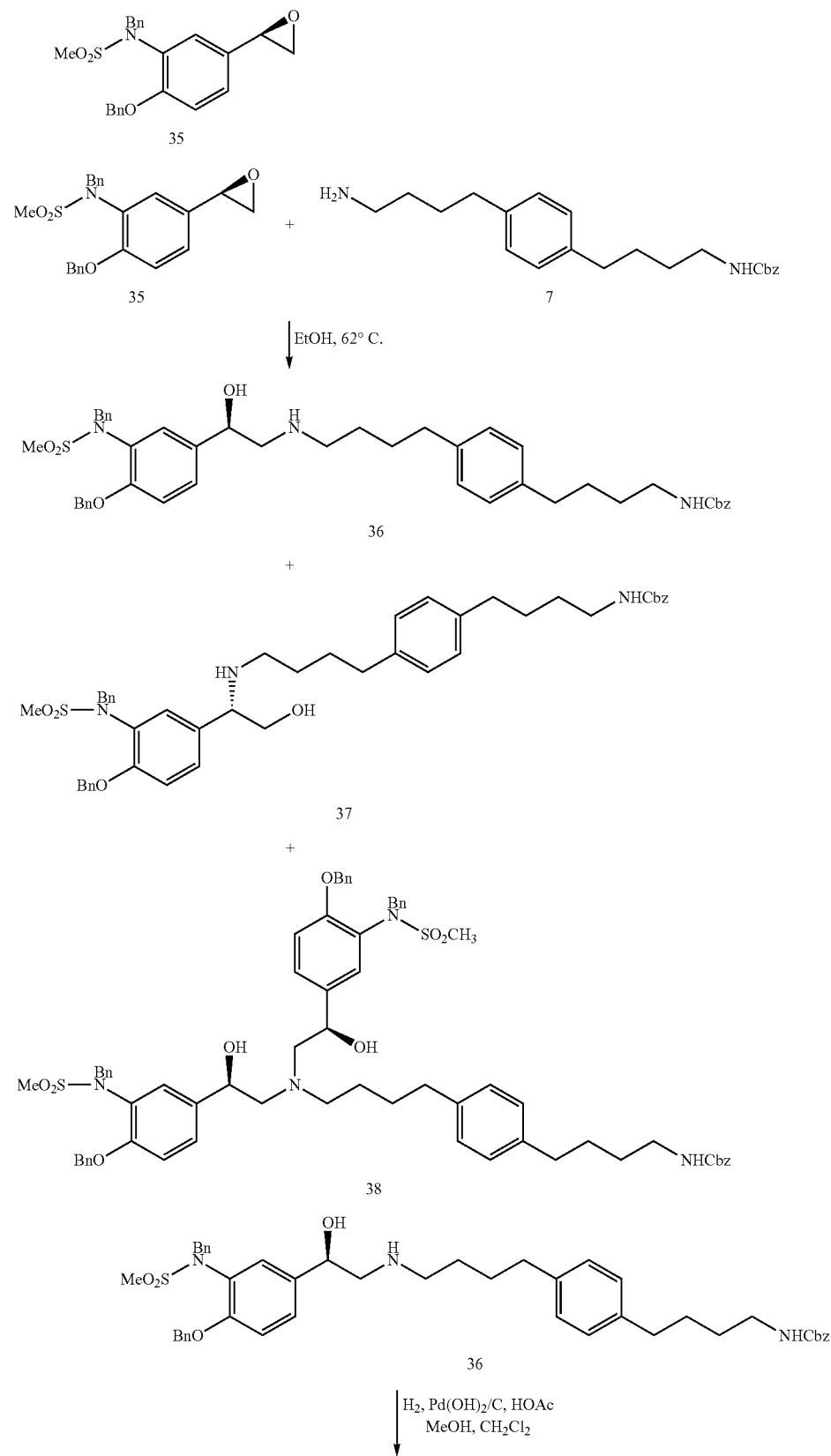

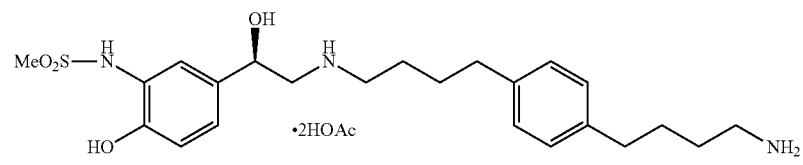
39
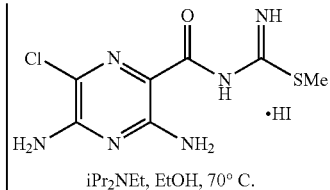
iPr$_2$NEt, EtOH, 70° C.
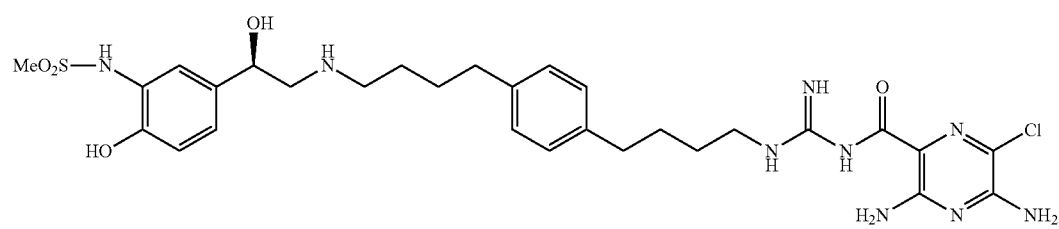
40
Scheme 6. Synthesis of Compound 42
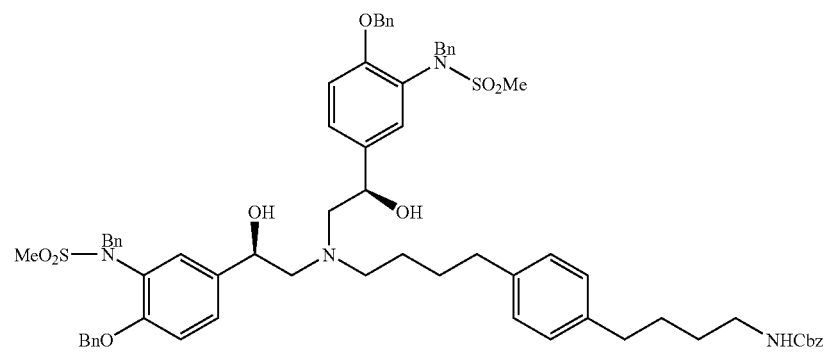
38
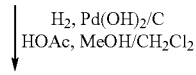

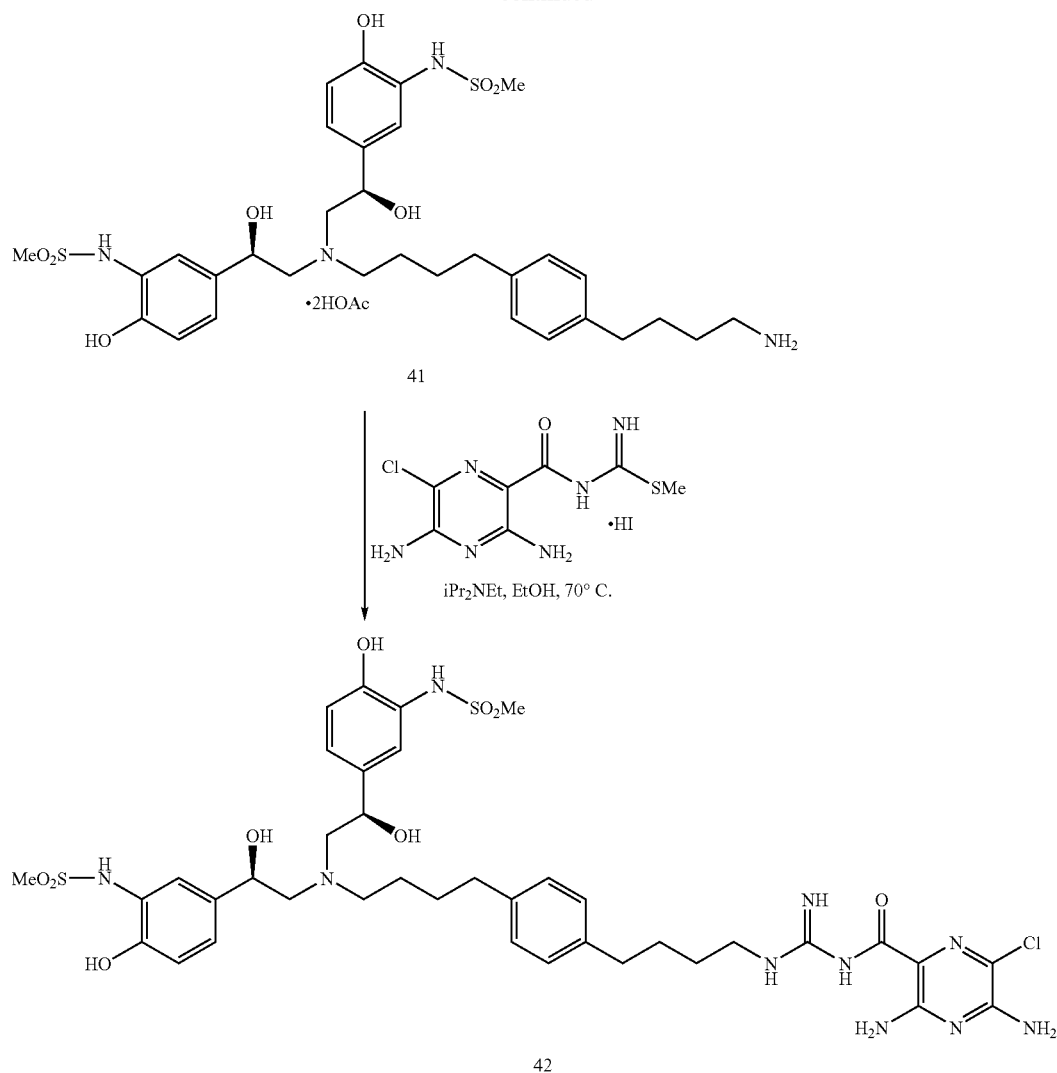
41
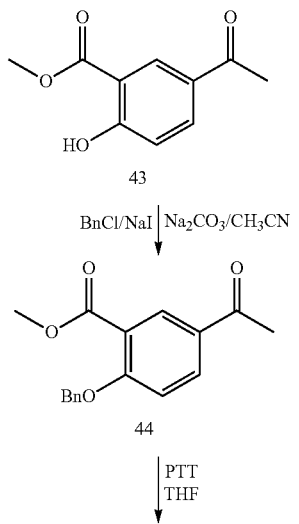
Scheme 7: Synthesis of Compound 55

-continued
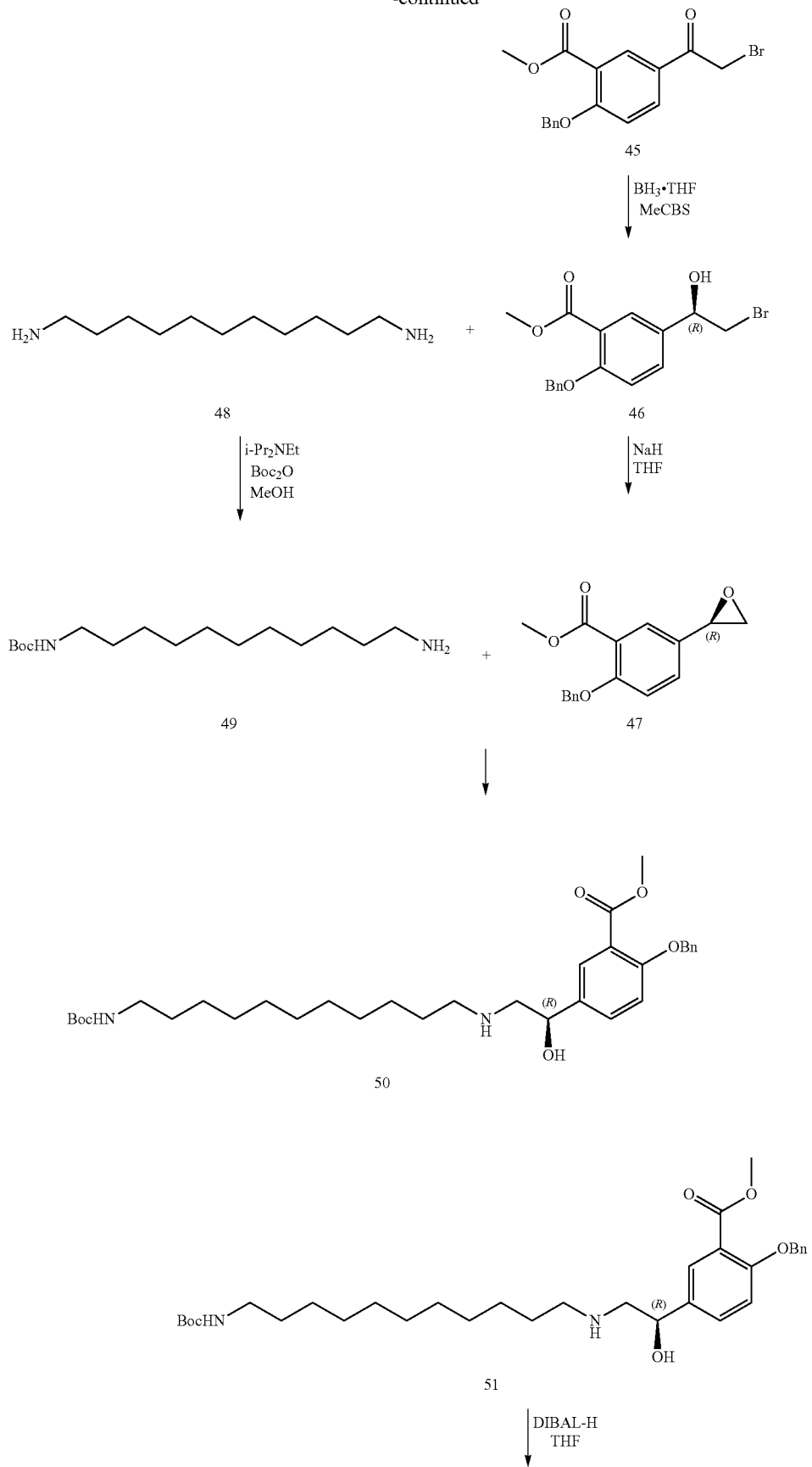

-continued
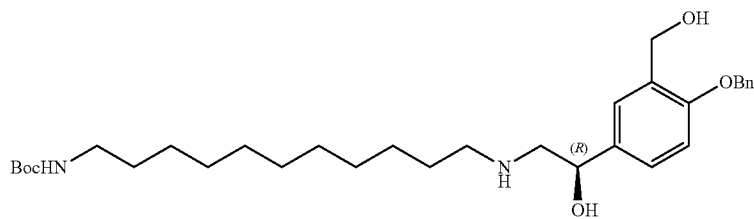
52
H₂ (1 atm)
10% Pd/C
EtOH
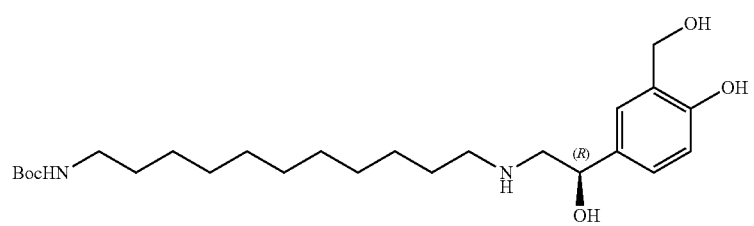
53
TMSI
CH₂Cl₂
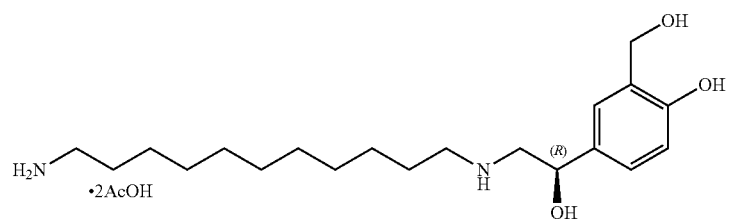
54
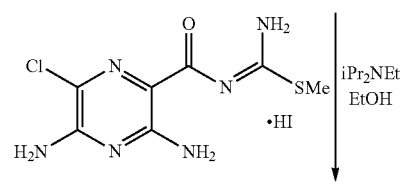
iPr₂NEt
EtOH
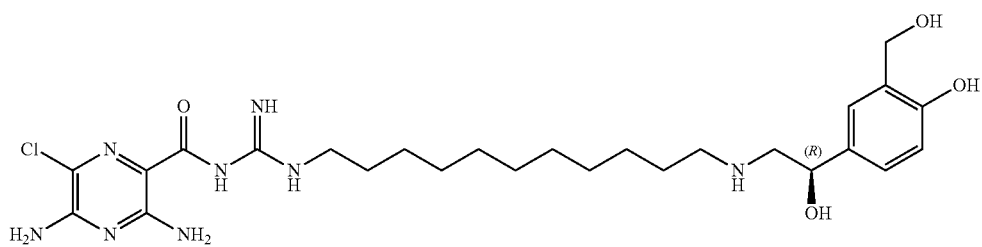
55

Scheme 8: Synthesis of Compound 63
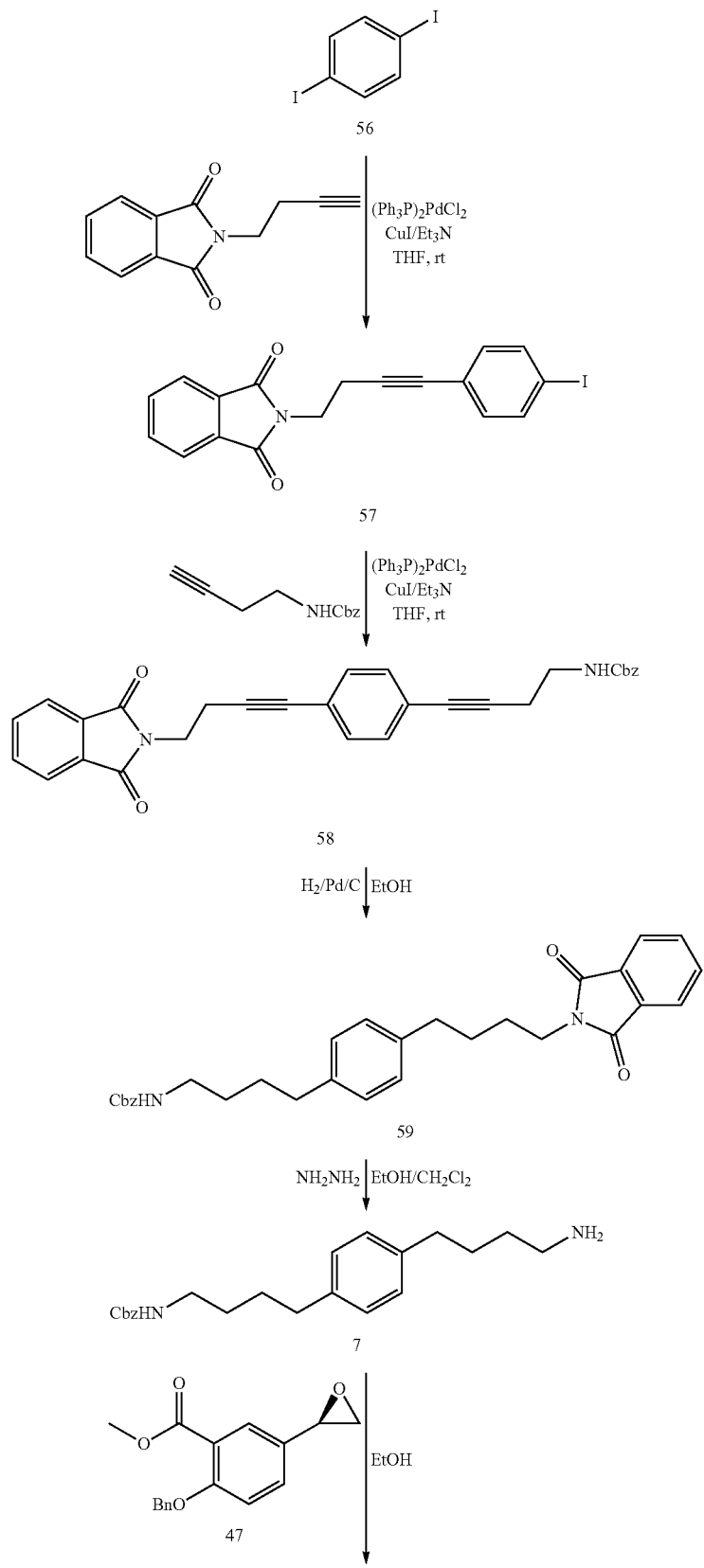

-continued
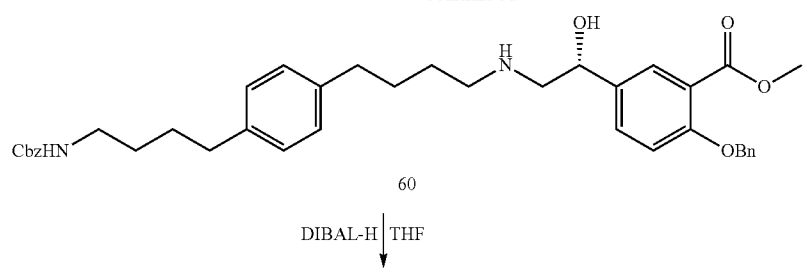
60
DIBAL-H | THF
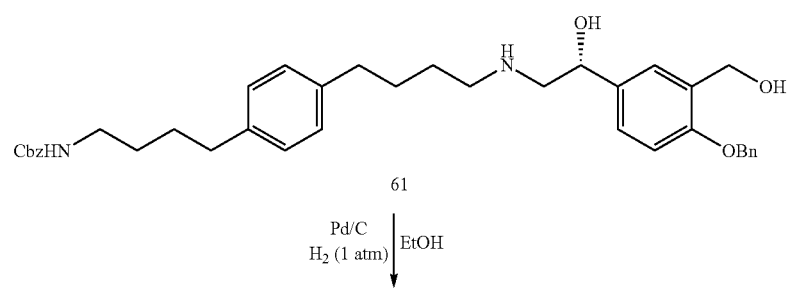
61
Pd/C
H₂ (1 atm) | EtOH
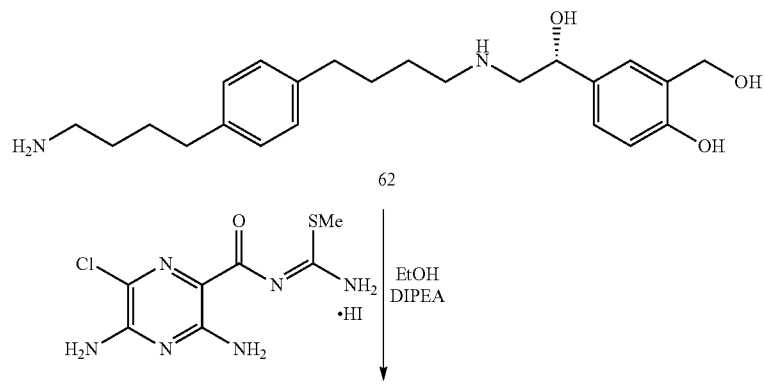
62
EtOH
DIPEA
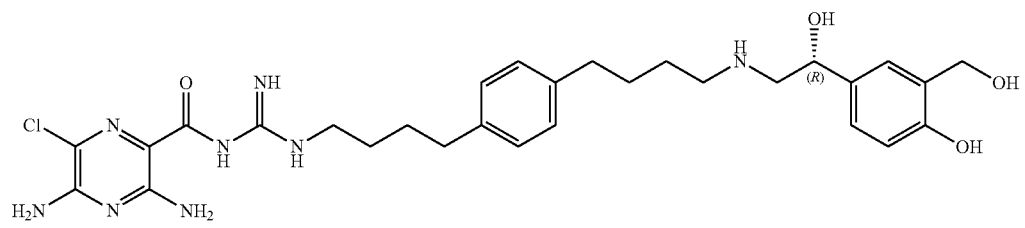
63

Scheme 9: Synthesis of Compound
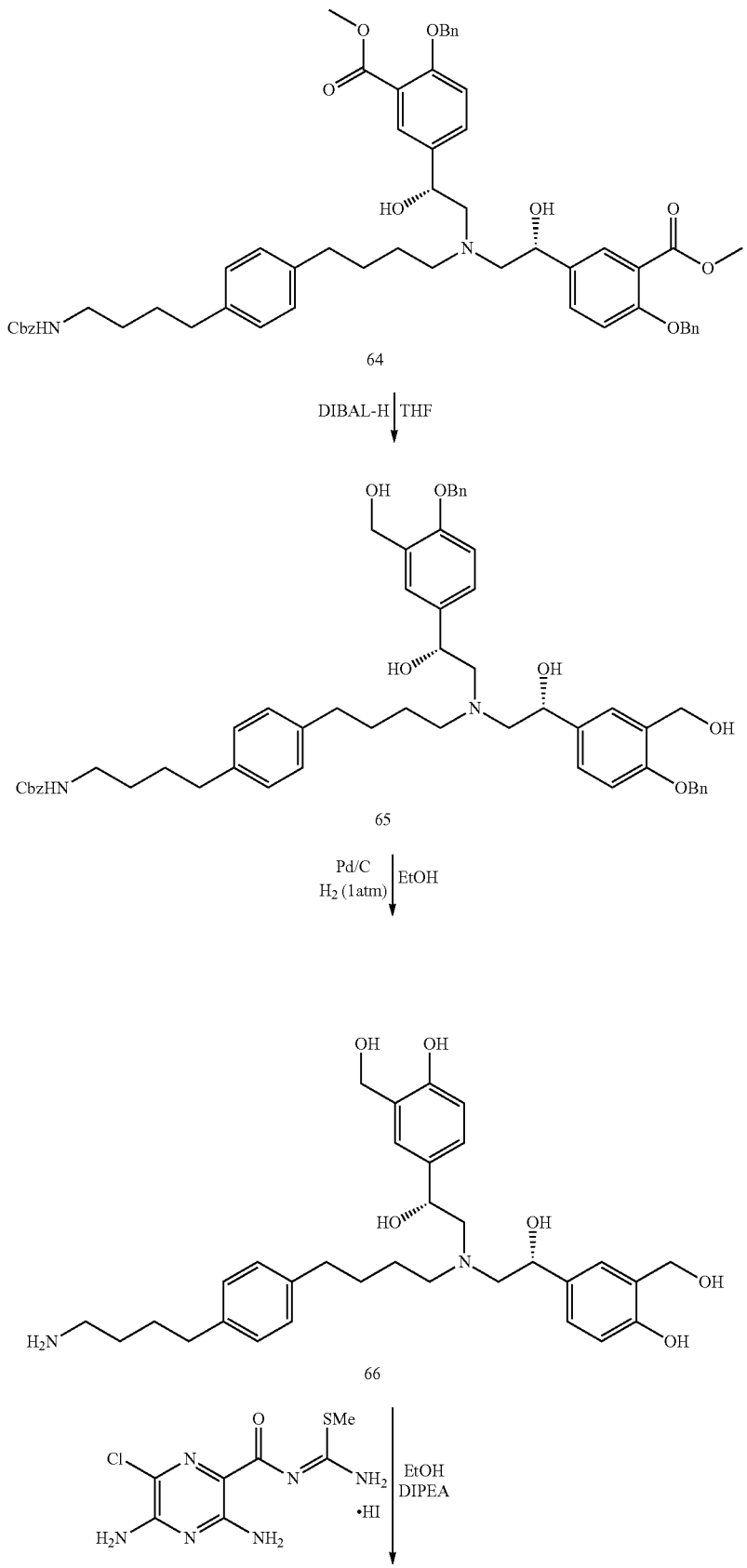

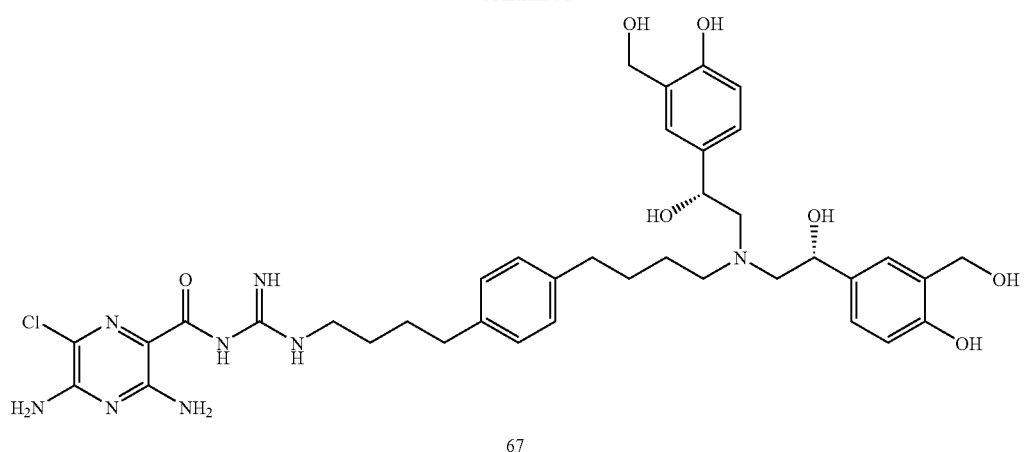
67
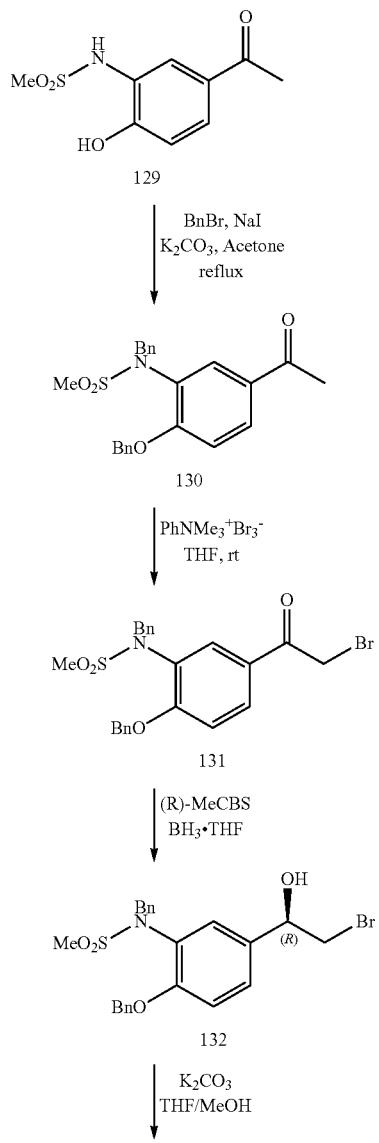
Scheme 10: Synthesis of 137

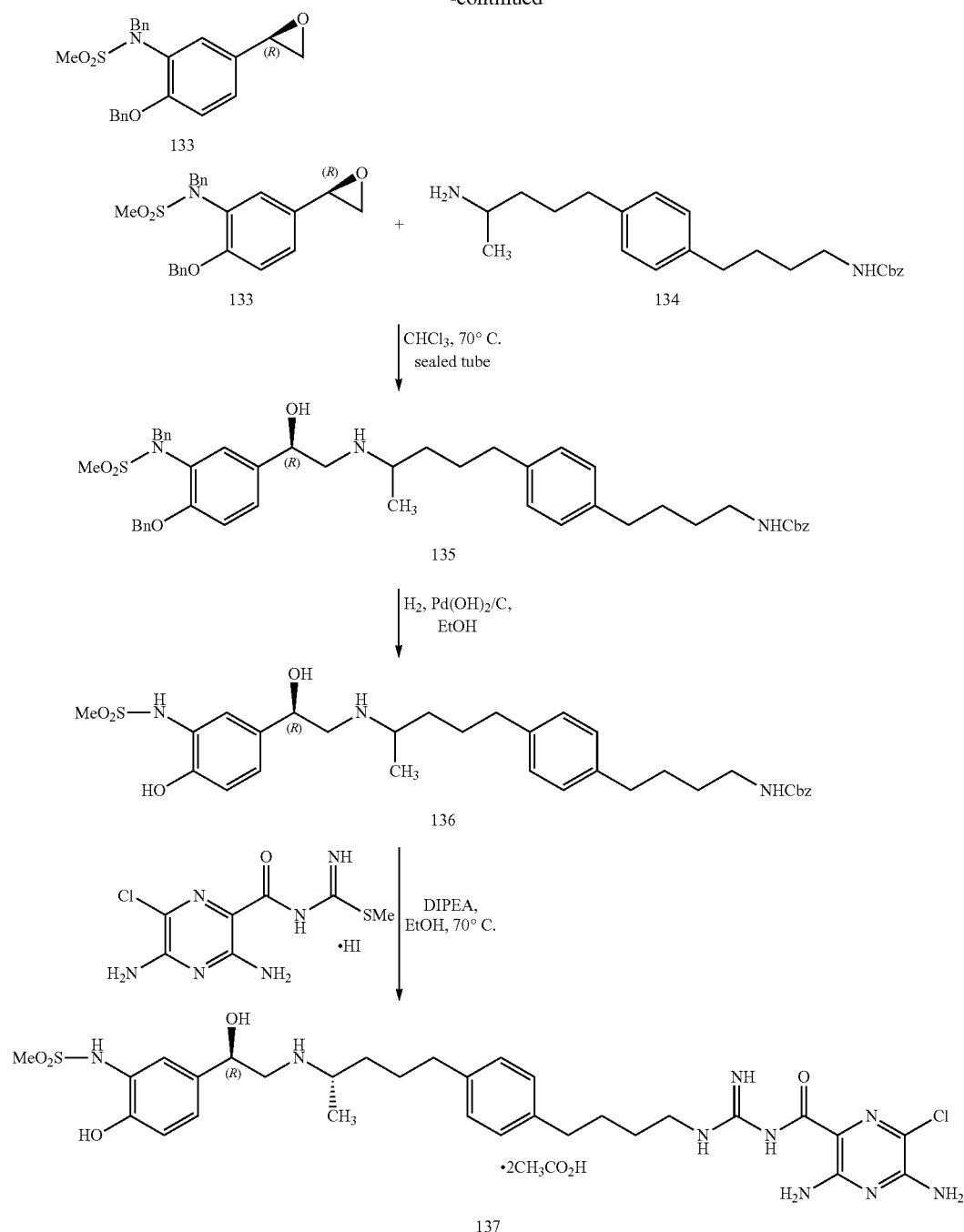
Scheme 11: Synthesis of 143
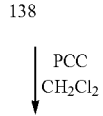

-continued
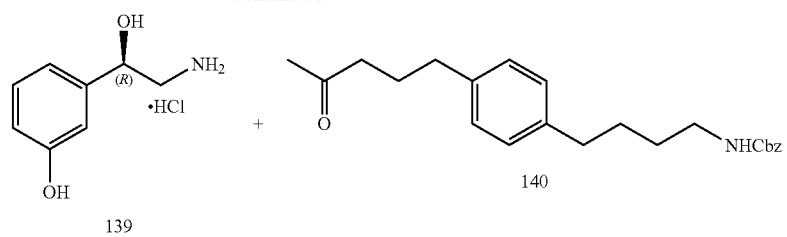
139 + 140
↓ NaBH(OAc)₃, MeOH
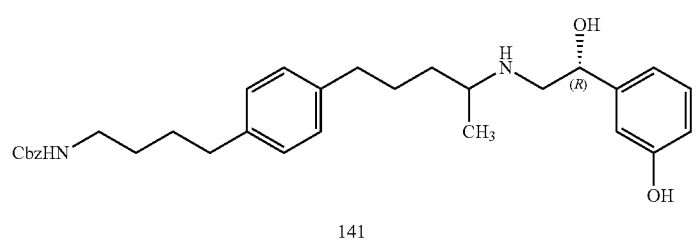
141
↓ H₂, Pd(OH)₂/C, EtOH
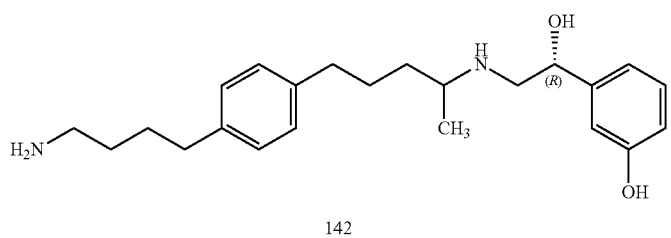
142
↓ DIPEA, EtOH, 75° C.
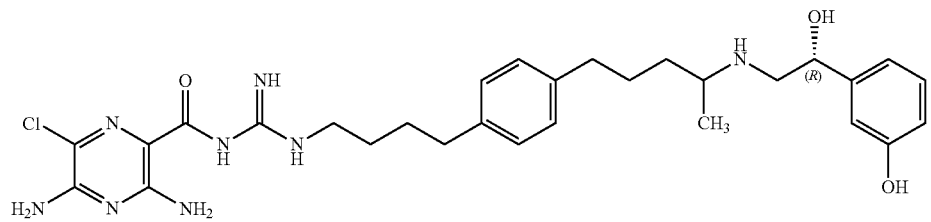
143

Scheme 12a: Synthesis of 147a
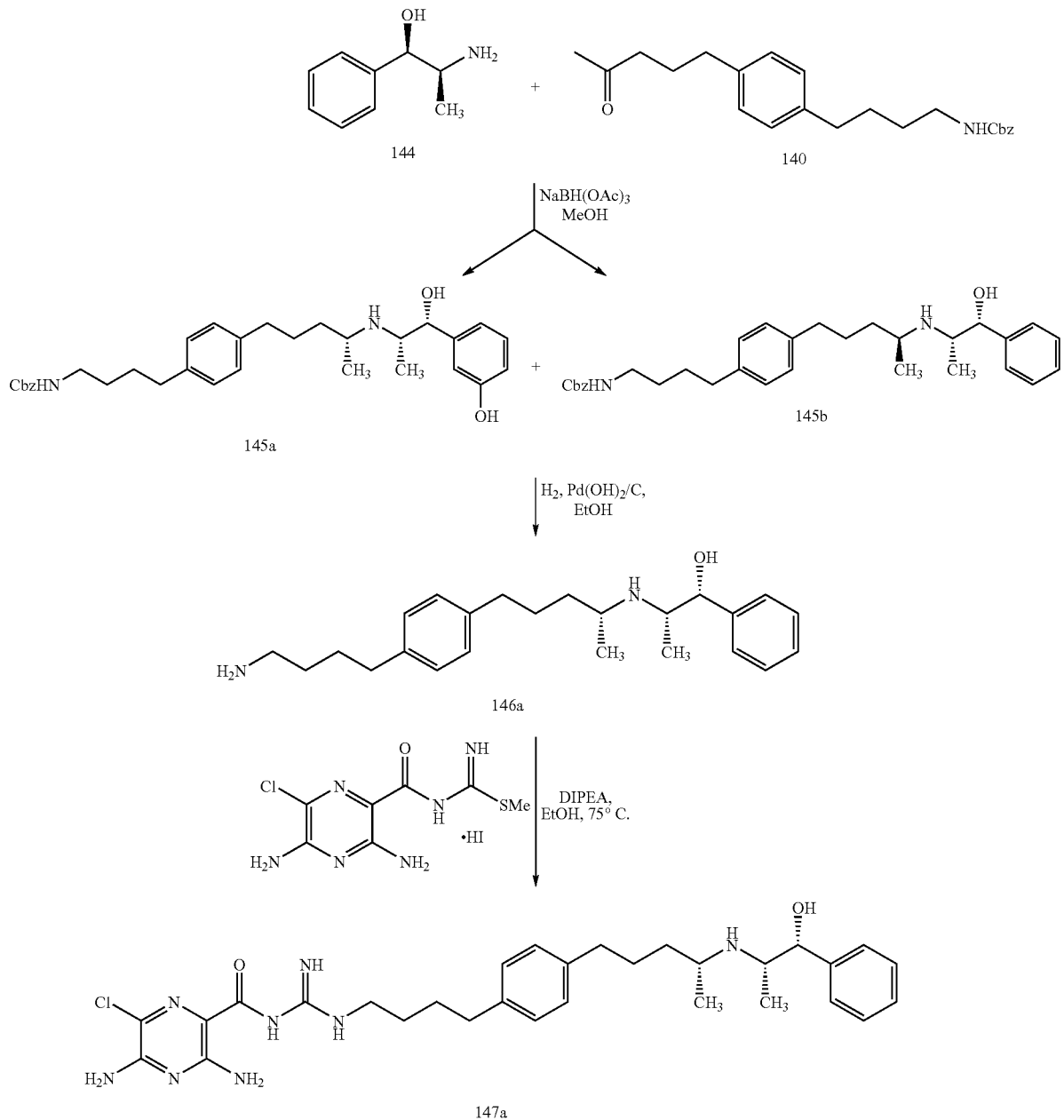
Scheme 12b: Synthesis of ALB 147b
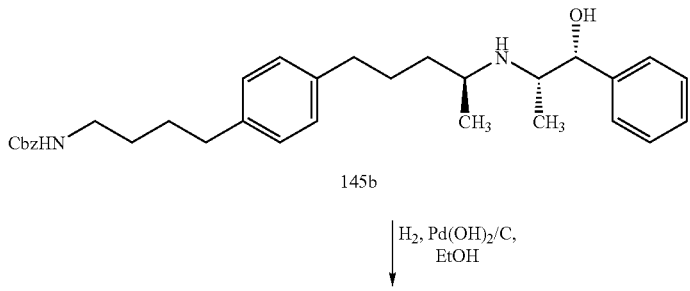

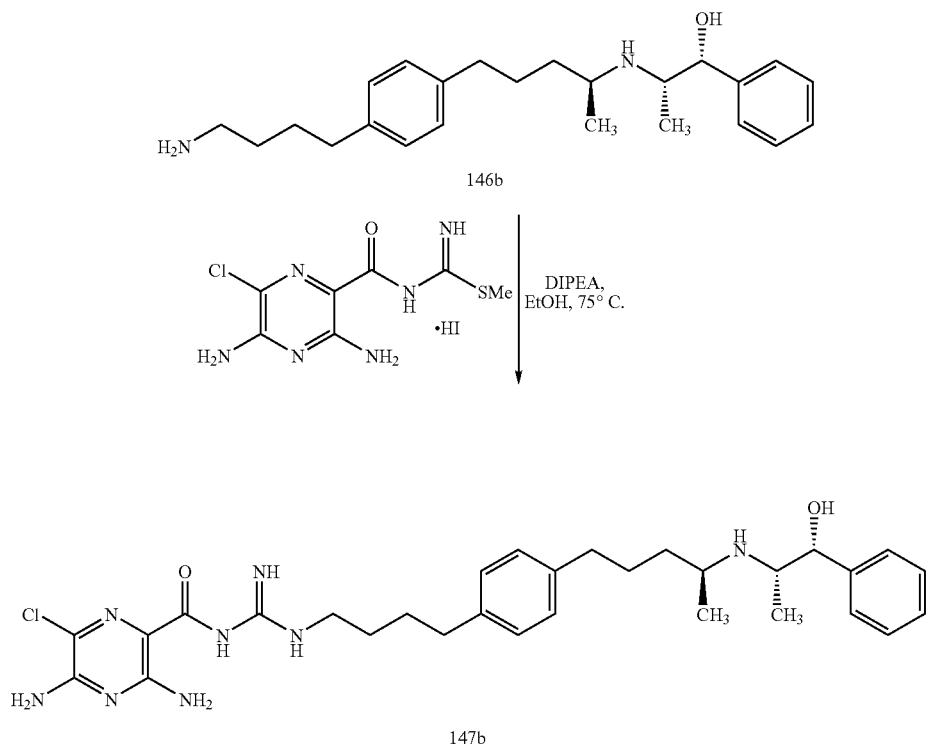
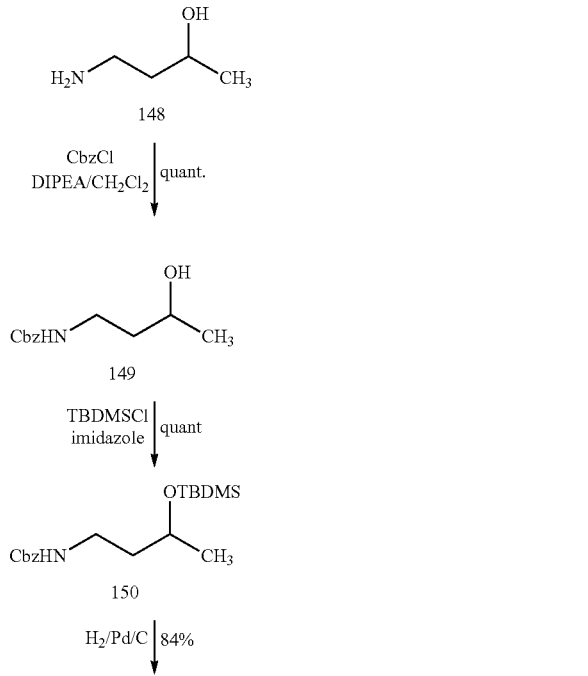
Scheme 13. Synthesis of 160

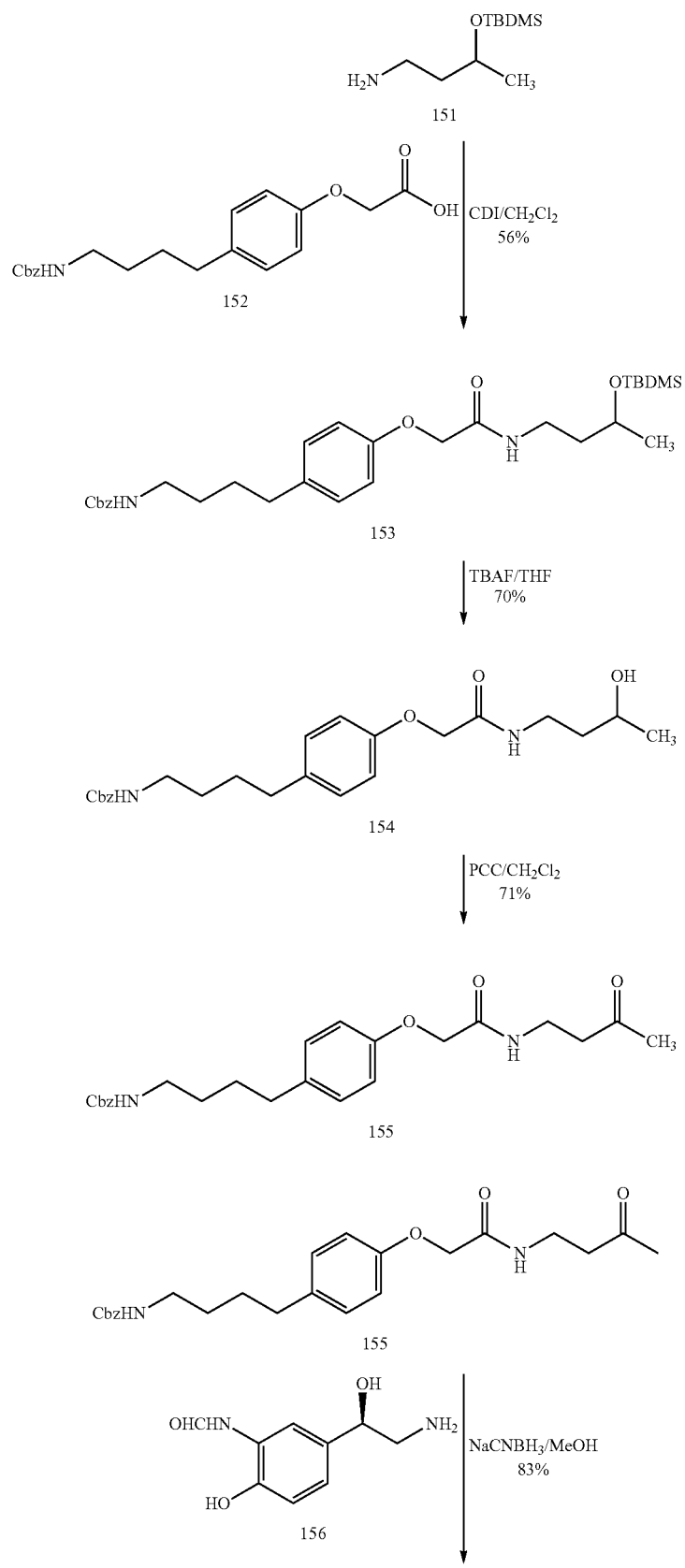

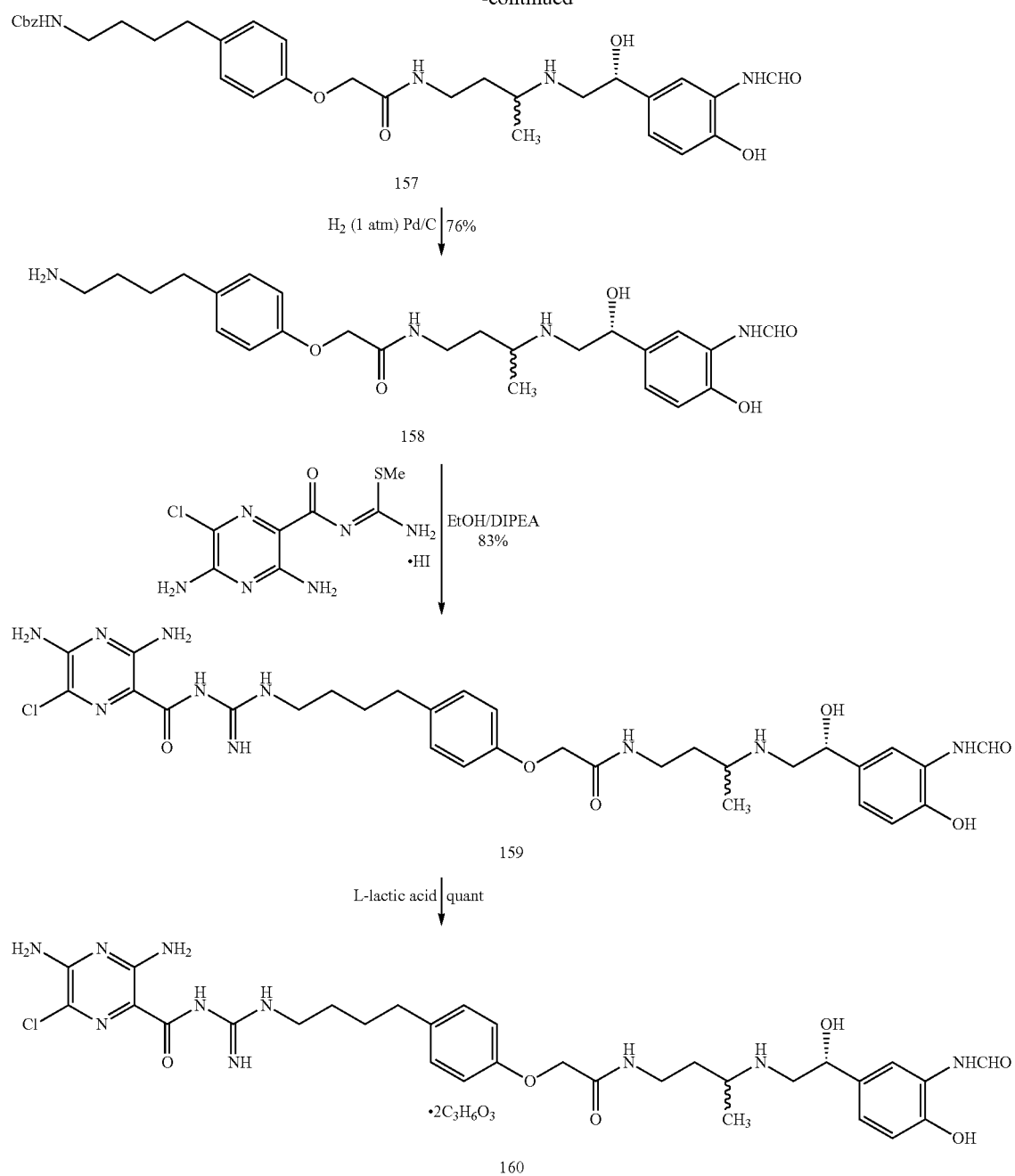
Scheme 14. Synthesis of ALB 175
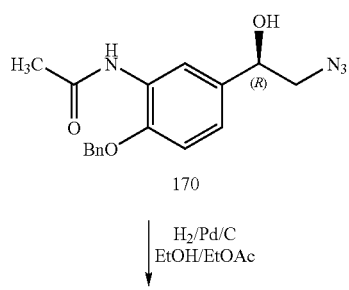

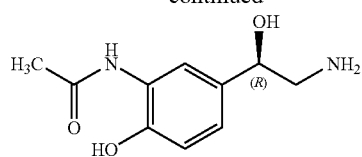
171
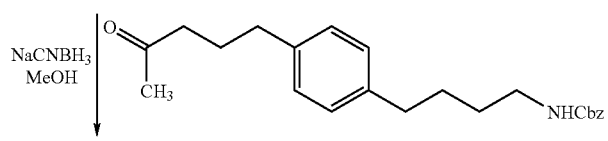
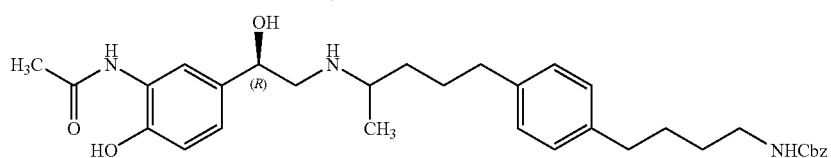
72
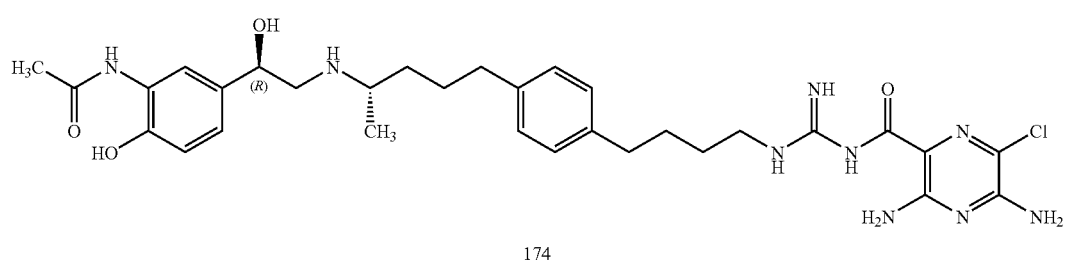
174
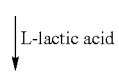
175

Several assays may be used to characterize the compounds of the present invention. Representative assays are described below.

1. In Vitro Measure of Epithelial Sodium Channel Block and Beta Agonist Activity To assess the potency of epithelial sodium channel block and beta agonist activity each compound was tested using two separate experimental procedures with similar methodology.

To assess epithelial sodium channel blocker potency the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, or dog airways are seeded onto porous 0.4 micrometer Transwell® Permeable Supports (Corning Inc. Acton, Mass.), cultured at air-liquid interface (ALI) conditions in hormonally defined media, and assayed for sodium transport activity ($I_{SC}$) while bathed in Krebs Bicarbonate Ringer (KBR) in Ussing chambers. All test drug additions are to the lumenal bath with approximately half-log dose additions (from $1 \times 10^{-11}$ M to $6 \times 10^{-5}$ M), and the cumulative change in $I_{SC}$ (decreases) recorded. All drugs are prepared in dimethyl sulfoxide as stock solutions at a concentration of approximately $1 \times 10^{-2}$ and stored at $-20°$ C. Six preparations are typically run in parallel; one preparation per run incorporates 552-02 as a positive control. Before the start of the concentration-effect relationship propranolol, a non-selective beta agonist blocker, was applied to the lumenal bath (10 µM) to inhibit the beta agonist component of the designer multiple ligand (DML). All data from the voltage clamps are collected via a computer face and analyzed off-line.

Concentration-effect relationships for all compounds are considered and analyzed Using GraphPad Prism version 3.00 for Windows, GraphPad Software, San Diego Calif. USA. $IC_{50}$ values, maximal effective concentrations, are calculated and compared to the 552-02 potency as a positive control.

To assess beta agonist activity the compounds of the present invention involves the determination of lumenal drug addition to promote airway epithelial anion currents measured under short circuit current ($I_{SC}$) using airway epithelial monolayers mounted in Ussing chambers. Cells obtained from freshly excised human, dog, or sheep airways are seeded onto porous 0.4 micron Transwell® Permeable Supports (Corning), cultured at air-liquid interface (ALI) conditions in hormonally defined media, and assayed for anion secretion ($I_{SC}$) while bathed in Krebs Bicarbonate Ringer (KBR) in Ussing chambers. All test drug additions are to the lumenal bath with approximately half-log dose additions (from $8 \times 10^{-10}$ M to $6.5 \times 10^{-5}$ M), and the cumulative change in $I_{SC}$ (excitation) recorded. All drugs are prepared in dimethyl sulfoxide as stock solutions at a concentration from $1 \times 10^{-1}$ to $1 \times 10^{-2}$ M and stored at $-20°$ C. Six preparations are typically run in parallel; one preparation per run incorporates either formoterol, salmeterol, or another well recognized beta agonists as a positive control depending on the analog incorporated in the compound being tested. Before the start of the concentration-effect relationship 552-02 a potent sodium channel blocker was applied to the apical surface (1 µM) to eliminate changes in Isc caused by sodium absorption. All data from the voltage clamps are collected via a computer interface and analyzed off-line.

Concentration-effect relationships for all compounds are considered and analyzed Using GraphPad Prism version 3.00 for Windows, GraphPad Software, San Diego Calif. USA. $EC_{50}$ values, maximal effective concentrations, are calculated and compared to either formoterol or salbutamol as the positive control.

2. In Vitro Assay of Compound Absorption and Biotransformation by Airway Epithelia Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays are performed to characterize any compound biotransformation (metabolism or conjugation) that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the Transwell® Permeable Supports (Corning), insert system. For most compounds, metabolism or conjugation (generation of new species) is tested for using high performance liquid chromatography (HPLC) to resolve chemical species and the endogenous fluorescence properties of these compounds to estimate the relative quantities of test compound and novel metabolites. For a typical assay, a test solution (1 mL KBR, containing 100 µM test compound) is placed on the epithelial lumenal surface. Sequential 5 to 600 µl samples are obtained from the lumenal and serosal compartments respectively for HPLC analysis of (1) the mass of test compound permeating from the lumenal to serosal bath and (2) the potential formation of metabolites from the parent compound. From the HPLC data, the rate of and/or formation of novel metabolite compounds on the lumenal surface and the appearance of test compound and/or novel metabolite in the basolateral solution is quantitated based on internal standards. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers with Beta Agonist Activity

Materials and Methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute$\theta$ system from Elution Solution (PO Box 5147, Charlottesville, Va. 22905) charged a 90 g silica gel cartridge (40M FSO-0110-040155, 32-63 μm) at 20 psi ($N_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: $H_2$ at 40 ml/min., Air at 400 ml/min. Carrier gas: Split Ratio 16:1, $N_2$ flow at 15 ml/min., $N_2$ velocity at 18 cm/sec. The temperature program is 70° C. for 0-3 min, 70-300° C. from 3-10 min, 300° C. from 10-15 min.

HPLC analysis was performed on a Gilson 322 Pump, detector UV/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

Synthesis of N-(5-{2-[4-(4-{4-[N'-(3,5-diamino-6-chloropyrazine-2-carbonyl)guanidino]butyl}phenyl)butylamino]-1-(R)-hydroxyethyl}-2-hydroxyphenyl)formamide (12) (Scheme 1)

1-(4-Benzyloxy-3-nitrophenyl)ethanone (2)

A mixture of 1-(4-hydroxy-3-nitrophenyl)ethanone (5.92 g, 32.70 mmol), sodium iodide (4.90 g, 32.70 mmol), potassium carbonate (13.55 g, 98.00 mmol), and benzyl bromide (5.04 mL, 42.50 mmol) in acetone (120 mL) was stirred under reflux for 66 h. After removal of solvent by rotary evaporation, the resulting residue was diluted with dichloromethane and insoluble inorganics were filtered off. The filtrate was concentrated in vacuo and the resulting residue was purified by flash silica gel column chromatography eluting with dichloromethane to give benzyl ether 2 as a white solid (8.24 g, 93%): $^1$H NMR (500 MHz, CDCl$_3$) δ 2.60 (s, 3H), 5.32 (s, 2H), 7.18 (d, 1H), 7.41 (m, 5H), 8.12 (dd, 1H), 8.44 (d, 1H).

1-(4-Benzyloxy-3-nitrophenyl)-2-bromoethanone (3)

Phenyltrimethylammonium tribromide (1.46 g, 3.90 mmol) was added to a solution of 1-(4-benzyloxy-3-nitrophenyl)ethanone (2) (1.04 g, 3.82 mmol) in anhydrous THF (15 mL) in three portions. The reaction mixture was stirred at rt for 12 h. Then an aqueous sodium bicarbonate solution (5%, 10 mL) and an aqueous sodium thiosulfate solution (10%, 5 mL) were added. The mixture was extracted with dichloromethane, and combined organics were concentrated by rotary evaporation. The resulting residue was purified by Biotage silica gel column chromatography eluting with dichloromethane to give bromo ketone 3 as a white solid (1.08 g, 81% yield): $^1$H NMR (500 MHz, CDCl$_3$) δ 4.49 (s, 3H), 5.35 (s, 2H), 7.21 (d, 1H), 7.40 (m, 5H), 8.15 (dd, 1H), 8.49 (d, 1H).

1-(4-Benzyloxy-3-nitrophenyl)-2-bromo-1-(R)-ethanol (4)

A solution of BH$_3$.THF in THF (1 M, 3.70 mL, 3.70 mmol) was added to a solution of 1-(4-benzyloxy-3-nitrophenyl)-2-bromoethanone (3) (1.08 g, 3.08 mmol) and R-methyl-CBS-oxazoborolidine (1 M in toluene, 0.61 mL, 0.61 mmol) in anhydrous THF (15 mL). The resulting reaction mixture was stirred at rt for 16 h. Methanol (5 mL) was slowly added to quench the reaction. After removal of solvent by rotary evaporation, the resulting residue was purified by Biotage silica gel column chromatography eluting with dichloromethane to give the desired bromo alcohol 4 as a yellow, viscous oil (0.72 g, 66%): $^1$H NMR (500 MHz, CDCl$_3$) δ 2.82 (d, 1H), 3.48 (dd, 1H), 3.59 (dd, 1H), 4.89 (m, 1H), 5.21 (s, 2H), (d, 1H), 7.39 (m, 5H), 7.50 (dd, 1H), 7.87 (d, 1H).

N-[2-Benzyloxy-5-(2-bromo-1-(R)-hydroxyethyl)phenyl]formamide (5)

A Parr hydrogenator was charged with PtO$_2$ and 1-(4-benzyloxy-3-nitro-phenyl)-2-bromo-1-(R)-ethanol (4) (0.72

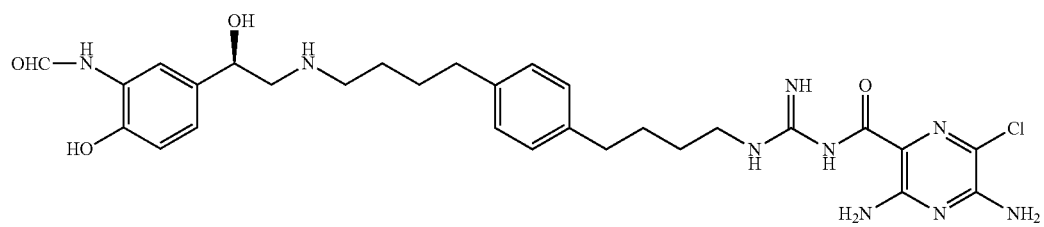

12 g, 2.04 mmol) dissolved in a mixed solvent of THF (8 mL) and toluene (8 mL). The mixture was hydrogenated at 55 psi at rt for 16 h. Then a mixture of formic acid (0.13 mL, 3.45 mmol) and acetic anhydride (0.22 mL, 2.33 mmol) was added and stirring was continued at rt for 66 h. The catalyst was filtered through a Celite pad and the filtrate was concentrated by rotary evaporation. The resulting residue was purified by Biotage silica gel column chromatography eluting with ethyl acetate/dichloromethane (gradient 0% to 10%) to give the desired formamide 5 as a white solid (0.45 g, 63%): $^1$H NMR (300 MHz, CDCl$_3$) δ 2.95 (s, 1H), 3.52 (m, 1H), 3.60 (m, 1H), 4.85 (m, 1H), 5.08 (s, 2H), 6.96 (d, 1H), 7.13 (dd, 1H), 7.39 (m, 5H), 7.88 (br, 1H), 8.37 (dd, 1H).

N-(2-Benzyloxy-5-(R)-oxiranylphenyl)formamide (6)

Potassium carbonate (019 g, 1.37 mmol) was added to a solution of N-[2-benzyloxy-5-(2-bromo-1-(R)-hydroxyethyl)phenyl]formamide (5) (0.37 g, 1.05 mmol) dissolved in a mixed solvent of THF (3 mL) and methanol (5 mL). The reaction mixture was stirred at rt for 3 h. After removal of solvents by rotary evaporation, the residue was taken up in dichloromethane and suction filtered to remove inorganics. The filtrate was concentrated in vacuo and further co-evaporated with toluene and dried under high vacuum. The desired epoxide 6 was obtained as a white solid (0.21 g, 72%) and used directly for next step without purification: $^1$H NMR (500 MHz, CDCl$_3$) δ 2.78 (dd, 1H), 3.07 (dd, 1H), 3.79 (dd, 1H), 5.06 (s, 2H), 6.92 (d, 1H), 7.15 (m, 1H), 7.38 (m, 5H), 7.90 (s, 1H), 8.36 (s, 1H).

[4-(4-{4-[2-(4-Benzyloxy-3-formylaminophenyl)-2-(R)-hydroxyethylamino]-butyl}phenyl)butyl]carbamic acid benzyl ester (8)

A mixture of N-(2-benzyloxy-5-(R)-oxiranylphenyl)formamide (6) (0.21 g, 0.76 mmol) and {4-[4-(4-aminobutyl)phenyl]butyl}carbamic acid benzyl ester (7) (0.40 g, 1.14 mmol. See Scheme 8 for its synthesis.) in iPrOH (6 mL) was stirred under reflux for 16 h. The solvent was then removed by rotary evaporation and the resulting residue was purified by Biotage silica gel column chromatography eluting with methanol/dichloromethane (gradient, 0 to 7%), and then by preparative TLC eluting with dichloromethane/methanol/concentrated ammonium hydroxide (200:10:1, v/v). The desired adduct 8 was isolated as a solid (0.14 g, 30%): $^1$H NMR (500 MHz, CDCl$_3$) δ 1.50 (m, 2H), 1.62 (m, 6H), 2.55 (m, 4H), 2.76 (m, 3H), 2.94 (dd, 1H), 3.18 (m, 2H), 3.96 (br, 2H), 4.82 (m, 2H), 5.06 (m, 4H), 6.92 (d, 1H), 7.05 (m, 4H), 7.13 (dd, 1H), 7.34 (m, 5H), 7.39 (m, 5H), 7.86 (br, 1H), 8.34 (dd, 1H); m/z (ESI) 624 $[C_{38}H_{45}N_3O_5+H]^+$. In addition, two by-products were obtained. The isomeric adduct 9 (78 mg, 16%): $^1$H NMR (500 MHz, CDCl$_3$) δ 1.58 (m, 8H), 2.52 (m, 8H), 3.19 (m, 2H), 3.53 (dd, 1H), 3.69 (m, 2H), 4.78 (br, 1H), 5.08 (m, 4H), 6.95 (d, 1H), 7.05 (m, 5H), 7.32 (m, 5H), 7.40 (m, 5H), 7.82 (br, 1H), 8.35 (d, 1H); m/z (ESI) 624 $[C_{38}H_{45}N_3O_5+H]^+$. And the bis-adduct 10 (0.17 g, 24%): $^1$H NMR (500 MHz, CDCl$_3$) δ 1.55 (m, 8H), 2.60 (m, 10H), 3.16 (m, 2H), 4.62 (m, 2H), 4.82 (br, 1H), 5.05 (m, 6H), 6.90 (m, 2H), 7.08 (m, 6H), 7.35 (m, 15H), 7.80 (m, 2H), 8.31 (m, 2H); m/z (ESI) 893 $[C_{54}H_{60}N_4O_8+H]^+$.

N-[5-(2-{4-[4-(4-Aminobutyl)phenyl]butylamino}-1-(R)-hydroxyethyl)-2-hydroxyphenyl]formamide diacetic acid salt (11)

A mixture of [4-(4-{4-[2-(4-benzyloxy-3-formylaminophenyl)-2-(R)-hydroxyethylamino]butyl}phenyl)butyl]carbamic acid benzyl ester (8) (84 mg, 0.14 mmol), palladium dihydroxide (28 mg, 10% Pd(OH)$_2$ on carbon, 50% wet), three drops of acetic acid, methanol (5 mL), and dichloromethane (5 mL) was stirred at rt for 16 h under atmospheric hydrogen pressure. The catalyst was filtered through a Celite pad and the filtrate was concentrated by rotary evaporation and further dried under high vacuum to give the desired amine diacetic acid salt 11 as a yellow solid (69 mg, 99%): $^1$H NMR (500 MHz, CD$_3$OD) δ 1.68 (m, 8H), 1.93 (s, 6H), 2.63 (m, 4H), 2.91 (m, 2H), 3.08 (m, 4H), 4.83 (m, 1H), 6.88 (d, 1H), 7.05 (d, 1H), 7.11 (s, 4H), 8.10 (s, 1H), 8.30 (s, 1H); m/z (ESI) 400 $[C_{23}H_{33}N_3O_3+H]^+$.

N-(5-{2-[4-(4-{4-[N'-3,5-Diamino-6-chloropyrazine-2-carbonyl)guanidino]-butyl}phenyl)butylamino]-1-(R)-hydroxyethyl}-2-hydroxyphenyl)formamide (12)

Diisopropylethylamine (0.13 mL, 0.72 mmol) was added to a solution of N-[5-(2-{4-[4-(4-aminobutyl)phenyl]butylamino}-1-(R)-hydroxyethyl)-2-hydroxyphenyl]formamide diacetic acid salt (11) (65 mg, 0.13 mmol) in absolute ethanol (5 mL). The mixture was stirred at 70° C. (oil bath) for 10 min, after which 1-(3,5-diamino-6-chloropyrazine-2-carbonyl)-2-methylisothiourea hydriodide (53 mg, 0.14 mmol) was added in two portions over 45 min. The reaction mixture was stirred at that temperature for 3 h and cooled to rt. Solvent was removed by rotary evaporation. The residue was purified by Biotage silica gel column chromatography (A=dichloromethane, B=10% concentrated aqueous ammonium hydroxide in methanol, gradient B/A 1% to 15%), and further purified by semi-preparative HPLC eluting with a gradient acetonitrile and water, each containing 0.05% concentrated ammonium hydroxide, to give N-(5-{2-[4-(4-{4-[N'-(3,5-diamino-6-chloropyrazine-2-carbonyl)guanidino]butyl}phenyl)butylamino]-1-(R)-hydroxyethyl}-2-hydroxyphenyl)formamide (12) as a greenish yellow solid (35 mg, 46%): $^1$H NMR (500 MHz, DMSO-d$_6$) δ 1.50 (m, 8H), 2.51 (m, 4H), 3.15 (m, 6H), 4.42 (m, 1H), 5.00 (br, 1H), 6.58 (br, 2H), 6.72 (m, 1H), 6.80 (m, 1H), 7.08 (m, 4H), 8.00 (s, 1H), 8.25 (s, 1H); m/z (ESI) 612 $[C_{29}H_{38}ClN_9O_4+H]^+$; $[\alpha]_D^{25}$ −3.3° (c 0.15, MeOH); mp 138-140° C.

Example 2

Synthesis of N-{4-[4-(4-{bis-[2-(R)-hydroxy-2-(4-hydroxy-3-formylaminophenyl)-ethyl]amino}butyl)phenyl]butyl}-N'-(3,5-diamino-6-chloropyrazine-2-carbonyl)-guanidine diacetic acid salt (14) (Scheme 2)

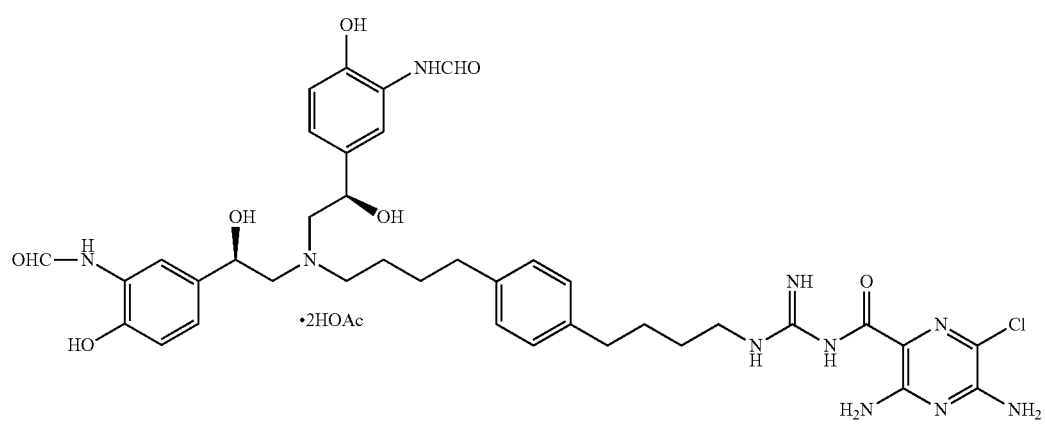

14

{4-[4-(4-{bis-[2-(4-hydroxy-3-formylaminophenyl)-2-(R)-hydroxyethyl]amino}-butyl)phenyl] butyl}amine diacetic acid salt (13)

A mixture of {4-[4-(4-{bis-[2-(4-benzyloxy-3-formylaminophenyl)-2-(R)-hydroxyethyl]-amino}butyl)phenyl] butyl}carbamic acid benzyl ester (10) (0.17 g, 0.19 mmol), palladium dihydroxide (50 mg, 10% Pd(OH)$_2$ on carbon, 50% wet), eight drops of acetic acid, methanol (10 mL), and dichloromethane (5 mL) was stirred at rt for 18 h under atmospheric hydrogen pressure. The catalyst was filtered through a Celite pad and the filtrate was concentrated by rotary evaporation and further dried under high vacuum to give the desired amine diacetic acid salt 13 as a white solid (0.10 mg, 98%); m/z (ESI) 579 [C$_{32}$H$_{42}$N$_4$O$_6$+H]$^+$.

N-{4-[4-(4-{Bis-[2-(R)-hydroxy-2-(4-hydroxy-3-formylaminophenyl)-ethyl]amino}-butyl)phenyl] butyl}-N'-(3,5-diamino-6-chloropyrazine-2-carbonyl)guanidine diacetic acid salt (14)

Diisopropylethylamine (0.16 mL, 0.92 mmol) was added to a solution of {4-[4-(4-{bis-[2-(4-hydroxy-3-formylaminophenyl)-2-(R)-hydroxyethyl]amino}-butyl)phenyl] butyl}amine diacetic acid salt (13) (129 mg, 019 mmol) in absolute ethanol (4 mL). The mixture was stirred at 70° C. (oil bath) for 10 min, after which 1-(3,5-diamino-6-chloropyrazine-2-carbonyl)-2-methylisothiourea hydriodide (79 mg, 0.20 mmol) was added in one portion. The reaction mixture was stirred at that temperature for 3 h and cooled to rt. The solvent was removed by rotary evaporation. The residue was purified by Biotage silica gel column chromatography (A=dichloromethane, B=10% concentrated aqueous ammonium hydroxide in methanol, gradient B/A 1% to 25%) to give the desired adduct 14 as a greenish yellow solid (44 mg, 26%): $^1$H NMR (500 MHz, DMSO-d$_6$) δ 1.50 (m, 8H), 1.98 (s, 6H), 2.58 (m, 4H), 3.20 (m, 8H), 4.45 (m, 2H), 6.60 (br, 2H), 6.80 (m, 4H), 7.08 (m, 4H), 8.00 (s, 2H), 8.28 (s, 2H), 9.56 (br, 2H); m/z (ESI) 791 [C$_{38}$H$_{47}$ClN$_{10}$O$_7$+H]$^+$; [α]$_D^{25}$ −4.0° (c 0.35, MeOH); mp 128-130° C.

Example 3

Synthesis of N-(5-{2-[2-(4-{4-[N-(3,5-diamino-6-chloropyrazine-2-carbonyl)guanidine] butyl}phenoxy)ethylamino]-1-(R)-hydroxylethyl}-2-hydroxyphenyl)-formamide (19) (Scheme 3)

{4-[4-(2-Benzylaminoethoxy)phenyl]butyl}carbamic acid benzyl ester (16)

Benzyaldehyde (0.74 ml, 7.31 mmol) was added to a solution of 4-[4-(2-aminoethoxy)phenyl]butylcarbamic acid benzyl ester (15) (5.00 g (~50% purity by NMR), 7.30 mmol) dissolved in anhydrous dichloroethane (50 mL). The resulting solution was stirred at ambient temperature for 7 h. Sodium triacetoxyborohydride (4.10 g, 19.35 mmol) was added slowly and the reduction continued for 60 h. The reaction was quenched with aqueous sodium bicarbonate (50 mL) and then extracted with ethyl acetate (3×25 mL). The combined organic extracts were washed sequentially with water and brine, and dried over anhydrous sodium sulfate. A white solid precipitated out during the drying and collected by dissolving it in dichloromethane and then filtering off the solid sodium sulfate. The filtrate was concentrated and dried under vacuum to give 16 (1.35 g, 43%) as a white solid: $^1$H NMR (500 MHz, CDCl$_3$) δ 1.45-1.62 (m, 4H), 2.54 (t, 2H), 3.07-3.22 (m, 4H), 3.88 (s, 2H), 4.10 (t, 2H), 4.73 (br, 1H), 5.09 (s, 2H), 6.79 (d, 2H), 7.04 (d, 2H), 7.28-7.39 (m, 10H); m/z (ESI) 433 [C$_{27}$H$_{32}$N$_2$O$_3$+H]$^+$.

{4-[4-(2-{Benzyl-[2-(4-benzyloxy-3-formylaminophenyl)-2-(R)-hydroxyethyl]amino}-ethoxy)phenyl]butyl}carbamic acid benzyl ester (17)

Benzylamine 16 (619 mg, 1.43 mmol) was added to a suspension of bromoalcohol 5 (500 mg, 1.43 mmol) and K$_2$CO$_3$ (495 mg, 3.58 mmol) methanol (10 mL) and tetrahydrofuran (5 mL). The suspension was stirred at ambient temperature for 15 h, then heated to 55° C. for 75 h. The solid was vacuum filtered and the filtrate was concentrated under vacuum. The resulting oil was subjected to column chromatography eluting with 5-50% ethyl acetate in hexanes to afford the desired product 17 (508 mg, 5%) as an off-white solid: $^1$H NMR (500 MHz, CDCl$_3$) δ 1.45-1.62 (m, 4H), 2.54 (t, 2H), 2.65-2.71 (m, 1H), 3.14-3.23 (m, 3H), 3.58-3.74 (m, 1H), 3.88-4.09 (m, 3H), 4.71 (br, 2H), 5.04-5.21 (m, 4H), 6.79-7.25 (m, 6H), 7.34-7.52 (m, 16H), 7.65-7.87 (m, 1H), 8.32-8.49 (m, 1H); m/z, (ESI) 702 [C$_{43}$H$_{47}$N$_3$O$_6$+H]$^+$.

N-[5-(2-{2-[4-(4-Aminobutyl)phenoxy]ethylamino}-1-(R)-hydroxyethyl)-2-hydroxyphenyl]formamide (18)

α-Aminoalcohol 17 (500 mg, 0.71 mmol) was dissolved in ethanol (20 mL). Following the standard hydrogenation pro-

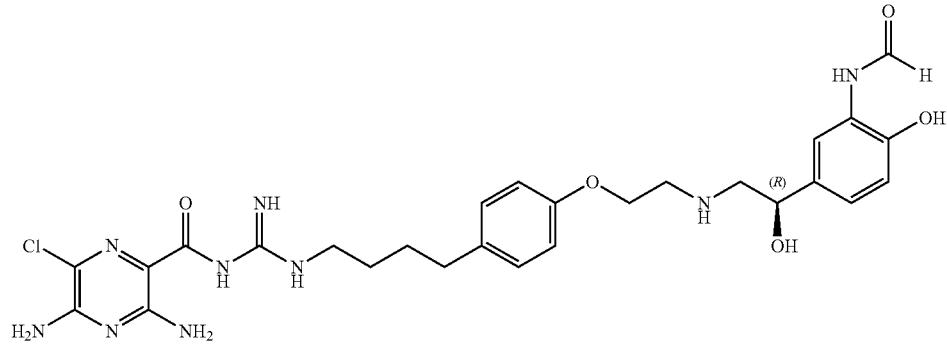

cedure, palladium dihydroxide (20% on carbon, 50% wet) was added. The reaction mixture was stirred for 15 h at ambient temperature under atmospheric H$_2$ pressure. The catalyst was removed by filtration through diatomaceous earth and the filtrate was concentrated to a yellow solid. Purification of the crude solid by column chromatography eluting with 10-30% (20% concentrated ammonium hydroxide in methanol) in dichloromethane gave 18 (146 mg, 53%) as a yellow solid: $^1$H NMR (300 MHz, CD$_3$OD) δ 1.29-1.72 (m, 5H), 1.93 (s, 3H), 2.58 (t, 2H), 2.71-2.90 (m, 4H), 2.99 (t, 2H), 4.05 (t, 2H), 4.66-4.72 (m, 1H), 6.78-6.85 (m, 3H), 6.97-7.16 (m, 3H), 7.82-8.04 (m, 1H), 8.29 (s, 1H).

N-(5-{2-[2-(4-{4-[N'-(3,5-Diamino-6-chloropyrazine-2-carbonyl)guanidine]butyl}-phenoxy)ethylamino]-1-(R)-hydroxyethyl}-2-hydroxyphenyl)formamide (19)

Diisopropylethylamine (0.10 mL, 0.57 mmol) and 1-(3,5-diamino-6-chloropyrazine-2-carbonyl)-2-methylisothiourea hydriodide (146 mg, 0.38 mmol) were sequentially added to a solution of amine 18 (146 mg, 0.38 mmol) in ethanol (5 mL). The reaction mixture was heated to 75° C. for 5 h after which time it was cooled and concentrated under vacuum. The resulting residue was purified by column chromatography eluting with 1-30% (20:80 concentrated ammonium hydroxide/methanol) in dichloromethane affording the desired product 19 (100 mg, 44%) as a yellow solid: $^1$H NMR (500 MHz, DMSO-d$_6$) δ 1.46-1.64 (m, 4H), 2.51-2.58 (m, 2H), 2.66 (t, 2H), 2.90 (t, 2H), 3.16 (br, 2H), 3.91-4.11 (m, 4H), 4.51 (t, 1H), 5.18 (br, 1H), 6.75-6.99 (m, 7H), 7.05-7.09 (m, 2H), 8.02-8.06 (m, 1H), 8.19 (br, 1H), 9.53 (br, 1H); mp 120-124° C. (dec); m/z (ESI) 600 [C$_{27}$H$_{34}$ClN$_9$O$_5$+H]$^+$; [α]$^{25}_D$ −7.5° (c 0.35, CH$_3$OH).

Example 4

Synthesis of N-(5-{2-[4-(4-{4-[N'-(3,5-diamino-6-chloropyrazine-2-carbonyl)-guanidino]butyl}phenyl)-1-methylbutylamino]-1-(R)-hydroxyethyl}-2-hydroxyphenyl)formamide (30) (Scheme 4)

2-(1-Methylbut-3-ynyl)isoindole-1,3-dione (22)

A solution composed of phthalimide 21 (13.12 g, 89.16 mmol), PPh$_3$ (23.38 g, 89.16 mmol) and THF (anhydrous, 250 mL) was stirred at room temperature for 1 h. To the solution was added 4-hydroxypentyne 20 (5.00 g, 59.44 mmol) in one portion, followed by a solution of DIAD (17.27 mL, 89.16 mmol) dissolved in THF (anhydrous, 50 mL), which was added dropwise over 2 h. After the addition of DIAD temperature was raised to 60° C. and the reaction mixture was further stirred at that temperature overnight. The mixture was cooled to room temperature and concentrated under vacuum. To the residue was added dichloromethane (100 mL). The formed precipitate was vacuum filtered and washed with dichloromethane. The filtrate and washings were combined and concentrated under vacuum. The residue was subjected to column chromatography eluting with a mixture of ethyl acetate and hexanes (0-75%, v/v) to afford the desired product 22 (4.47 g, 35%) as an off-white solid: $^1$H NMR (300 MHz, CDCl$_3$) δ 1.54 (d, 3H), 1.92 (s, 1H), 2.68 (m, 1H), 2.96 (m, 1H), 4.59 (m, 1H), 7.72 (dd, 2H), 7.85 (dd, 3.0 Hz, 1H); (ESI) 214 [C$_{13}$H$_{11}$NO$_2$+H]$^+$.

(4-{4-[4-(1,3-Dioxo-1,3-dihydroisoindol-2-yl)pent-1-ynyl]phenyl}but-3-ynyl)-carbamic acid benzyl ester (24)

A 100 mL, round-bottom flask containing a mixture of [4-(4-iodophenyl)but-3-ynyl]carbamic acid benzyl ester 23 (2.33 g, 5.75 mmol), CuI (0.22 g, 1.15 mmol), Et$_3$N (10 mL) and THF (anhydrous, 15 mL) was vacuumed and refilled with nitrogen. The procedure was repeated three more time. To the suspension was added Pd(PPh$_3$)$_2$Cl$_2$ (0.40 g, 0.58 mmol) in one portion, followed by a solution of compound 22 (1.35 g, 6.32 mmol) dissolved in THF (anhydrous, 10 mL), which was added dropwise over 2 h. The stirring was continued overnight. The reaction mixture was concentrated under vacuum. The residue was subjected to column chromatography eluting with a mixture of ethyl acetate (0-25%) and hexanes to afford the desired product 24 (2.60 g, 92%) as an off-yellow solid. $^1$H NMR (500 MHz, CDCl$_3$) δ 1.71 (d, 3H), 2.61 (t, 2H), 2.92 (m, 1H), 3.14 (m, 1H), 3.43 (t, 2H), 4.67 (m, 1H), 5.07 (br, 1H), 5.11 (s, 2H), 7.12-7.33 (m, 9H), 7.71 (dd, 2H), 7.92 (dd, 1H); m/z (ESI) 491 [C$_{31}$H$_{26}$N$_2$O$_4$+H]$^+$.

(4-{4-[4-(1,3-Dioxo-1,3-dihydroisoindol-2-yl)pentyl]phenyl}butyl)carbamic acid benzyl ester (25)

A solution containing compound 24 (2.53 g, 5.15 mmol) dissolved in THF (100 mL) was vacuumed and refilled with nitrogen. The procedure was repeated five times. To the solution was added palladium catalyst (0.5 g, 10% Pd on carbon, 50% wet). The flask was then pressurized with hydrogen gas to 45 psi. The mixture was then shaken overnight at room

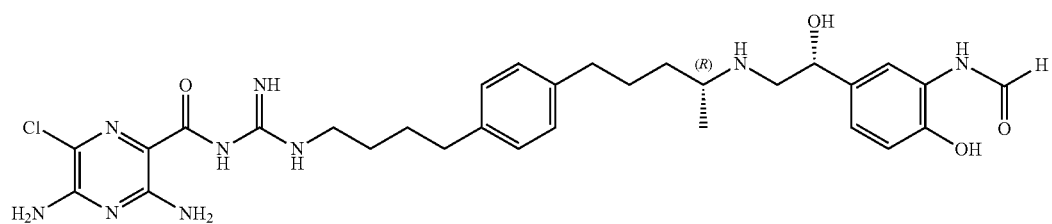

temperature. The catalyst was filtered under vacuum and washed with ethanol (3×20 mL). The filtrate and washings were combined and concentrated under vacuum. The residue was taken into dichloromethane (25 mL). To the newly formed solution was added Et$_3$N (2.32 mL, 15.45 mmol). The solution was then cooled to 0° C. in an ice bath. CbzCl (1.32 g, 7.730 mmol) was added dropwise over 10 min to the solution, which, after the addition of CbzCl, was allowed to slowly warm to ambient temperature over 3 h and continuously stirred overnight. The reaction was quenched with water (30 mL). Two layers were separated. The organic layer was washed with brine (3×30 mL), dried over anhydrous Na$_2$SO$_4$, and concentrated. The resulting residue was subjected to column chromatography eluting with 0-30% ethyl acetate in hexanes to afford the desired product 25 (0.90 g, 35%) as a colorless, viscous oil: $^1$H NMR (300 MHz, CDCl$_3$) δ 1.45 (d, 3H), 1.45-1.66 (m, 6H), 1.72-1.86 (m, 2H), 2.06-2.16 (m, 2H), 2.55 (m, 4H), 3.20 (m, 2H), 4.38 (m, 1H), 4.80 (br, 1H), 5.08 (s, 2H), 7.04 (s, 4H), 7.34 (m, 5H), 7.69 (dd, 2H), 7.81 (dd, 1H); m/z (ESI) 499 [C$_{31}$H$_{34}$N$_2$O$_4$+H]$^+$.

{4-[4-(4-Aminopentyl)phenyl]butyl}carbamic acid benzyl ester (26)

A solution containing compound 25 (0.90 g, 1.81 mmol), hydrazine (0.26 mL, 5.42 mmol) and ethanol (10 mL) was heated at 75° C. for 3 h and then cooled to ambient temperature. The white precipitate was filtered under vacuum and washed with ethanol (3×5 mL). The filtrate and washings were combined and concentrated. The residue was subjected to column chromatography eluting with a mixture of methanol (0-15%), concentrated ammonium hydroxide (0-1.5%) and dichloromethane to afford the desired product 26 (0.59 g, 88%) as a white, waxy solid: $^1$H NMR (500 MHz, CD$_3$OD) δ 1.08 (d, 3H), 1.36-1.80 (m, 8H), 2.55 (m, 4H), 2.88 (m, 1H), 3.10 (t, 2H), 5.08 (s, 2H), 7.08 (s, 4H), 7.34 (m, 5H); m/z (ESI) 369 [C$_{23}$H$_{32}$N$_2$O$_2$+H]$^+$.

[4-(4-{4-[2-(4-Benzyloxy-3-formylaminophenyl)-2-(R)-hydroxyethylamino]pentyl}-phenyl)butyl]carbamic acid benzyl ester (27)

A suspension composed of compound 26 (0.59 g, 1.60 mmol), compound 5 (0.42 g, 1.19 mmol); K$_2$CO$_3$ (0.23 g, 1.68 mmol) and chloroform (25 mL) was heated to reflux for 72 h, then cooled to ambient temperature. The solid was vacuum filtered and washed with chloroform (3×10 mL). The filtrate and the washings were combined and concentrated. The residue was subjected to column chromatography eluting with 0-10% methanol in dichloromethane. The un-reacted starting material 26 (0.39 g; 66% recovery) was recovered in the separation. A mixture of two diastereomers of the desired products 27, which were not separable in this step, was obtained (0.29 g, 28%) as a colorless, viscous oil: $^1$H NMR (500 MHz, CDCl$_3$) δ 1.08 (d, 3H), 1.37 (m, 2H), 1.48-1.68 (m, 6H), 2.55 (m, 4H), 2.74 (br, 2H), 2.92 (m, 1H), 3.18 (m, 2H), 3.58 (m, 1H), 3.72 (m, 1H), 4.70 (m, 1H), 4.80 (br, 1H), 5.08 (m, 4H), 6.92 (m, 1H), 7.08 (m, 5H), 7.22 (t, 1H), 7.34 (m, 10H), 7.92 (s, 1H), 8.31 (s, 1H); m/z (ESI) 638 [C$_{39}$H$_{47}$N$_3$O$_5$+H]$^+$.

N-[5-(2-{4-[4-(4-Aminobutyl)phenyl]-1-methylbutylamino}-1-(R)-hydroxyethyl)-2-hydroxyphenyl]formamide (28)

A mixture of compounds 27 (029 g, 0.45 mmol), palladium catalyst (0.2 g, 10% Pd on carbon, 50% wet), ethanol (10 mL) and methanol (5 mL) underwent hydrogenation at room temperature for 4 h under one H$_2$ pressure. The catalyst was vacuum filtered and washed with ethanol (3×5 mL). The filtrate and the washings were combined and concentrated. The residue was subjected to column chromatography, eluting with a mixture of methanol (0-22%), concentrated ammonium hydroxide (0-2.2%) and dichloromethane (100-75.6%), to afford the desired product 28 (0.10 g, 54%) as a colorless, glass solid: $^1$H NMR (300 MHz, CD$_3$OD) δ 1.08 (d, 3H), 1.32 (m, 2H), 1.48-1.78 (m, 6H), 2.59 (m, 4H), 2.78 (m, 5H), 3.44 (m, 2H), 4.75 (m, 1H), 6.82 (m, 1H), 7.00 (m, 1H), 7.08 (m, 5H), 8.06 (s, 1H), 8.31 (s, 1H); m/z (ESI) 414 [C$_{31}$H$_{41}$N$_3$O$_3$+H]$^+$. The diastereoisomer 29 (13 mg, 7%) was also isolated as a light yellow solid: $^1$H NMR (300 MHz, CD$_3$OD) δ 1.26 (d, 3H), 1.48-1.90 (m, 8H), 2.50 (m, 4H), 2.82-3.08 (m, 3H), 3.50 (m, 2H), 4.60 (m, 1H), 6.82-6.82 (m, 2H), 7.10 (m, 5H), 8.00 (s, 1H), 8.28 (s, 1H); m/z (ESI) 414 [C$_{31}$H$_{41}$N$_3$O$_3$+H]$^+$.

N-(5-{2-[4-(4-{4-[N'-(3,5-Diamino-6-chloropyrazine-2-carbonyl)guanidino]butyl}-phenyl)-1-methylbutylamino]-1-(R)-hydroxyethyl}-2-hydroxyphenyl)formamide (30)

A solution composed of compound 28 (0.10 g, 0.25 mmol), Hunig's base (0.21 mL, 1.23 mmol) and ethanol (5 mL) was heated at 70° C. for 30 min before 1-(3,5-diamino-6-chloropyrazine-2-carbonyl)-2-methylisothiourea hydriodide (0.11 g, 0.27 mmol) was added. The resulting solution was continuously stirred at that temperature for an additional 3 h before it was cooled to room temperature. The solvent was removed by evaporation. The resulting residue was subjected to column chromatography eluting with a mixture of methanol (0-28%), concentrated ammonium hydroxide (0-2.8%) and dichloromethane (100-69.2%) to afford 30 (87 mg, 56%) as a yellow solid: m.p. 120-121° C. (decomposed); [α]$_D^{25}$ −6.65° (c 0.20, methanol); $^1$H NMR (500 MHz, DMSO-d$_6$) δ 1.08 (d, 3H), 1.32 (m, 2H), 1.48-1.72 (m, 6H), 2.55 (m, 4H), 2.64-2.92 (m, 3H), 3.16 (m, 2H), 4.56 (m, 1H), 6.76 (m, 1H), 6.82 (m, 1H), 6.92 (m, 1H), 7.10 (m, 4H), 8.07 (s, 1H), 8.28 (s, 1H), 8.51 (s, 1H), 9.30 (s, 1H), 9.59 (s 1H); m/z (ESI) 626 [C$_{30}$H$_{40}$ClN$_9$O$_4$+H]$^+$.

Example 5

Synthesis of N-(5-{2-[4-(4-{4-[N'-(3,5-diamino-6-chloropyrazine-2-carbonyl)-guanidino]butyl}phenyl) butylamino]-1-(R)-hydroxyethyl}-2-hydroxyphenyl)-methanesulfonamide (40) (Scheme 5)

40

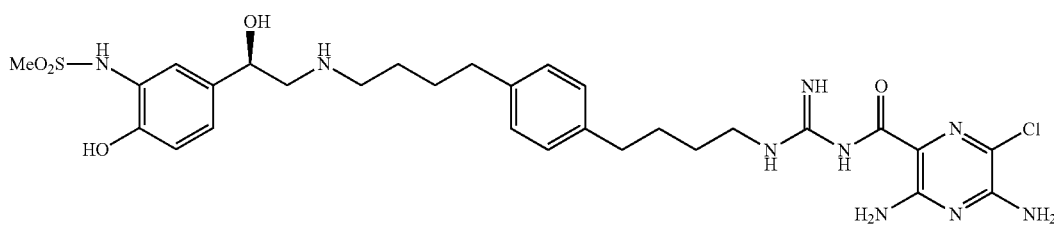

N-(5-Acetyl-2-benzyloxyphenyl)-N-benzylmethanesulfonamide (32)

A mixture of N-(5-acetyl-2-hydroxyphenyl)methanesulfonamide (31) (0.30 g, 1.32 mmol), sodium iodide (0.20 g, 1.32 mmol), potassium carbonate (0.91 g, 6.58 mmol), and benzyl bromide (0.39 mL, 3.28 mmol) in acetone (10 mL) was stirred under reflux for 66 h. After removal of solvent by rotary evaporation, the resulting residue was diluted with dichloromethane and insoluble inorganics were vacuum filtered. The filtrate was concentrated in vacuo and the resulting residue was purified by flash silica gel column chromatography eluting with a mixture of ethyl acetate (0-3%) in dichloromethane to give benzyl ether 32 as a yellow solid (0.54 g, 99%): $^1$H NMR (300 MHz, CDCl$_3$) δ 2.38 (s, 3H), 2.85 (s, 3H), 4.75 (br, 2H), 5.18 (s, 2H), 7.05 (d, 1H), 7.23 (m, 5H), 7.42 (m, 5H), 7.62 (d, 1H), 7.89 (dd, 1H); m/z (ESI) 410 [C$_{23}$H$_{23}$NO$_4$S+H]$^+$.

N-Benzyl-N-[2-benzyloxy-5-(2-bromoacetyl)phenyl]methanesulfonamide (33)

Phenyltrimethylammonium tribromide (1.19 g, 3.16 mmol) was added to a solution of N-(5-acetyl-2-benzyloxyphenyl)-N-benzylmethanesulfonamide (32) (1.23 g, 3.01 mmol) in anhydrous THF (15 mL) in three portions. The reaction mixture was stirred at rt for 16 h. An aqueous sodium bicarbonate solution (5%, 15 mL) was then added. The mixture was extracted with dichloromethane and combined organics were concentrated by rotary evaporation. The resulting residue was purified by Biotage silica gel column chromatography eluting with dichloromethane to give bromo ketone 33 as a solid (1.25 g, 85% yield): $^1$H NMR (500 MHz, CDCl$_3$) δ 2.85 (s, 3H), 4.21 (s, 2H), 4.75 (br, 2H), 5.19 (s, 2H), 7.08 (d, 1H), 7.22 (m, 5H), 7.43 (m, 5H), 7.65 (d, 1H), 7.92 (dd, 1H).

N-Benzyl-N-[2-benzyloxy-5-(2-bromo-1-(R)-hydroxyethyl)phenyl]methane-sulfonamide (34)

A solution of BH$_3$.THF in THF (1 M, 2.80 mL, 2.80 mmol) was added to a mixture of N-benzyl-N-[2-benzyloxy-5-(2-bromoacetyl)phenyl]methanesulfonamide (33) (1.09 g, 2.23 mmol) and R-methyl-CBS-oxazoborolidine (1 M in toluene, 0.45 mL, 0.45 mmol) in anhydrous THF (10 mL). The reaction mixture was stirred at 0° C. for 15 min and then at rt for 16 h. Methanol (5 mL) was slowly added to quench the reaction. After removal of solvent by rotary evaporation, the resulting residue was purified by Biotage silica gel column chromatography eluting with a mixture of ethyl acetate (0-3%) in dichloromethane to give the desired bromo alcohol 34 as a white solid (0.92 g, 84%): $^1$H NMR (500 MHz, CDCl$_3$) δ 2.60 (s, 1H), 2.85 (s, 3H), 3.30 (m, 1H), 3.38 (m, 1H), 4.70 (m, 3H), 5.11 (s, 2H), 7.00 (m, 2H), 7.21 (m, 5H), 7.28 (d, 1H), 7.42 (m, 5H).

N-Benzyl-N-(2-benzyloxy-5-(R)-oxiranylphenyl)methanesulfonamide (35)

Potassium carbonate (0.52 g, 3.76 mmol) was added to a solution of N-benzyl-N-[2-benzyloxy-5-(2-bromo-1-hydroxyethyl)phenyl]methanesulfonamide (34) (0.92 g, 1.88 mmol) dissolved in a mixed solvent of THF (8 mL) and methanol (10 mL). The reaction mixture was stirred at rt for 20 h. After removal of solvents by rotary evaporation, the residue was taken up in dichloromethane and suction filtered to remove inorganics. The filtrate was concentrated in vacuo and further co-evaporated with toluene and dried under high vacuum. The desired epoxide 35 was obtained as a white solid (0.69 g, 90%) and used directly for next step without purification: $^1$H NMR (500 MHz, CDCl$_3$) δ 2.60 (m, 1H), 2.84 (s, 3H), 3.02 (dd, 1H), 3.66 (dd, 1H), 4.75 (br, 2H), 5.10 (s, 2H), 6.97 (d, 1H), 7.01 (d, 1H), 7.12 (dd, 1H), 7.22 (m, 5H), 7.41 (m, 5H).

{4-[4-(4-{2-[3-(Benzylmethanesulfonylamino)-4-benzyloxyphenyl]-2-(R)-hydroxyethylamino}butyl)phenyl]butyl}carbamic acid benzyl ester (36)

A mixture of N-benzyl-N-(2-benzyloxy-5-(R)-oxiranylphenyl)methanesulfonamide (35) (0.69 g, 1.70 mmol) and {4-[4-(4-(4-aminobutyl)phenyl]butyl}carbamic acid benzyl ester (7) (0.77 g, 2.16 mmol) in ethanol (4 mL) was stirred under reflux for 24 h. The solvent was removed by rotary evaporation and the resulting residue was purified by Biotage silica gel column chromatography eluting with a mixture of methanol (0-8%) in dichloromethane, and then by preparative TLC eluting with a mixture of methanol (4%) in dichloromethane. The desired adduct 36 was isolated as a solid (0.41 g, 32%): $^1$H NMR (500 MHz, CDCl$_3$) δ 1.50 (m, 4H), 1.61 (m, 4H), 2.57 (m, 8H), 2.75 (br, 1H), 2.83 (s, 3H), 3.19 (m, 2H), 4.51 (dd, 1H), 4.77 (br, 3H), 5.07 (s, 2H), 5.08 (s, 2H), 6.96 (d, 1H), 6.98 (d, 1H), 7.06 (m, 4H), 7.19 (m, 5H), 7.27 (dd, 1H), 7.33 (m, 5H), 7.41 (m, 5H); m/z (ESI) 764 [C$_{45}$H$_{53}$N$_2$O$_6$S+H]$^+$. In addition, two by-products were obtained. The isomeric adduct 37 (0.23 g, 18%): $^1$H NMR (500 MHz, CDCl$_3$) δ 1.40 (m, 2H), 1.58 (m, 6H), 2.15 (br, 2H), 2.29 (m, 2H), 2.52 (m, 2H), 2.58 (t, 2H), 2.86 (s, 3H), 3.19 (m, 2H), 3.32 (dd, 1H), 3.50 (m, 2H), 4.76 (br, 2H), 5.08 (s, 2H), 5.11 (s, 2H), 6.88 (d, 1H), 6.96 (d, 1H), 7.06 (m, 4H), 7.16 (m, 6H), 7.33 (m, 5H), 7.43 (m, 5H); m/z (ESI) 764 [C$_{45}$H$_{53}$N$_3$O$_6$S+H]$^+$. And the bis-adduct 38 (0.45 g, 23%). $^1$H NMR (500 MHz, CDCl$_3$) δ 1.55 (m, 8H), 2.38 (m, 2H), 2.58 (m, 4H), 2.84 (s, 6H), 3.18 (m, 2H), 4.46 (m, 2H), 4.78 (br, 4H), 5.10 (m, 6H), 6.96 (m, 4H), 7.08 (m, 4H), 7.20 (m, 12H), 7.33 (m, 5H), 7.42 (m, 10H); m/z (ESI) 1173 [C$_{68}$H$_{76}$N$_4$O$_{10}$S$_2$+H]$^+$.

N-[5-(2-{4-[4-(4-Aminobutyl)phenyl]butylamino}-1-(R)-hydroxyethyl)-2-hydroxyphenyl]-methanesulfonamide diacetic acid salt (39)

A mixture of {4-[4-(4-{2-[3-(benzylmethanesulfonylamino)-4-benzyloxyphenyl]-2-(R)-hydroxyethylamino}butyl)phenyl]butyl}carbamic acid benzyl ester (36) (0.41 g, 0.54 mmol), palladium dihydroxide (0.12 g, 10% Pd(OH)$_2$ on carbon, 50% wet), ten drops of acetic acid, methanol (9 mL), and dichloromethane (6 mL) was stirred at rt for 16 h under atmospheric hydrogen pressure. The catalyst was removed by filtration through a Celite pad and the filtrate was concentrated by rotary evaporation and further dried under high vacuum to give the desired amine diacetic acid salt 39 as a white solid (0.30 g, 96%): m/z (ESI) 450 [C$_{23}$H$_{35}$N$_3$O$_4$S+H]$^+$.

N-(5-{2-[4-(4-{4-[N'-(3,5-Diamino-6-chloropyrazine-2-carbonyl)guanidino]butyl}-phenyl)butylamino]-1-(R)-hydroxyethyl}-2-hydroxyphenyl)methanesulfonamide (40)

Diisopropylethylamine (0.54 mL, 3.11 mmol) was added to a solution of N-[5-(2-{4-[4-(4-aminobutyl)phenyl]butylamino}-1-(R)-hydroxyethyl)-2-hydroxyphenyl]-methanesulfonamide diacetic acid salt (39) (0.30 g, 0.52 mmol) in absolute ethanol (8 mL). The mixture was stirred at 70° C. (oil bath) for 10 min, after which 1-(3,5-diamino-6-chloropyrazine-2-carbonyl)-2-methylisothiourea hydriodide (0.2) g, 0.54 mmol) was added in one portion. The reaction mixture was stirred at that temperature for 3 h and cooled to rt. The solvent was removed by rotary evaporation. The residue was purified by Biotage silica gel column chromatography (A=dichloromethane, B=10% concentrated aqueous ammonium hydroxide in methanol, gradient B/A 0% to 15%), and further purified by semi-preparative HPLC eluting with a gradient acetonitrile and water, each containing 0.01% concentrated ammonium hydroxide, to give N-(5-{2-[4-(4-{4-[N'-(3,5-diamino-6-chloropyrazine-2-carbonyl)guanidino]butyl}phenyl)butylamino]-1-(R)-hydroxyethyl}-2-hydroxyphenyl)methanesulfonamide (40) as a greenish yellow solid (0.17 g, 48%): $^1$H NMR (500 MHz, CD$_3$OD) δ 1.60 (m, 8H), 2.60 (m, 6H), 2.72 (m, 1H), 2.80 (m, 1H), 2.88 (s, 3H), 3.23 (m, 2H), 4.65 (m, 1H), 6.80 (d, 1H), 6.98 (d, 1H), 7.06 (m, 4H), 7.30 (s, 1H), m/z (ESI) 662 [C$_{29}$H$_{40}$ClN$_9$O$_5$S+H]$^+$; [α]$_D^{25}$ −7.5° (c 0.60, MeOH); mp 108-110° C.

Example 6

Synthesis of N-[5-(2-{[4-(4-{4-[N'-(3,5-diamino-6-chloropyrazine-2-carbonyl)-guanidino]butyl}phenyl)butyl]-[2-(R)-hydroxy-2-(4-hydroxy-3-methanesulfonyl-aminophenyl)ethyl]amino}-1-(R)-hydroxyethyl)-2-hydroxyphenyl]methanesulfonamide (42) (Scheme 6)

N-[5-(2-{{4-[4-(4-Aminobutyl)phenyl]butyl}-[2-(R)-hydroxy-2-(4-hydroxy-3-methanesulfonylaminophenyl)ethyl]amino}-1-(R)-hydroxyethyl)-2-hydroxyphenyl]methanesulfonamide diacetic acid salt (41)

A mixture of (4-{4-[4-(bis-{2-[3-(benzylmethanesulfonylamino)-4-benzyloxyphenyl]-2-(R)-hydroxyethyl}amino)butyl]phenyl}butyl)carbamic acid benzyl ester (38) (0.45 g, 0.383 mmol), palladium dihydroxide (0.12 g, 10% Pd(OH)$_2$ on carbon, 50% wet), ten drops of acetic acid, methanol (12 mL), and dichloromethane (6 mL) was stirred at rt for 18 h under atmospheric hydrogen pressure. The catalyst was removed by vacuum filtration through a Celite pad and the filtrate was concentrated by rotary evaporation and further dried under high vacuum to give the desired amine diacetic acid salt 41 as a white solid (0.30 g, 98%): m/z (ESI) 679 [C$_{32}$H$_{42}$N$_4$O$_6$+H]$^+$.

N-[5-(2-{[4-(4-{4-[N'-(3,5-Diamino-6-chloropyrazine-2-carbonyl)guanidino]butyl}-phenyl)butyl]-[2-(R)-hydroxy-2-(4-hydroxy-3-methanesulfonylaminophenyl)ethyl]-amino}-1-(R)-hydroxyethyl)-2-hydroxyphenyl]methanesulfonamide (42)

Diisopropylethylamine (0.33 mL, 1.89 mmol) was added to a solution of N-[5-(2-{{4-[4-(4-aminobutyl)phenyl]butyl}-[2-(R)-hydroxy-2-(4-hydroxy-3-methanesulfonyl-aminophenyl)ethyl]amino}-1-(R)-hydroxyethyl)-2-hydroxyphenyl]methanesulfonamide diacetic acid salt (41) (0.30 g, 0.375 mmol) in absolute ethanol (5 mL). The mixture was stirred at 70° C. (oil bath) for 15 min, after which 1-(3,5-diamino-6-chloropyrazine-2-carbonyl)-2-methylisothiourea hydriodide (0.16 g, 0.41 mmol) was added in one portion. The reaction mixture was stirred at that temperature for 3 h and cooled to rt. The solvent was removed by rotary evaporation. The residue was purified by Biotage silica gel column chromatography (A=dichloromethane, B=10% concentrated aqueous ammonium hydroxide in methanol, gradient B/A 0% to 25%), and further purified by preparative HPLC eluting with a gradient acetonitrile and water, each containing 0.01% concentrated ammonium hydroxide, to give the desired adduct 42 as a greenish yellow solid (78 mg, 23%): $^1$H NMR (500 MHz, DMSO-d$_6$) δ 1.50 (m, 8H), 2.58 (m, 4H), 2.88 (s, 6H), 3.20 (m, 5H), 4.48 (m, 2H), 6.60 (br, 2H), 6.78 (d, 2H), 6.90 (d, 2H), 7.10 (s, 4H), 7.18 (s, 2H); m/z (ESI) 891 [C$_{38}$H$_{51}$ClN$_{10}$O$_9$S$_2$+H]$^+$; [α]$_D^{25}$ −23.0° (c 0.40, MeOH); mp 148-150° C.

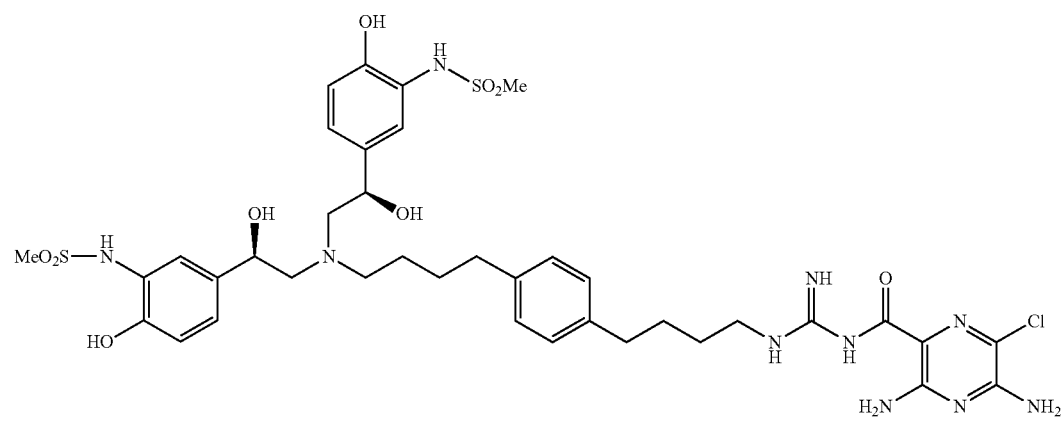

42

Example 7

Synthesis of N-(3,5-diamino-6-chloropyrazine-2-carbonyl)-N'-{11-[2-(R)-hydroxy-2-(4-hydroxy-3-hydroxymethylphenyl)ethylamino]undecyl}guanidine (55) (Scheme 7)

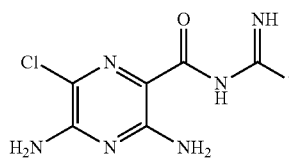 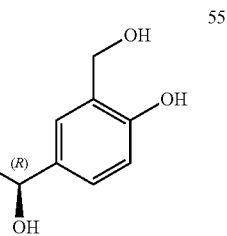

5-Acetyl-2-benzyloxy benzoic ethyl ester (44)

Benzyl chloride (3.85 ml, 33.45 mmol) was added slowly to a 60° C. solution of salicylate 43 (5.00 g, 25.75 mmol), sodium iodide (386 mg, 2.57 mmol), and sodium bicarbonate (2.50 g, 29.75 mmol) in acetonitrile (50 mL). The reaction was heated to reflux for 16 h. The solvent was removed under vacuum. The residue was taken up in ethyl acetate (50 mL), and washed sequentially with 0.5 N HCl (25 mL), water (25 mL), 5% ammonium chloride (25 mL) and then brine (25 mL). The organic portion was dried over anhydrous sodium sulfate and concentrated to an oil. Vacuum filtration of the precipitate occurred upon the addition of diethyl ether and hexanes gave ester 44 (3.98 g, 55%) as an off-white solid: $^1$H NMR (500 MHz, DMSO-$d_6$) δ 2.55 (s, 3H), 3.85 (s, 3H), 5.33 (s, 2H), 7.31-7.51 (m, 6H), 8.17-8.31 (m, 2H).

2-Benzyloxy-5-(2-bromoacetyl)benzoic acid methyl ester (45)

Phenyltrimethyl ammonium tribromide (10.60 g, 28.20 mmol) was added in 7 portions to a stirring solution of acetophenone 44 (8.00 g, 28.10 mmol) in anhydrous tetrahydrofuran (50 mL). After 18 h, the reaction mixture was poured into water (250 mL) and stirred for 1 h. The formed precipitate was collected by vacuum filtration. Re-crystallization of the collected solid from ethanol gave the α-bromide 45 (7.35 g, 72%) as a white, needle solid: $^1$H NMR (500 MHz, DMSO-$d_6$) δ 3.85 (s, 3H), 4.89 (s, 1H), 5.38 (s, 2H), 7.22 (d, 1H), 7.31-7.51 (m, 6H), 8.17-8.31 (m, 2H).

2-Benzyloxy-5-(2-bromo-1-(R)-hydroxyethyl)benzoic acid methyl ester (46)

(R)-2-Methyl-CBS-oxazoborolidine (1.38 mL of a 1.0 M solution in toluene) was added to a solution of α-bromoketone 45 (5.00 g, 13.80 mmol) in tetrahydrofuran (80 mL). After stirring for 15 min, borane tetrahydrofuran complex (8.5 mL of a 1 M solution in tetrahydrofuran) was added dropwise over a 15 min period. After stirring at ambient temperature for 1.5 h, the reaction was quenched by the slow addition of methanol (8.5 mL). The solvent was removed under vacuum. The residue was taken up in a mixed solvent of hexanes and ethyl acetate (2:1). The solid was vacuum filtered through a pad of silica gel. Concentration of the filtrate and drying under vacuum gave 46 (4.86 g, 97%) as a white solid: $^1$H NMR (500 MHz, DMSO-$d_6$) δ 3.32-3.58 (m, 1H), 3.64-3.68 (m, 1H), 3.81 (s, 3H), 4.78-4.80 (m, 1H), 5.21 (s, 2H), 5.83 (d, 1H), 7.22 (d, 1H), 7.31-7.33 (m, 1H), 7.38-7.49 (m, 5H), 7.61 (s, 1H).

2-Benzyloxy-5-(R)-oxiranyl benzoic acid methyl ester (47)

Sodium hydride (531 mg of 60% in mineral oil, 13.30 mmol) was stirred in hexanes under a nitrogen atmosphere. The hexanes were decanted to remove the mineral oil. The procedure was repeated twice. The sodium hydride was then suspended in anhydrous tetrahydrofuran (40 mL) and cooled to −20° C. A solution of bromohydrin 46 (4.85 g, 13.28 mmol) in anhydrous tetrahydrofuran (40 mL) was added dropwise to the sodium hydride suspension. After 3 h stirring, the reaction was quenched with the slow addition of water (5 mL), further diluted with water (15 mL), and extracted with ethyl acetate (3×25 mL). The combined organic extracts were washed with water (25 mL) and brine (25 mL), dried over anhydrous sodium sulfate, and concentrated to a yellow oil. After drying under vacuum, epoxide 47 (3.68 g, 97%) was obtained as a yellow oil: $^1$H NMR (500 MHz, DMSO-$d_6$) δ 2.85-2.88 (m, 1H), 3.08-3.10 (m, 1H), 3.81 (s, 3H), 3.93-3.95 (m, 1H), 5.21 (s, 2H), 7.22 (d, 1H), 7.31-7.33 (m, 1H), 7.38-7.49 (m, 5H), 7.61 (s, 1H).

(11-Aminoundecyl)carbamic acid tert-butyl ester (49)

Using a syringe pump, a solution of tert-butyl dicarbonate (3.34 g, 15.30 mmol) in methanol (50 mL) was added over 10 h to a stirring solution of diamine 48 (3.00 g, 16.10 mmol) and diisopropylethyl amine (2.80 mL, 16.00 mmol) in methanol (100 mL). The reaction was stirred for an additional 12 h. The solvent was then removed under vacuum. Purification by column chromatography eluting with 5-30% (10:90 ammonium hydroxide/methanol) in dichloromethane gave mono-protected amine 49 (2.60 g, 56%) as an off-white solid: $^1$H NMR (500 MHz, Acetone-$d_6$) δ 1.31-1.55 (m, 27H), 2.80 (br, 2H), 3.01-3.07 (m, 2H), 3.13-3.17 (m, 2H), 5.88 (br, 1H); m/z (ESI) 287 $[C_{16}H_{34}N_2O_2+H]^+$.

2-Benzyloxy-5-[2-(11-tert-butoxycarbonylaminoundecylamino)-1-(R)-hydroxyehtyl]benzoic acid methyl ester (50)

A solution of epoxide 47 (1.50 g, 5.28 mmol) in ethanol (50 mL) was added slowly to a 60° C. solution of mono-protected diamine 49 in ethanol (150 mL) over a 3 h period. After stirring for 15 h, the reaction was concentrated to an oil and purified by column chromatography eluting with 0 to 5% methanol in dichloromethane to give 50 (515 mg, 17%) as a clear oil: $^1$H NMR (500 MHz, Acetone-d$_6$) δ 1.26-1.49 (m, 27H), 2.46-2.49 (m, 2H), 2.80 (br, 3H), 3.02-3.05 (m, 2H), 3.43-3.74 (m, 3H), 3.84 (s, 3H), 5.22 (s, 2H), 5.88 (br, 1H), 5.16 (d, 1H), 7.31-7.42 (m, 3H), 7.51-7.57 (m, 3H), 7.75 (s, 1H); m/z (ESI) 571 [C$_{33}$H$_{50}$N$_2$O$_6$+H]$^+$.

{11-[2-(4-Benzyloxy-3-hydroxymethyphenyl)-2-(R)-hydroxyethylamino]undecyl}-carbamic acid tert-butyl ester (52)

Diisobutylaluminum hydride (6.15 mL of a 1.0 M solution in hexanes, 6.15 mmol) was added slowly to a solution of phenyl ester 51 (702 mg, 1.23 mmol) in tetrahydrofuran (25 mL) stirring at 0° C. The reaction was stirred for 15 min at 0° C. then warmed to ambient temperature. After 4.5 h, the reaction was cooled to 0° C. and quenched by the dropwise addition of methanol (10 mL). The reaction was concentrated to dryness and the residue was taken up in ethyl acetate. A saturated aqueous ammonium chloride solution was added into the solution. The layers were separated and the aqueous layer was extracted with ethyl acetate (2×50 mL). The combine organic extracts were washed sequentially with water and brine, dried over anhydrous sodium sulfate and concentrated to an oil. Purification of the crude oil by column chromatography eluting with 0 to 10% (10% concentrated ammonium hydroxide in methanol) in dichloromethane gave the benzyl alcohol 52 (507 mg, 76%) as an oil: $^1$H NMR (500 MHz, Acetone-d$_6$) δ 126-1.49 (m, 27H), 2.46-2.49 (m, 2H), 2.80 (br, 3H), 3.02-3.05 (m, 2H), 3.43-4.05 (m, 3H), 4.72 (s, 2H), 5.14 (s, 2H), 5.88 (hr, 1H), 7.48 (d, 1H), 7.27-7.99 (m, 7H); m/z (ESI) 543 [C$_{32}$H$_{50}$N$_2$O$_5$+H]$^+$.

{11-[2-(R)-Hydroxy-2-(4-hydroxy-3-hydroxymethylphenyl)-2-ethylamino]undecyl}-carbamic acid tert-butyl ester (53)

Benzyl alcohol 52 (507 mg, 0.93 mmol) was dissolved in ethanol (20 mL). Following the standard hydrogenation protocol, the palladium catalyst (10% palladium on carbon, 50% wet) was added to the reaction. The hydrogenation was carried out for 15 h at ambient temperature under one H$_2$ pressure. Filtration of the catalyst through diatomaceous earth and concentration of the filtrate gave a yellow oil. Purification of the crude oil by column chromatography eluting with 5% methanol in dichloromethane, then 10 to 20% (10% concentrated ammonium hydroxide in methanol) in dichloromethane gave phenol 53 (119 mg, 28%) as a clear oil: $^1$H NMR (500 MHz, Acetone-d$_6$) δ 1.26-1.49 (m, 27H), 2.46-2.49 (m, 2H), 2.80 (br, 4H), 3.02-3.05 (m, 2H), 3.43-4.05 (m, 3H), 4.72 (s, 2H), 5.88 (br, 1H), 6.77 (m, 1H), 7.13 (m, 1H), 7.48 (d, 1H); m/z (ESI) 453 [C$_{25}$H$_{44}$N$_2$O$_5$+H]$^+$.

4-[2-(11-Aminoundecylamino)-1-(R)-hydroxyethyl]-2-hydroxymethylphenol Acetic acid salt (54)

Iodo-trimethylsilane (30 μL, 0.21 mmol) was added dropwise to a solution of amine 53 (60 mg, 0.13 mmol) in anhydrous dichloromethane (1 mL). After 0.5 h, methanol (1 mL) was added to quench the reaction. The solvent was removed under vacuum and the residue was dissolved in a 1:1 mixture of 30% aqueous acetic acid and diethyl ether (20 mL). The layers were separated and the aqueous layer was extracted with diethyl ether (2×10 mL). The aqueous solution was concentrated under vacuum to give acetic acid salt 54 (71 mg, quant yield). This compound was used directly in the subsequent reaction without further purification.

N-(3,5-Diamino-6-chloropyrazine-2-carbonyl)-N'-{11-[2-(R)-hydroxy-2-(4-hydroxy-3-hydroxymethylphenylethylamino]undecyl}guanidine (55)

Diisopropylethylamine (0.10 mL, 0.57 mmol) and 1-(3,5-diamino-6-chloropyrazine-2-carbonyl)-2-methylisothiourea hydriodide (50 mg, 0.13 mmol) were sequentially added to a solution of 54 (61 mg, 0.13 mmol) in ethanol (4 mL). The reaction mixture was heated to 70° C. for 6.5 h after which time it was cooled and concentrated under vacuum. The resulting residue was purified first by column chromatography, eluting with 1-20% (30:70 concentrated ammonium hydroxide/methanol) in dichloromethane, then by prep HPLC, affording the desired product 55 (4 mg, 5%) as a yellow solid: $^1$H NMR (500 MHz, CD$_3$OD) 1.26-1.67 (m, 18H), 2.19-2.24 (m, 2H), 2.51-2.58 (m, 2H), 3.25-3.30 (m, 2H), 4.57-4.64 (m, 3H), 6.75 (d, 1H), 7.07 (dd, 1H), 7.23 (d, 1H); m/z (ESI) 565 [C$_{27}$H$_{41}$ClN$_8$O$_4$+H]$^+$.

Example 8

Synthesis of N-(3,5-diamino-6-chloropyrazine-2-carbonyl)-N'-[4-(4-{4-[2-(R)-hydroxy-2-(4-hydroxy-3-hydroxymethylphenyl)ethylamino]butyl}phenyl)butyl]-guanidine (63) (Scheme 8)

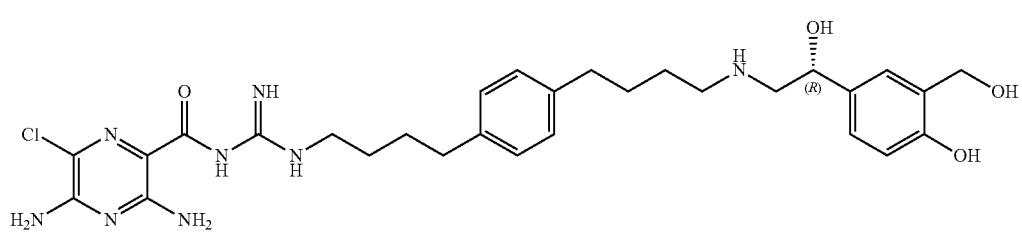

2-[4-(4-Iodophenyl)but-3-ynyl]isoindole-1,3-dione (57)

A solution containing triethylamine (250 mL), copper (I) iodide (1.72 g, 9.09 mmol) and diiodobenzene (56) (20.00 g, 60.60 mmol) dissolved in anhydrous tetrahydrofuran (250 mL) was stirred at room temperature. The reaction flask was evacuated and then purged with nitrogen three times. The solution was treated with bis(triphenylphosphine) palladium (II) dichloride (4.20 g, 6.06 mmol) and continued to stir at room temperature for 30 min. A solution containing triethylamine (250 mL) and 2-but-3-ynylisoindole-1,3-dione (12.06 g, 60.06 mmol) dissolved in anhydrous tetrahydrofuran (250 mL) was added dropwise through an addition funnel over 12 hours. The reaction was allowed to stir at room temperature for 48 h. The solution was filtered and the filtrate was concentrated in vacuo. The resulting residue was purified by column chromatography eluting with 0-100% ethyl acetate in hexanes to afford the desired product 57 (12.5 g, 51%) as a brown solid: $^1$H NMR (500 MHz, CD$_2$Cl$_2$) δ 7.85 (dd, 2H), 7.74 (dd, 2H), 7.60 (d, 2H), 7.04 (d, 2H), 3.92 (t, 2H), 2.79 (t, 2H); m/z (ESI) 402 [C$_{18}$H$_{12}$INO$_2$+H]$^+$.

(4-{4-[4-(1,3-Dioxo-1,3-dihydroisoindol-2-yl)but-1-ynyl]phenyl}but-3-ynyl)-carbamic acid benzyl ester (58)

A solution containing triethylamine (100 mL), copper (I) iodide (0.50 g, 2.60 mmol) and 57 (7.00 g, 17.40 mmol) dissolved in anhydrous tetrahydrofuran (100 mL) was stirred at room temperature. The reaction flask was vacuumed and then purged with nitrogen three times. The solution was treated with bis(triphenylphosphine) palladium(II) dichloride (1.20 g, 1.70 mmol) and continued to stir at room temperature for 30 min. The reaction mixture was then treated with but-3-ynylcarbamic acid benzyl ester (4.25 g, 20.90 mmol). The reaction was allowed to stir at room temperature for 16 h. The solution was filtered and the filtrate was concentrated in vacuo. The resulting residue was purified by column chromatography eluting with 0-100% ethyl acetate in hexanes to afford the desired product 58 (6.0 g, 72%) as a brown solid: $^1$H NMR (500 MHz, CD$_2$Cl$_2$) δ 7.85 (dd, 2H), 7.74 (dd, 2H), 7.35-7.32 (m, 5H), 7.27 (d, 2H), 7.22 (d, 2H), 5.08 (s, 2H), 3.93 (t, 2H), 3.39 (t, 2H), 2.81 (t, 2H), 2.62 (t, 2H); m/z (ESI) 477 [C$_{30}$H$_{24}$N$_2$O$_4$+H]$^+$.

(4-{4-[4-(1,3-Dioxo-1,3-dihydroisoindol-2-yl)butyl]phenyl}butyl)carbamic acid benzyl ester (59)

A suspension containing 58 (6.0 g, 12.59 mmol) and palladium dihydroxide (20% Pd(OH)$_2$ on carbon, 50% wet, 3.0 g, 21.43 mmol) dissolved in anhydrous tetrahydrofuran 75 mL) was bubbled with nitrogen for 20 min. The reaction mixture was vacuumed, then charged with H$_2$ gas (45 psi), and allowed to stir at rt for 24 h. The solution was filtered and the filtrate was concentrated in vacuo. The resulting residue was purified by column chromatography eluting with 0-100% ethyl acetate in hexanes to afford the desired product 59 (4.88 g, 80%) as a thick, brown oil: $^1$H NMR (500 MHz, CDCl$_3$) δ 7.85 (dd, 2H), 7.74 (dd, 2H), 7.35-728 (m, 6H), 7.06 (d, 4H), 3.70 (t, 2H), 3.19 (t, 2H), 2.63-2.56 (m, 4H), 2.00 (d, 2H), 1.73-1.50 (m, 8H); m/z (ESI) 485 [C$_{30}$H$_{32}$N$_2$O$_4$+H]$^+$.

{4-[4-(4-Aminobutyl)phenyl]butyl}carbamic acid benzyl ester (7)

A solution containing 59 (4.0 g, 8.20 mmol) and hydrazine (2.06 g, 41.20 mmol) dissolved in ethanol (50 mL) and methylene chloride (10 mL) was heated to reflux. The reaction mixture was allowed to stir for 16 h under N$_2$ atmosphere. The solution was filtered and the filtrate was concentrated in vacuo. The resulting residue was purified by column chromatography eluting with a mixture of 0-20% (10% concentrated ammonium hydroxide in methanol) and dichloromethane to afford the desired product 7 (6.00 g, 72%) as an off white solid: $^1$H NMR (300 MHz, CDCl$_3$) δ 7.34 (s, 4H), 7.07 (s, 4H), 5.08 (s, 2H), 3.18 (t, 2H), 2.94 (s, 2H), 2.70 (t, 2H), 2.59 (t, 4H), 1.65-1.47 (m, 5H); m/z (ESI) 355 [C$_{22}$H$_{30}$N$_2$O$_2$+H]+.

2-Benzyloxy-5-(2-{4-[4-(4-benzyloxycarbonylaminobutyl)phenyl]butylamino}-1-(R)-hydroxyethyl)benzoic acid methyl ester (60)

A solution containing 7 (1.30 g, 3.67 mmol) and 2-benzyloxy-5-(R)-oxiranylbenzoic acid methyl ester 47 (1.14 g, 4.04 mmol) dissolved in ethanol (30 mL) was heated to 60° C. The solution was stirred at that temperature for 48 h under atmosphere. The solution was concentrated in vacuo. The resulting residue was purified by column chromatography eluting with a mixture of 0-20% (10% concentrated ammonium hydroxide in methanol) and dichloromethane to afford the desired products 60 (0.76 g, 33%) as an off-white solid: $^1$H NMR (500 MHz, CDCl$_3$) δ 7.80 (d, 1H), 7.72 (d, 1H), 7.44 (d, 2H), 7.34 (d, 10H), 7.05 (d, 4H), 7.00 (dd, 1H), 5.17 (s, 2H), 5.08 (s, 2H), 4.89 (dd, 1H), 3.89 (s, 3H), 3.19 (t, 2H), 2.90 (dd, 2H), 2.91-2.46 (m, 8H), 1.61-1.50 (m, 8H), m/z (ESI) 639 [C$_{39}$H$_{46}$N$_2$O$_6$+H]$^+$. As a by-product of this reaction, 64 (see Scheme 9) (0.57 g, 18%) was also isolated as an off white solid: m/z (ESI) 924 [C$_{56}$H$_{62}$N$_2$O$_{10}$+H]$^+$.

[4-(4-{4-[2-(4-Benzyloxy-3-hydroxymethylphenyl)-2-(R)-hydroxyethylamino]butyl}-phenyl)butyl]carbamic acid benzyl ester (61)

A solution of 60 (0.62 g, 0.97 mmol) dissolved in anhydrous tetrahydrofuran (6 as cooled to 0° C. The solution was treated with diisobutylaluminum hydride (4.8 mL, 1M in hexanes). The reaction mixture was allowed to slowly warm to room temperature over 16 h. The solution was concentrated in vacuo. The resulting residue was purified by column chromatography eluting with a mixture of 0-20% (10% concentrated ammonium hydroxide in methanol) and dichloromethane to afford the desired product 61 (0.38 g, 64%) as an off-white solid: $^1$H NMR (500 MHz, CD$_3$OD) δ 7.43 (s, 4H), 7.40-7.17 (m, 10H), 7.07 (s, 2H), 6.97 (dd, 1H), 5.12 (s, 2H), 5.04 (s, 2H), 4.78 (dd, 1H), 4.69 (d, 2H), 3.63 (t, 2H), 3.11 (t, 2H), 2.62-2.46 (m, 6H), 1.61 (br, 4H), 1.51 (br, 2H); m/z (ESI) 611 [C$_{38}$H$_{46}$N$_2$O$_5$+H]$^+$.

4-(2-{4-[4-(4-Aminobutyl)phenyl]butylamino}-1-(R)-hydroxyethyl)-2-hydroxy-methylphenol (62)

A suspension containing 61 (0.38 g, 0.62 mmol) and palladium catalyst (10% Pd on carbon, 50% wet, 0.50 g, 4.69 mmol) in ethanol (15 mL) was bubbled with nitrogen for 20 min. The reaction mixture was vacuumed, then charged with H$_2$ gas (1 atm), and allowed to stir at room temperature for 24 h. The catalyst was vacuum filtered and the filtrate was concentrated in vacuo. The resulting residue was purified by column chromatography eluting with a mixture of 0-20% (10% concentrated ammonium hydroxide in methanol) and dichloromethane to afford the desired product 62 (0.24 g, 98%) as an off-white solid: $^1$H NMR (500 MHz, CD$_3$OD) δ 7.21 (d, 1H), 7.09-7.04 (m, 4H), 7.08 (dd, 2H), 4.63 (d, 2H), 3.65 (t, 2H), 3.59-3.54 (m, 2H), 2.77-2.43 (m, 11H), 1.64 (t, 2H), 1.58 (t, 2H); m/z (ESI) 387 [C$_{23}$H$_{34}$N$_2$O$_3$H]$^+$.

N-(3,5-Diamino-6-chloropyrazine-2-carbonyl)-N'-[4-(4-{4-[2-(R)-hydroxy-2-(4-hydroxy-3-hydroxymethylphenyl)ethylamino]butyl}phenyl)butyl]guanidine (63)

A solution containing 62 (0.24 g, 0.62 mmol) dissolved in ethanol (8 mL) was heated to 65° C. The reaction mixture was treated with 1-(3,5-diamino-6-chloropyrazine-2-carbonyl)-2-methylisothiourea hydriodide (0.24 mg, 0.62 mmol) and diisopropylethylamine (0.47 mL). The reaction mixture was stirred at that temperature for 5 h under $N_2$ atmosphere. The solution was concentrated vacuo. The resulting residue was first purified by column chromatography eluting with a mixture of 0-20% (10% concentrated ammonium hydroxide in methanol) and dichloromethane, and then further purified by preparative TLC using the same solvent system to afford the desired product 63 (15 mg, 5%) as a pale yellow solid: $^1$H NMR (500 MHz, DMSO-$d_6$) δ 7.22 (d, 1H), 7.08 (d, 4H), 6.97 (d, 1H), 6.68 (d, 4H), 6.57 (br, 1H), 4.45 (s, 2H), 3.15 (d, 2H), 2.33 (t, 1H), 1.59-1.52 (m, 6H), 1.39 (s, 2H), 1.23 (s, 1H), m/z (ESI) 600 $[C_{29}H_{39}ClN_8O_4+H]^+$.

Example 9

Synthesis of N-{4-[4-(4-{bis-[2-(R)-hydroxy-2-(4-hydroxy-3-hydroxymethylphenyl)-ethyl]amino}butyl)-phenyl]butyl}-N'-(3,5-diamino-6-chloropyrazine-2-carbonyl)-guanidine (67) (Scheme 9)

dichloromethane to afford the desired product 65 (0.25 g, 47%) as an off white solid: m/z (ESI) 868 $[C_{54}H_{62}N_2O_8+H]^+$.

{4-[4-(4-{Bis-[2-(4-hydroxy-3-hydroxymethylphenyl)-2-(R)-hydroxyethyl]amino}-butyl)phenyl]butyl}amine (66)

A suspension containing 65 (250 mg, 0.28 mmol) and palladium catalyst (10% Pd on carbon, 50% wet, 100 mg, 0.94 mmol) in ethanol (10 mL) was bubbled with nitrogen for 20 min. The reaction mixture was vacuumed, then charged with $H_2$ gas (1 atm), and allowed to stir at room temperature for 24 h. The suspension was filtered and the filtrate was concentrated in vacuo. The resulting residue was purified by column chromatography eluting with a mixture of 0-20% (10% concentrated ammonium hydroxide in methanol and dichloromethane to afford the desired product 66 (45 mg, 28%) as an off white solid: m/z (ESI) 553 $[C_{32}H_{44}N_2O_6+H]^+$.

N-{4-[4-(4-{Bis-[2-(R)hydroxy-2-(4-hydroxy-3-hydroxymethylphenyl)ethyl]amino}-butyl)phenyl]butyl}-N'-(3,5-diamino-6-chloropyrazine-2-carbonyl)guanidine (67)

A solution containing 66 (45 mg, 0.08 mmol) dissolved in ethanol (4 mL) was heated to 65° C. The reaction mixture was treated with 1-(3,5-diamino-6-chloropyrazine-2-carbonyl)-2-methylisothiourea hydriodide (32 mg, 0.12 mmol) and

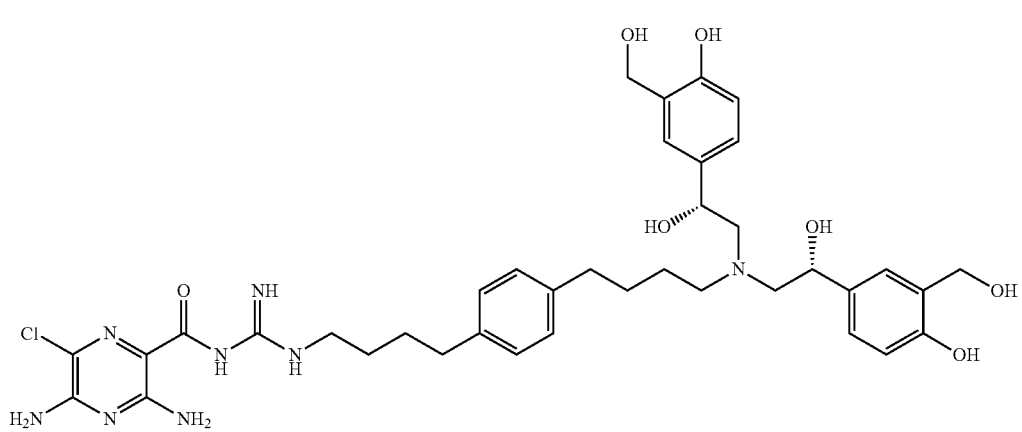

67

{4-[4-(4-{Bis-[2-(4-benzyloxy-3-hydroxymethylphenyl)-2-(R)-hydroxyethyl]amino}butyl)phenyl]butyl}carbamic acid benzyl ester (65)

A solution of 64 (567 mg, 0.61 mmol) dissolved in anhydrous tetrahydrofuran (5 mL) was cooled to 0° C. The solution was treated with diisobutylaluminum hydride (3.0 mL, 1 M in hexanes). The reaction mixture was allowed to slowly warm to room temperature over 16 h. The solution was concentrated in vacuo. The resulting residue was purified by column chromatography eluting with a mixture of 0-20% (10% concentrated ammonium hydroxide in methanol) and diisopropylethylamine (0.40 μL). The reaction mixture was stirred at that temperature for 5 h under $N_2$ atmosphere. The solution was concentrated in vacuo. The resulting residue was first purified by column chromatography eluting with a mixture of 0-20% (10% concentrated ammonium hydroxide in methanol) and dichloromethane and then further purified by preparative TLC using the same solvent system to afford the desired product 67 (18 mg, 30%) as a pale yellow solid: $^1$H NMR (500 MHz, DMSO-$d_6$) δ 7.26 (s, 1H), 7.10 (s, 2H), 6.97 (s, 1H), 6.68 (s, 1H), 6.58 (s, 1H), 4.88 (br, 1H), 4.46 (s, 3H), 3.16 (s, 2H), 1.58-1.23 (m, 6H); m/z (ESI) 766 $[C_{39}H_{53}ClN_8O_7+H]^+$.

Example 10

Synthesis of N-(5-{2-[4-(4-{4-[N'-(3,5-diamino-6-chloropyrazine-2-carbonyl)-guanidino]butyl}phenyl)-1-methylbutylamino]-1-(R)-hydroxyethyl}-2-hydroxyphenyl)formamide (30) Bis-Lactate Di-Hydrate Salt

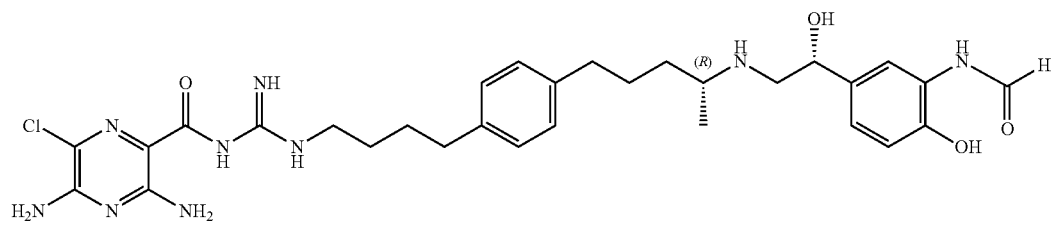

To a solution of 160 mg of N-(5-{2-[4-(4-{4-[N'-(3,5-diamino-6-chloropyrazine-2-carbonyl)-guanidino]butyl}phenyl)-1-methylbutylamino]-1-(R)-hydroxyethyl}-2-hydroxyphenyl)formamide (30) in ethanol was added 2.0 equivalents of lactic acid and stirred at room temperature for 1 hour. The ethanol was removed by rotary evaporation to yield 202 mg of the desired N-(5-{2-[4-(4-{4-[N'-(3,5-diamino-6-chloropyrazine-2-carbonyl)-guanidino]butyl}phenyl)-1-methylbutylamino]-1-(R)-hydroxyethyl}-2-hydroxyphenyl)formamide (Bis-Lactate Di-Hydrate Salt), $[\alpha]_D^{25}$ −25.3° (c 0.25, MeOH); mp 116-119° C., m/z=626, elemental analysis C, H, N within 0.3%.

Biological Activity

The compounds in the examples below were tested for potency in canine bronchial epithelia using the in vitro assays described above.

Example 11

Compound 30 ENaC blocking Activity, IC50 (nM)=8.4 (93× Amiloride)
Beta Agonist Activity, EC50 (nM)=71.6 (fomoterol=13.1)

Example 12

Compound 67 ENaC blocking Activity, IC50 (nM)=22.2 (29× Amiloride)

Example 13

Compound 14 ENaC blocking Activity, IC50 (nM)=17.7 (66× Amiloride)

Example 14

Compound 42 ENaC blocking Activity, IC50 (nM)=21.6 (54× Amiloride)

Example 15

Compound 19 ENaC blocking Activity, IC50 (nM)=10 (120× Amiloride)

Example 16

Compound 12 ENaC blocking Activity, IC50 (nM)=5.7 (132× Amiloride)
Beta Agonist Activity, EC50 (nM)=151 (fomoterol=5.3)

Example 17

Compound 63 ENaC blocking Activity, IC50 (nM)=6.5 (154× Amiloride)

Example 18

Compound 40 ENaC blocking Activity, IC50 (nM)=9.2 (91× Amiloride)
Beta Agonist Activity, EC50 (nM)=1576 (fomoterol=9.3)

Example 19

Synthesis of N-(5-{2-[4-(4-{4-[N'-(3,5-diamino-6-chloropyrazine-2-carbonyl)guanidino]butyl}-phenyl)butylamino]-1-(R)-hydroxyethyl}-2-hydroxyphenyl)methanesulfonamide diacetate 137 (Scheme 10)

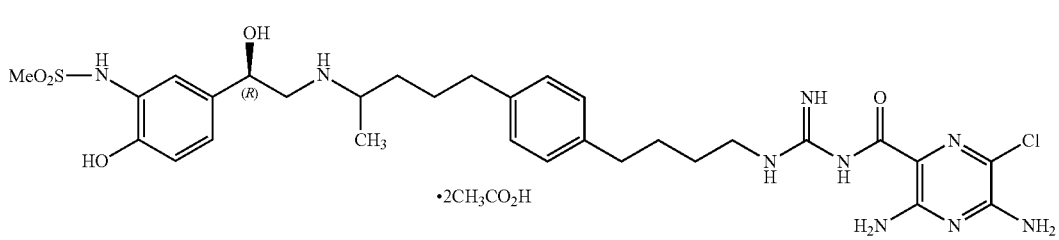

137

N-(5-Acetyl-2-benzyloxyphenyl)-N-benzylmethanesulfonamide (130)

A mixture of N-(5-acetyl-2-hydroxyphenyl)methanesulfonamide (129) (20.00 g, 87.10 mmol), sodium iodide (13.00 g, 86.70 mmol), potassium carbonate (60.00 g, 434.10 mmol), and benzyl bromide (26.00 mL, 218.90 mmol) in acetone (670 mL) was stirred under reflux for 15 h. The reaction mixture was then cooled to room temperature, the solid was removed by filtration and the filtrate was concentrated in vacuo. Purification by flash column chromatography (silica gel, a gradient of 0:100 to 30:70 ethyl acetate/dichloromethane) gave benzyl ether 30 as a yellow solid (29.60 g, 77% yield): $^1$H NMR (300 MHz, CDCl$_3$) δ 2.38 (s, 3H), 2.85 (s, 3H), 4.75 (br s, 2H), 5.18 (s, 2H), 7.05 (d, 1H), 7.23 (m, 5H), 7.42 (m, 5H), 7.62 (d, 1H), 7.89 (dd, 1H); m/z (ESI) 410 [C$_{23}$H$_{23}$NO$_4$S+H]$^+$.

N-Benzyl-N-[2-benzyloxy-5-(2-bromoacetyl)phenyl]methanesulfonamide (131)

Phenyltrimethylammonium tribromide (28.60 g, 76.10 mmol) was added to a solution of (5-acetyl-2-benzyloxyphenyl)-N-benzylmethanesulfonamide (130) (29.60 g, 72.30 mmol) in anhydrous THF (150 mL) in four portions. The reaction mixture was stirred at ambient temperature for 14 h. The solids were removed by vacuum filtration and the filtrate was concentrated by rotary evaporation. The resulting residue was purified by column chromatography (silica gel, dichloromethane only) to give bromo ketone 131 as an off-white solid (25.10 g, 71% yield): $^1$H NMR (500 MHz, CDCl$_3$) δ 2.85 (s, 3H), 4.21 (s, 2H), 4.75 (br, 2H), 5.19 (s, 2H), 7.08 (d, 1H), 7.22 (m, 5H), 7.43 (m, 5H), 7.65 (d, 1H) 7.92 (dd, 1H).

N-Benzyl-N-[2-benzyloxy-5-(2-bromo-1-(R)-hydroxyethyl)phenyl]methane-sulfonamide (132)

A solution of BH$_3$.THF in THF (1 M, 30.70 mmol) was added to a mixture of N-benzyl-N-[2-benzyloxy-5-(2-bromoacetyl)phenyl]methanesulfonamide (131) (25.00 g, 51.20 mmol) and R-methyl-CBS-oxazoborolidine (1 M in toluene, 5.10 mL, 5.10 mmol) in anhydrous THF (150 mL). The reaction mixture was stirred at 0° C. for 15 min and then at rt for 16 h. Methanol (100 mL) was then slowly added to quench the reaction. After removal of solvent by rotary evaporation, the resulting residue was purified by column chromatography (silica gel, dichloromethane only) to give desired bromo alcohol 132 as an orange oil (23.80 g, 95% yield): $^1$H NMR (500 MHz, CDCl$_3$) δ 2.86 (s, 3H), 3.30-3.38 (m, 2H), 4.70 (m, 3H), 5.11 (s, 2H), 7.00 (m, 2H), 7.21 (m, 5H), 7.28 (d, 1H), 7.42 (m, 5H).

N-Benzyl-N-(2-benzyloxy-5-(R)-oxiranylphenyl)methanesulfonamide (133)

Potassium carbonate (0.50 g, 3.58 mmol) was added to a solution of N-benzyl-N-[2-benzyloxy-5-(2-bromo-1-hydroxyethyl)phenyl]methanesulfonamide (132) (1.00 g, 2.04 mmol) dissolved in a solvent mixture of THF (8 mL) and methanol (8 mL), and the reaction mixture was stirred at rt for 2 h. After removal of solvents by rotary evaporation, the residue was taken up in dichloromethane and suction filtered to remove the inorganics. The filtrate was concentrated in vacuo and further co-evaporated with toluene and dried under high vacuum. The desired epoxide 133 was obtained as a white solid (1.01 g, >99% yield) and used directly for next step without purification: $^1$H NMR (500 MHz, CDCl$_3$) δ 2.60 (m, 1H), 2.84 (s, 3H), 3.02 (dd, 1H), 3.66 (dd, 1H), 4.75 (br s, 2H), 5.10 (s, 2H), 6.97 (d, 1H), 7.01 (d, 1H), 7.12 (dd, 1H), 7.22 (m, 5H), 7.41 (m, 5H).

(R)-benzyl {4-[4-(4-{2-[3-(N-benzylmethanesulfonylamino)-4-benzyloxy]phenyl}-2-hydroxyethylamino)butyl]phenyl}butylcarbamate (135)

A mixture of N-benzyl-N-(2-benzyloxy-5-(R)-oxiranylphenyl)methanesulfonamide (133) (1.25 g, 3.05 mmol) and benzyl 4-[4-(4-aminopentyl)phenyl]butylcarbamate (134) (1.25 g, 3.39 mmol) in anhydrous chloroform (15 mL) was heated to 68° C. in a sealed tube for 96 h. After this time, the mixture was cooled to rt and the solvent was removed by rotary evaporation. The resulting residue was purified by column chromatography (silica gel, 5:95 methanol/dichloromethane). Desired adduct 135 (0.35 g, 15% yield) was isolated as a white foam: $^1$H NMR (500 MHz, CDCl$_3$) δ 0.88-0.94 (m, 3H), 1.21-1.61 (m, 10H), 2.34-2.57 (m, 5H), 2.86 (m, 3H), 3.19 (m, 2H), 3.43-3.69 (m, 2H), 4.77 (br s, 3H), 5.07 (m, 2H), 5.30 (s, 2H), 6.86-7.43 (m, 22H); m/z (ESI) 778 [C$_{46}$H$_{55}$N$_3$O$_6$S+H]$^+$.

N-[5-((1R)-2-{5-[4-(4-Aminobutyl)phenyl]pentan-2-ylamino}-1-hydroxyethyl)-2-hydroxyphenyl]-methanesulfonamide (136)

A mixture of (R)-benzyl {4-[4-(4-{2-[3-(N-benzylmethanesulfonylamino)-4-benzyloxy]phenyl}-2-hydroxyethylamino)butyl]phenyl}butylcarbamate (135) (0.35 g, 0.46 mmol), palladium dihydroxide (50 mg, 10% Pd(OH)$_2$ on carbon, 50% wet) and ethanol (15 mL) was stirred at rt for 16 h under atmospheric hydrogen pressure. The catalyst was removed by filtration through diatomaceous earth and the filtrate concentrated by rotary evaporation, then further dried under high vacuum to give the desired amine 136 as a tan solid (0.21 g, 97% yield): $^1$H NMR (500 MHz, CD$_3$OD) δ 1.08-1.11 (m, 3H), 1.21-1.61 (m, 10H), 2.34-2.57 (m, 5H), 2.71-2.92 (m, 8H), 4.63 (m, 1H), 6.84-6.88 (m, 1H), 7.01-7.12 (m, 5H), 7.36 (s, 1H); m/z (ESI) 464 [C$_{24}$H$_{37}$N$_3$O$_4$S+H]$^+$.

N-(5-{2-[4-(4-{4-[N'-(3,5-Diamino-6-chloropyrazine-2-carbonyl)guanidino]butyl}-phenyl)butylamino]-1-(R)-hydroxyethyl}-2-hydroxyphenyl)methanesulfonamide diacetate (137)

Diisopropylethylamine (0.10 mL, 0.57 mmol) was added to a mixture of N-[5-((1R)-2-{5-[4-(4-Aminobutyl)phenyl]pentan-2-ylamino}-1-hydroxyethyl)-2-hydroxyphenyl]-methanesulfonamide (136) (0.21 g, 0.45 mmol) and 1-(3,5-diamino-6-chloropyrazine-2-carbonyl)-2-methylisothiourea hydriodide (5) (0.18 g, 0.45 mmol) in absolute ethanol (8 mL). The mixture was stirred at 70° C. (oil bath) for 2 h. After this time the mixture was cooled to rt and the solvent was removed by rotary evaporation. The residue was purified by column chromatography (silica gel, a gradient of 10:90 to 30:70 (10% concentrated aqueous ammonium hydroxide in methanol/in dichloromethane) and further purified by semi-preparative HPLC (a gradient of 10:90 to 90:10 acetonitrile/water, each containing 0.01% concentrated acetic acid) to give sulfonamide derivative (137) as a tan solid (25.0 mg, 8% yield): mp 76-80° C.; $^1$H NMR (500 MHz, CD$_3$OD) δ 0.94-0.97 (m, 3H), 1.24 (br s, 1H), 1.40 (br s, 1H), 1.51-1.60 (m, 6H), 190 (s, 6H), 2.49-2.66 (m, 6H), 2.89 (s, 3H), 3.11-3.19 (m, 2H), 4.63 (m, 1H), 6.63 (br, 2H), 6.80 (d, 1H), 6.98 (d, 1H), 7.06 (n), 4H), 7.16 (s, 1H); m/z (ESI) 676 [C$_{30}$H$_{42}$ClN$_9$O$_5$S+H]$^+$.

Example 20

Synthesis of 3,5-diamino-6-chloro-N-{N-[4-(4-{4-[(R)-2-hydroxy-2-(3-hydroxyphenyl)ethylamino]pentyl}phenyl)butyl]carbamimidoyl}pyrazine-2-carboxamide 143 (Scheme 11)

3-((R)-2-{5-[4-(4-Aminobutyl)phenyl]pentan-2-ylamino}-1-hydroxyethyl)phenol (142)

A mixture of butylcarbamate 141 (1.04 g, 2.06 mmol), palladium dihydroxide (0.20 g, 10% Pd(OH)$_2$ on carbon, 50% wet) and ethanol (10 mL) was stirred at rt for 94 h under

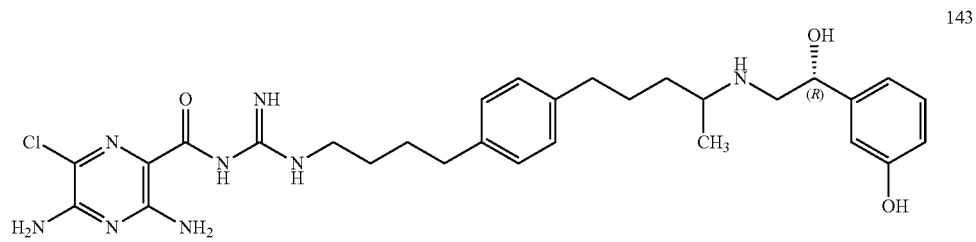

143 atmospheric hydrogen pressure. The catalyst was removed by filtration through diatomaceous earth and the filtrate was concentrated by rotary evaporation. Purification by column chromatography (silica, a gradient of 0:100 to 10:90 (10% concentrated ammonium hydroxide/methanol)/dichloromethane) gave desired amine 142 (0.63 g, 83% yield) as a tan solid: $^1$H NMR (500 MHz, CDCl$_3$) δ 1.16-1.29 (m, 3H), 1.48-1.74 (m, 8H), 2.50-2.60 (m, 4H), 2.92-3.30 (m, 5H), 4.83 (br s, 1H), 6.71-6.72 (m, 1H), 6.83-6.85 (m, 2H), 7.00-7.15 (m, 5H); m/z (ESI) 371 [C$_{23}$H$_{34}$N$_2$O$_2$+H]$^+$.

Benzyl 4-[4-(4-oxopentyl)phenyl]butylcarbamate (140)

Pyrididium chlorochromate (7.32 g, 34.00 mmol) was added to a mixture of benzyl 4-[4-(4-hydroxypentyl)phenyl]butylcarbamate (138) (6.27 g, 17.00 mmol) and 4 Å molecular sieves in dichloromethane (250 mL) in three portions and stirred at rt for 6 h. The reaction mixture was then filtered through diatomaceous earth and the filtrate was concentrated to a black oil. Purification by column chromatography (silica, 30:70 ethyl acetate/hexanes) afforded ketone 140 (6.58 g, >99% yield) as a white solid: $^1$H NMR (500 MHz, CDCl$_3$) δ 1.50-1.56 (m, 2H), 1.60-1.66 (m, 2H), 1.85-1.90 (m, 2H), 2.11 (s, 3H), 2.42 (t, 2H), 2.56-2.60 (m, 4H), 3.19-3.23 (m, 2H), 4.70 (br s, 1H), 5.08 (s, 2H), 7.07 (s, 4H), 7.29-7.36 (m, 5H).

Benzyl 4-(4-{4-[(R)-2-hydroxy-2-(3-hydroxyphenyl)ethylamino]pentyl}-phenyl)butylcarbamate (141)

A solution of commercially available amino alcohol salt 139 (0.39 g, 2.06 mmol) and ketone 140 (0.75 g, 2.04 mmol) in methanol (10 mL) were stirred at ambient temperature for 5 h. Sodium triacetoxyborohydride (1.30 g, 6.13 mmol) was then added in four portions and stirred for an additional 14 h. The reaction mixture was then filtered and the filtrate was concentrated. Purification by chromatography (silica column, 30:70 ethyl acetate/hexanes, followed by 10:90 (10% concentrated ammonium hydroxide/methanol)/dichloromethane) gave butyl carbamate 141 (1.01 g, >99% yield) as a sticky, white foam: $^1$H NMR (500 MHz, CDCl$_3$) δ 1.21 (br s, 3H), 1.48-1.74 (m, 10H), 2.00 (s, 3H), 2.50-2.60 (m, 5H), 2.92-3.30 (m, 5H), 4.88 (br s, 1H), 4.97 (br s, 1H), 5.08 (s, 2H), 6.75 (br s, 2H), 6.89 (br s, 1H), 7.00-7.11 (m, 5H), 7.29-7.36 (m, 5H); m/z (ESI) 505 [C$_{31}$H$_{40}$N$_2$O$_4$H]$^+$.

3,5-Diamino-6-chloro-N-{N-[4-(4-{4-[(R)-2-hydroxy-2-(3-hydroxyphenyl)ethylamino]pentyl}phenyl)butyl]carbamimidoyl}pyrazine-2-carboxamide (143)

Diisopropylethylamine (0.45 mL, 2.58 mmol) was added to a mixture of amino alcohol 142 (0.63 g, 1.69 mmol) and 1-(3,5-diamino-6-chloropyrazine-2-carbonyl)-2-methyl-isothiourea hydriodide (0.66 g, 2.58 mmol) in absolute ethanol (10 mL). The mixture was stirred at 75° C. (oil bath) for 4.5 h. After this time the mixture was cooled to rt and the solvent was removed by rotary evaporation. Purification by column chromatography (silica gel, a gradient of 5:95 to 10:90 methanol/dichloromethane, followed by a gradient of 5:95 to 10:90 (10% concentrated aqueous ammonium hydroxide/methanol)/dichloromethane) and subsequent drying in a 40° C. vacuum oven for 88 h afforded the phenol derivative 143 (0.30 g, 30% yield) as a yellow solid: mp 82-86° C.; $^1$H NMR (500 MHz, DMSO-d$_6$) δ 0.93 (dd, 3H, J=6.0, 3.5 Hz), 1.21-1.28 (m, 1H), 1.32-1.40 (m, 1H), 1.49-1.60 (m, 6H), 1.75 (s, 1H), 2.49-2.66 (m, 5H), 3.11-3.19 (m, 2H), 4.44-4.48 (m, 1H), 5.17 (br s, 1H), 6.59-6.72 (m, 6H), 7.06-7.11 (m, 5H), 9.09 (br s, 1H); m/z (ESI) 583 [C$_{29}$H$_{39}$ClN$_8$O$_3$+H]$^+$.

Example 21

Synthesis of 3,5-diamino-6-chloro-N—[N-(4-{4-[(R)-4-((1R,2S)-1-hydroxy-1-phenylpropan-2-ylamino)pentyl]phenyl}butyl)carbamimidoyl]pyrazine-2-carboxamide (ALB 116995) (Scheme 6) and 3,5-diamino-6-chloro-N—[N-(4-{4-[(S)-4-((1R,2S)-1-hydroxy-1-phenylpropan-2-ylamino)pentyl]phenyl}butyl)carbamimidoyl]pyrazine-2-carboxamide (147a) (Scheme 12)

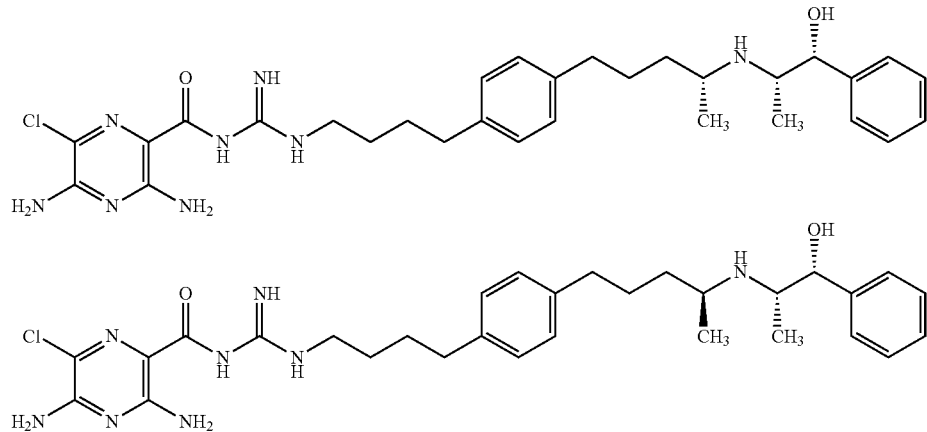

Benzyl 4-{4-[(R)-4-((1R,2S)-1-hydroxy-1-phenylpropan-2-ylamino)pentyl]phenyl}-butylcarbamate (145a) and Benzyl 4-{4-[(R)-4-((1R,2S)-1-hydroxy-1-phenylpropan-2-ylamino)pentyl]-phenyl}butylcarbamate (145b)

A solution of commercially available amino alcohol salt 144 (0.22 g, 1.42 mmol), ketone 140 (0.50 g, 1.36 mmol) and acetic acid (0.08 mL) in methanol (8 mL) were stirred at ambient temperature for 1.5 h. Sodium cyanoborohydride (0.13 g, 2.06 mmol) was then added and the reaction stirred for an additional 14 h. The reaction mixture was then filtered and the filtrate concentrated. Purification by column chromatography (silica, dichloromethane, then 10:90 (10% concentrated ammonium hydroxide/methanol)/dichloromethane) gave the butyl carbamate 145a (0.19 g, 35% yield) as a clear colorless oil: $^1$H NMR (500 MHz, CDCl$_3$) δ 1.01 (d, 3H), 1.32-1.37 (m, 3H), 1.48-1.74 (m, 9H), 2.52-2.62 (m, 4H), 3.11-3.30 (m, 4H), 4.75 (br s, 1H), 5.08 (m, 2H), 7.08 (m, 4H), 7.28-7.37 (m, 10H); m/z (ESI) 503 [C$_{32}$H$_{42}$N$_2$O$_3$+H]$^+$ and 145b (187 mg, 36%) as a clear colorless oil: $^1$H NMR (500 MHz, CDCl$_3$) δ 0.87-0.94 (m, 3H), 1.21-1.27 (m, 3H), 1.48-1.74 (m, 9H), 2.52-2.62 (m, 4H), 2.99 (br s, 1H), 3.11-3.30 (m, 3H), 4.73 (br s, 1H), 4.85-4.95 (m, 1H), 5.08 (m, 2H), 7.08 (m, 4H), 7.28-7.37 (m, 10H); m/z (ESI) 503 [C$_{32}$H$_{42}$N$_2$O$_3$+H]$^+$

(1R,2S)-2-{(R)-5-[4-(4-Aminobutyl)phenyl]pentan-2-ylamino}-1-phenylpropan-1-ol (46a) and (1R,2S)-2-{(S)-5-[4-(4-Aminobutyl)phenyl]pentan-2-ylamino}-1-phenylpropan-1-ol (146b)

A mixture of butylcarbamate 145a (0.19 g, 0.37 mmol), palladium dihydroxide (0.15 g, 10% Pd(OH)$_2$ on carbon, 50% wet) and ethanol (6 mL) was stirred at rt for 66 h under atmospheric hydrogen pressure. The catalyst was removed by filtration through diatomaceous earth and the filtrate was concentrated by rotary evaporation give the desired amine 146a (0.11 g, 77% yield) as a brown oil: $^1$H NMR (500 MHz, CD$_3$OD) δ 0.89-0.94 (m, 3H), 1.00-1.09 (m, 3H), 1.32-1.72 (m, 8H), 2.52-2.92 (m, 7H), 4.75 (br s, 1H), 7.08 (m, 4H), 7.28-7.37 (m, 5H). Following the same procedure, using butylcarbamate 145b (0.19 g, 0.37 mmol), palladium dihydroxide (150 mg, 10% Pd(OH)$_2$ on carbon, 50% wet) and ethanol (6 mL), amine 146b (0.13 g, 99% yield) was obtained as a brown oil: $^1$H NMR (500 MHz, CD$_3$OD) δ 0.87-0.96 (m, 3H), 1.01-1.09 (m, 3H), 1.32-1.72 (m, 8H), 2.52-2.92 (m, 7H), 4.75 (br s, 1H), 7.08 (m, 4H), 7.28-7.37 (m, 5H).

3,5-Diamino-6-chloro-N—[N-(4-{4-[(R)-4-((1R,2S)-1-hydroxy-1-phenylpropan-2-ylamino)pentyl]phenyl}butyl)carbamimidoyl]pyrazine-2-carboxamide (147a) and 3,5-Diamino-6-chloro-N—[N-(4-{4-[(S)-4-((1R,2S)-1-hydroxy-1-phenylpropan-2-ylamino)pentyl]phenyl}butyl)carbamimidoyl]pyrazine-2-carboxamide (147b)

Diisopropylethylamine (0.08 mL, 0.46 mmol) was added to a mixture of amino alcohol 146a (0.11 g, 0.28 mmol) and 1-(3,5-diamino-6-chloropyrazine-2-carbonyl)-2-methylisothiourea hydriodide (5) (0.11 g, 0.28 mmol) in absolute ethanol (3 mL). The mixture was stirred at 75° C. (oil bath) for 5.5 h. After this time the mixture was cooled to rt and the solvent was removed by rotary evaporation. The residue purified by column chromatography (silica gel, a gradient of 5:95 to 10:90 methanol/dichloromethane, followed by 10:90 (10% concentrated aqueous ammonium hydroxide/methanol)/dichloromethane. Further purification by preparative TLC (silica, 10:90 (10% concentrated aqueous ammonium hydroxide/methanol)/dichloromethane) afforded carboxamide derivative 147a (0.04 g, yield) as a yellow solid: mp 60-64° C.; $^1$H NMR (500 MHz, DMSO-d$_6$) δ 0.78 (m, 3H), 0.91-1.03 (m, 3H), 1.22-1.63 (m, 9H), 2.59-2.66 (m, 2H), 2.71-2.92 (br s, 2H), 3.11-3.19 (m, 2H), 3.28-3.30 (m, 1H), 4.58 (br s, 1H), 6.68 (br s, 2H), 7.06-7.11 (m, 4H), 7.20-7.32 (m, 5H), 9.09 (br s, 1H); m/Z (EST) 583 [C$_{30}$H$_{41}$ClN$_8$O$_2$+H]$^+$. Following the same procedure, using amine 146b (0.13 g, 0.36 mmol), thiourea 5 (0.14 g, 0.37 mmol), and diisopropylethylamine (0.10 mL, 0.57 mmol) in ethanol (4 mL), 147b (0.03 g, 13% yield) was obtained as a yellow solid: mp 58-62° C.; $^1$H NMR (500 MHz, DMSO-d$_6$) δ 0.81 (br s, 3H), 0.99-

1.18 (m, 3H), 1.29-1.63 (m, 8H), 2.59-2.66 (m, 3H), 2.81-3.19 (m, 4H), 4.70 (br s, 1H), 6.50-7.11 (m, 7H), 7.20-7.32 (m, 5H), 9.09 (br s, 1H); m/z (ESI) 583 $[C_{30}H_{41}ClN_8O_2+H]^+$.

Example 22

Synthesis of (R)-3,5-diamino-N—(N-4-(4-(2-(3-(2-(4-(benzyloxy)-3-formamidophenyl)-2-hydroxyethylamino)butylamino)-2-oxoethoxy)phenyl)butyl)carbamimidoyl)-6-chloropyrazine-2-carboxamide di-L-lactate 160 (Scheme 13)

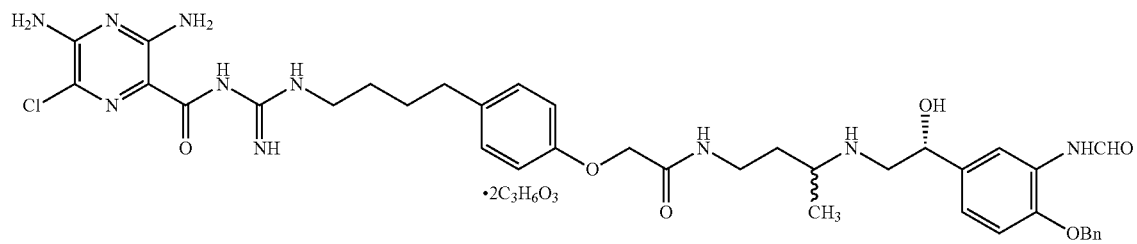

Benzyl 3-hydroxybutylcarbamate (49)

A solution of 4-aminobutan-2-ol (3.00 g, 33.65 mmol) and diiso-propylethylamine (DIPEA, 8.79 mL, 50.48 mmol) in dichloromethane (anhydrous, 100 mL) was cooled in an ice/water bath for 15 min. To this solution was added CbzCl (5.74 mL, diluted with 20 mL anhydrous dichloromethane) dropwise over 30 min. The ice bath was removed, and the resulting reaction mixture was stirred at room temperature for additional 3 h. After this time the mixture was concentrated and the resulting residue was chromatographed (silica gel, a gradient of 1:99 to 3:97 methanol/dichloromethane), affording 149 (8.91 g, quant yield) as a light brown, viscous oil: $^1$H NMR (500 MHz, CDCl$_3$) δ 1.20 (d, 3H), 1.58 (m, 2H), 3.22 (m, 2H), 3.90 (m, 1H), 5.10 (s, 2H), 5.28 (br s, 1H), 7.34 (m, 5H); m/z (ESI) 224 [M+H]$^+$.

Benzyl 3-(tert-butyldimethylsilyloxy)butylcarbamate (150)

A solution of 149 (4.49 g, 20.13 mmol) and imidazole (2.05 g, 30.20 mmol) in dichloromethane (anhydrous, 60 mL) was cooled in an ice/water bath. To the solution was added TBDMSCl (3.34 g, 22.14 mmol) in one portion, and the mixture was stirred overnight while allowing the temperature to naturally rise up to room temperature. After this time the solid precipitate was removed by filtration. The filtrate was loaded on a short silica gel pad and eluted with 12:88 ethyl acetate/hexanes, affording 7.10 g (quant yield) of the desired product 150 as a colorless liquid: $^1$H NMR (500 MHz, CDCl$_3$) δ 0.49 (s, 3H), 0.51 (s, 3H), 0.85 (s, 9H), 1.09 (d, 3H), 1.69 (m, 2H), 3.20 (m, 2H), 3.88 (m, 1H), 4.67 (m, 1H), 5.0 (s, 2H), 5.15 (br s, 1H), 7.28 (m, 5H); m/z (ESI) 338 [M+H]$^+$.

3-tert-Butyldimethylsilyloxy)butan-1-amine (151)

A suspension of compound 150 (7.10 g, 21.06 mmol) dissolved in ethanol (50 mL) and palladium catalyst (1.50 g, 10% Pd on carbon, 50% wet) was stirred under a hydrogen atmosphere for 5 h. The catalyst was removed by filtration and washed with ethanol (3×15 mL). The filtrate and washings were combined and concentrated under vacuum to complete dryness, affording 151 (3.60 g, 84% yield) as a colorless, viscous oil: $^1$H NMR (500 MHz, CD$_3$OD) δ 0.48 (s, 3H), 0.53 (s, 3H), 0.90 (s, 9H), 1.10 (s, 3H), 1.55 (m, 2H), 2.68 (m, 2H), 3.88 (m, 1H); m/z (ESI) 204 [M+H]$^+$.

Benzyl-4-(4-(2-(3-(tert-butyldimethylsilyloxy)butylamino)-2-oxoethyoxy)phenyl)-butylcarbamate (153)

To a suspension containing 2-(4-(4-(benzyloxycarbonylamino)butyl)phenoxy)acetic acid 152 (5.07 g, 14.18 mmol) and carbonyl diimidazole (CDI, 2.87 g, 17.73 mmol) in THF hydrazine (anhydrous, 50 mL) was added compound 151 (3.61 g, 17.73 mmol, dissolved in 5 mL anhydrous THF), and the mixture was stirred at room temperature overnight. The solid was removed by filtration and washed with THF (3×20 mL). The filtrate and washings were combined and concentrated. The residue was subjected to column chromatography (a gradient of 0:100 to 50:50 ethyl acetate/hexanes), affording the desired product 153 (4.33 g, 56% yield) as a colorless, viscous oil: $^1$H NMR (500 MHz, CDCl$_3$) δ 0.48 (s, 3H), 0.53 (s, 3H), 0.90 (s, 9H), 1.18 (s, 3H), 1.53-1.75 (m, 6H), 2.62 (m, 2H), 3.24 (m, 2H), 3.44 (m, 2H), 3.93 (m, 1H), 4.18 (br s, 1H), 4.46 (s, 2H), 4.78 (br s, 1H), 5.12 (s, 2H), 6.83 (d, 2H), 7.08 (d, 2H), 7.36 (m, 5H); m/z (ESI) 534 [M+H]$^+$.

Benzyl 4-(4-(2-(3-(hydroxybutylamino)-2-oxoethoxy)phenyl)butylcarbamate (154)

A solution of compound 153 (4.33 g, 7.97 mmol) and TBAF (1 M solution in THF, 24 mL) in THF (20 mL) was stirred at room temperature for 72 h, and then concentrated. The residue was subjected to column chromatography (a gradient of 50:50 to 10:90 ethyl acetate/hexanes), affording 2.32 g (67% yield) of the desired product 54: $^1$H NMR (300 MHz, CDCl$_3$) δ 1.22 (s, 3H), 1.33 (m, 1H), 1.43 (m, 1H), 1.53-1.77 (m, 4H), 2.41 (m, 2H), 2.62 (t, 2H), 2.92 (br s, 1H), 3.24 (m, 2H), 3.78 (m, 2H), 4.40 (s, 2H), 4.75 (br s, 1H), 5.12 (s, 2H), 6.81 (d, 2H), 7.12 (d, 2H), 7.36 (m, 5H); m/z (ESI) 429 [M+H]$^+$.

Benzyl 4-(4-(2-oxo-2-(3-(oxobutylamino)ethyoxy)phenyl)butylcarbamate (155)

A mixture of compound 154 (1.21 g, 2.82 mmol) and PCC (1.83 g, 8.46 mmol) in dichloromethane (20 mL) was stirred at room temperature overnight. After this time the mixture was subjected to column chromatography (a gradient of 50:50 to 80:20 ethyl acetate/hexanes) to afford the desired product 55 (0.85 g, 71% yield) as an off-white solid: $^1$H NMR (300 MHz, CDCl$_3$) δ 1.53-1.70 (m, 4H), 2.12 (s, 3H), 2.57 (t, 2H), 2.72 (t, 2H), 3.22 (m, 2H), 3.64 (m, 2H), 4.40 (s, 2H), 4.75 (br s, 5.12 (s, 2H), 6.81 (d, 2H), 7.12 (d, 2H), 7.36 (m, 5H); m/z (ESI) 427 [M+H]$^+$.

(R)-Benzyl 4-(4-(2-(3-(2-(4-(benzyloxy)-3-formamidophenyl)-2-hydroxyethylamino)butylamino)-2-oxoethoxy)phenyl)butylcarbamate (157)

A solution containing compound 55 (0.86 g, 2.01 mmol) and (R)—N-(5-(2-amino-1-hydroxyethyl)-2-benzyloxy)phenyl)formamide 56 (0.41 g, 2.12 mmol) in methanol (anhydrous, 10 mL) was stirred at room temperature for 3 h. To the solution was then added NaCNBH$_3$ (0.38 g, 6.05 mmol) in one portion, and the mixture was continuously stirred at room temperature overnight. After this time the mixture was concentrated and the residue was subjected to chromatography (a gradient of 0:100 to 9:91 methanol/dichloromethane) to afford the desired product 57 (1.01 g, 83% yield): $^1$H NMR (300 MHz, CD$_3$OD) δ 1.33 (m, 3H), 1.47-1.68 (m, 4H), 1.77 (m 1H), 2.02 (m, 1H), 2.54 (m, 2H), 3.02-3.26 (m, 5H), 3.56 (m, 2H), 4.54 (d, 2H), 4.84 (m, 1H), 5.10 (s, 2H), 6.90 (m, 3H), 7.12 (m, 3H), 7.35 (m, 5H), 8.13 (s, 1H), 8.33 (s, 1H); m/z (ESI) 607 [M+H]$^+$.

(R)-2-(4-(4-Aminobutyl)phenoxy)-N-(3-(2-(4-(benzyloxy)-3-formamidophenyl)-2-hydroxyethylamino)butyl)acetamide (158)

A mixture of compound 57 (1.01 g, 1.66 mmol) dissolved in methanol (50 mL) and palladium catalyst (0.30 g, 10% Pd on carbon, 50% wet) was stirred overnight at room temperature under one atmospheric hydrogen pressure. The catalyst was removed by filtration and washed with methanol (3×15 mL). The filtrate and washings were combined and concentrated under vacuum to complete dryness, affording 158 (0.71 g, 91% yield) as an off-white foam: $^1$H NMR (300 MHz, CD$_3$OD) δ 1.14 (m, 3H), 1.50-1.82 (m, 6H), 2.60 (m, 2H), 2.78 (m, 4H), 3.34 (m, 3H), 4.50 (s, 2H), 4.65 (m, 1H), 6.84 (m, 3H), 7.14 (m, 3H), 8.13 (s, 1H), 8.33 (s, 1H); m/z (ESI) 473 [M+H]$^+$.

(R)-3,5-Diamino-N—(N-4-(4-(2-(3-(2-(4-(benzyloxy)-3-formamidophenyl)-2-hydroxyethylamino)butylamino)-2-oxoethoxy)phenyl)butyl)carbamimidoyl)-6-chloropyrazine-2-carboxamide (159)

A suspension of compound 158 (0.65 g, 1.37 mmol), Hunig's base (0.96 mL, 5.50 mmol) and ethanol (5 mL) was heated at 70° C. for 30 min, and then 1-(3,5-diamino-6-chloropyrazine-2-carbonyl)-2-methylisothiourea hydriodide (0.59 g, 1.51 mmol) was added. The resulting solution was continuously stirred at that temperature for an additional 3 h before it was cooled to room temperature. The un-dissolved solid was removed by filtration. The filtrate was concentrated. The resulting residue was subjected to column chromatography (a gradient of 0:100 to 16:84 (10% concentrated ammonium hydroxide in methanol)/dichloromethane) to afford 159 (0.103 g, 27% yield) as a yellow solid: $^1$H NMR (500 MHz, CD$_3$OD) δ 1.12 (m, 3H), 1.58 (m, 2H), 1.68 (m, 4H), 2.58 (m, 2H), 2.75 (m, 3H), 3.28 (m, 4H), 4.48 (s, 2H), 4.67 (m, 1H), 6.87 (d, 1H), 6.93 (d, 2H), 7.01 (d, 1H), 7.18 (d, 2H), 8.06 (s, 1H), 8.33 (s, 1H); m/z (ESI) 605 [M+H]$^+$.

(R)-3,5-Diamino-N—(N-4-(4-(2-(3-(2-(4-(benzyloxy)-3-formamidophenyl)-2-hydroxyethylamine)butylamino)-2-oxoethoxy)phenyl)butyl)carbamimidoyl)-6-chloropyrazine-2-carboxamide di-L-lactate [160]

L-lactic acid (0.027 g, 0.30 mmol) was added to a suspension of compound 159 (0.103 g, 0.15 mmol) in ethanol (10 mL), and the mixture was stirred at room temperature for 2 h. The solution was then concentrated under vacuum and completely dried to afford 160 (0.129 g, quant yield) as a light yellow solid: mp 82-86° C.; [α]$_D^{25}$ −3.01°; $^1$H NMR (500 MHz, DMSO-d$_6$) δ 1.12 (m, 3H), 1.22 (d, 6H), 1.56 (m, 5H), 1.74 (m, 1H), 2.80 (m, 2H), 2.94 (m, 1H), 3.20 (m, 4H), 3.98 (q, 2H), 4.40 (s, 2H), 4.65 (m, 1H), 6.88 (m, 4H), 7.14 (d, 2H), 8.10 (s, 1H), 8.30 (s, 1H); m/z (ESI) 685 [M+H]$^+$.

Example 23

Synthesis of N—(N-(4-(4-((S)-4-((R)-2-(3-acetamido-4-hydroxyphenyl)-2-hydroxyethylamino)pentyl)phenyl)butyl)carbamimidoyl)-3,5-diamino-6-chloropyrazine-2-carboxamide di-L-lactate [175]] (Scheme 14)

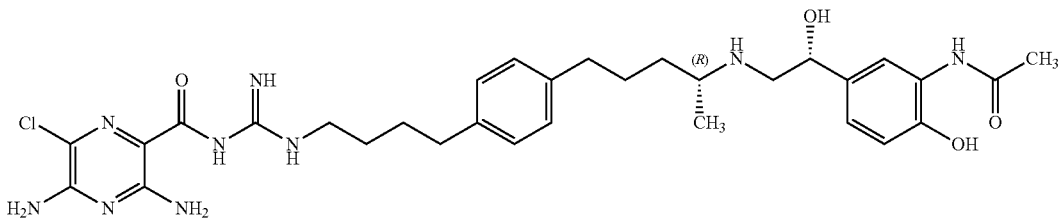

175

(R)—N-5-(2-Amino-1-hydroxyethyl)-2-(benzyloxy)phenyl)acetamide (171)

A suspension of compound 170 (300 mg, 0.93 mmol) and palladium catalyst (50 mg, 10% Pd on charcoal, 50% wet) in a mixed solvent of EtOH and EtOAc (6 mL, 1/1) was subject to hydrogenation for 3.5 h under 50 psi hydrogen pressure and rt. The catalyst was filtered through Celite and washed with EtOH (3×5 mL). The combined filtrate and washings were concentrated and further dried under high vacuum to afford the desired product 171 (124 mg, 54% yield) as a light yellow solid which was used directly without further purification. $^1$H NMR (500 MHz, CD$_3$OD) δ 2.16 (s, 3H), 2.81 (d, 2H), 4.55 (m, 1H), 6.82 (m, 1H), 6.99 (m, 1H), 7.64 (s, 1H); m/z (ESI) 211 [M+H]$^+$.

Benzyl 4-(4-(4-(R)-2-(3-acetamido-4-benzyloxy)phenyl)-2-hydroxyethylamino)-pentyl)phenyl)butylcarbamate (172)

A solution of compounds 171 (124 mg, 0.59 mmol) and 40 (217 mg, 0.59 mmol) in methanol (anhydrous, 5 mL) was stirred at room temperature for 2.5 h. To this solution was then added NaCNBH$_3$ (100 mg, 1.59 mmol) in one portion, and the mixture was continuously stirred at room temperature overnight. After this time, the mixture was concentrated and the residue was subject to chromatography (a gradient of 5:95 to 10:90 methanol/dichloromethane) to afford the desired product 172 (183 mg, 55% yield) as a light yellow solid: $^1$H NMR (500 MHz, CDCl$_3$) δ 1.21 (m, 3H), 1.50-1.65 (m, 8H), 2.16 (s, 3H), 2.54 (m, 4H), 2.72-3.12 (m, 3H), 3.18 (m, 2H), 3.58 (m, 1H), 4.76 (m, 1H), 4.80 (br, s, 1H), 5.07 (m, 2H), 6.88 (m, 1H), 6.94 (m, 1H), 7.04 (s, 4H), 7.34 (br s, 5H), 8.45 (s, 1H); m/z (ESI) 562 [M+H]$^+$.

N-(5-((1R)-2-(5-(4-(4-Aminobutyl)phenyl)pentan-2-ylamino)-1-hydroxyethyl)-2-benzyloxyphenyl)acetamide (173)

A mixture of compound 172 (180 mg, 0.32 mmol) and palladium catalyst (100 mg, 10% Pd on carbon, 50% wet) in ethanol (5 mL) underwent hydrogenation overnight under room temperature and one H$_2$ pressure. The catalyst was vacuum filtered and washed with ethanol (3×5 mL). The filtrate and the washings were combined and concentrated to afford the desired product 173 (119 mg, 87% yield) as a colorless, glass solid which was used directly without further purification: $^1$H NMR (500 MHz, CD$_3$OD) δ 1.13 (m, 3H), 1.35-1.76 (m, 8H), 2.17 (s, 3H), 2.60 (m, 4H), 2.83 (m, 5H), 4.65 (m, 1H), 6.83 (m, 1H), 7.03 (m, 1H), 7.10 (m, 4H), 7.70 (s, 1H); m/z (EST) 428 [M+H]$^+$.

N—N-(4-(4-((S)-4-((R)-2-(3-Acetamido-4-hydroxyphenyl)-2-hydroxyethylamino)-pentyl)phenyl)butyl)carbamimidoyl)-3,5-diamino-6-chloropyrazine-2-carboxamide (174)

A solution of compound 173 (115 mg, 0.27 mmol), Hunig's base (0.07 mL, 0.40 mmol) and ethanol (3 mL) was heated at 75° C. for 30 min. To the solution was then added 1-(3,5-diamino-6-chloropyrazine-2-carbony)-2-methylisothiourea hydriodide (105 mg, 0.27 mmol). The resulting solution was continuously stirred at that temperature for an additional 6 h before it was cooled to room temperature. The solvent was removed by evaporation. The resulting residue was subject to column chromatography (silica, a gradient of 1 to 15 (10% ammonium hydroxide in methanol)/dichloromethane) to afford 174 (51 mg, 30% yield) as a yellow solid: $[\alpha]_D^{25}$ −9.1° (c 0.25, methanol); $^1$H NMR (500 MHz, CD$_3$OD) δ 1.05 (m, 3H), 1.32 (m, 2H), 1.50-1.80 (m, 6H), 2.17 (s, 3H), 2.53 (m, 4H), 2.66-2.86 (m, 3H), 3.25 (m, 2H), 4.66 (m, 1H), 6.83 (m, 1H), 6.98 (m, 1H), 7.10 (m, 4H), 7.72 (s, 1H); m/z (ESI) 640 [M+H]$^+$.

N—(N-(4-(4-((S)-4-((R)-2-(3-Acetamido-4-hydroxyphenyl)-2-hydroxyethylamino)-pentyl)phenyl)butyl)carbamimidoyl)-3,5-diamino-6-chloropyrazine-2-carboxamide di-L-lactate [175]

Compound 175 (54 mg, quant yield), a yellow solid, was prepared from 174 in a similar method to 168a: mp 46-50° C. (decomposed); $^1$H NMR (500 MHz, DMSO-d$_6$) δ 1.05 (m, 3H), 1.17 (s, 6H), 1.32 (m, 2H), 1.50-1.80 (m, 6H), 2.08 (s, 3H), 2.53 (m, 4H), 2.60-2.82 (m, 2H), 2.94 (m, 1H), 3.20 (m, 2H), 3.43 (m, 2H), 3.87 (m, 2H), 4.63 (m, 1H), 6.68 (br s, 1H), 6.81 (m, 1H), 6.92 (m, 1H), 7.10 (m, 4H), 7.28 (br s, 1H), 7.71 (s, 1H), 9.34 (s, 1H); m/z (ESI) 640 [M+H]$^+$.

Methods
Pharmacological Effects and Mechanism of Action of the Drug in Animals

The effect of compounds for enhancing mucociliary clearance (MCC) can be measured using an in vivo model described by Sabater et al., Journal of Applied Physiology, 1999, 87(6) pp. 2191-2196, incorporated herein by reference.

Animal Preparation: Adult ewes up to 75 Kg were placed in a restraint and positioned upright using a specialized body harness. The heads of the animals were immobilized, and local anesthesia of the nasal passage was provided (2% lidocaine) prior to nasal intubation (7.5 mm-I.D. endotracheal tube (ETT) (Mallinckrodt Medical, St. Louis, Mo.). The cuff of the ETT was placed just below the vocal cords. After intubation, the animals were allowed to equilibrate for approximately 20 min before MCC measurements began.

Sheep MCC in vivo Measurement: Aerosols of sulfur colloid radiolabeled with technetium ($^{99m}$Tc—SC 3.1 mg/mL, ~10-15 mCi) were generated by a Raindrop Nebulizer (Nellcor Puritan Bennett, Pleasanton, Calif.) which produces a median aerodynamic droplet diameter of 3.6 μm. The nebulizer was connected to a dosimeter system consisting of a solenoid valve and a source of compressed air (20 psi). The output of the nebulizer was directed into a T piece, with one end attached to a respirator (Harvard apparatus, South Natick, Mass.). The system was activated for 1 second at the onset of the respirator's inspiratory cycle. The tidal volume was set at 300 mL, with an inspiratory-to-expiratory ratio of 1:1, and a rate of 20 breaths/min, to maximize central airway deposition. The sheep breathed the $^{99m}$Tc—SC aerosol for up to 5 min. Following tracer deposition, a gamma camera was used to measure the clearance of $^{99m}$Tc—SC from the airways. The camera was positioned above the animal's back with the sheep in its natural upright position in the harness. The field of the image was perpendicular to the animal's spinal cord. External radiolabeled markers were placed on the sheep to facilitate proper alignment of the gamma camera. A region of interest was traced over the image corresponding to the right lung of the sheep and counts were recorded. The counts were corrected for decay and expressed as a percentage of radioactivity present in the baseline image. The left lung was excluded from the analysis because the outline of the lung was superimposed over the stomach and counts could be affected by swallowed $^{99m}$Tc—SC-labeled mucus. Alt deposition images were stored on a computer interfaced to the gamma camera. The protocol included a baseline deposition image obtained immediately post radio-aerosol administration. After acquisition of baseline images, either 4 mL of H$_2$O (vehicle), formoterol (3 mM), or novel chemical entity (3 mM) were aerosolized using the Pari LC JetPlus nebulizer to free-breathing sheep using two separate protocols. Protocol 1, acquired data immediately after dosing (time 0 to 1 hour), and indicated the immediate physiological response 'short-term efficacy' protocol 2, acquired data 4 hours post dosing indicated compound durability and 'long-term efficacy'. The nebulizer had a flow rate of 8 L/min and the time to deliver the solution was 10-12 min. On the completion of compound administration, the animal was immediately extubated to prevent false elevations in counts due to aspiration of excess $^{99m}$Tc—SC-labeled mucus from the ETT. Serial measurements of $^{99m}$Tc—SC retained in the lung were obtained over a 1 hour period at 5 min intervals. A washout period of at least 7 days (half life of $^{99m}$TC=6 h) separated studies with the different agents.

Statistical Analysis: Data from the in vivo sheep MCC assays were analyzed using a two way ANOVA with repeated measures, followed by slope analysis of the linear regression of the retention vs time plot using an ANOCOVA to compare slopes, and if needed a multiple comparison test (Newman-Keuls). The percent activity retained (post 4 hours was calculated by dividing the slope value from protocol 2 by the slope value obtained in protocol 1 and multiplying by 100%.

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 µm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal=s back with the sheep in a natural upright position supported in a cart so that the field of image was perpendicular to the animal=s spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA to assess overall effects), followed by a paired t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Obviously, numerous modifications and variations of the present invention are possible in light of the above teachings. It is therefore to be understood that within the scope of the appended claims, the invention may be practiced otherwise than as specifically described herein.

The invention claimed is:
1. A compound which is selected from the group consisting of:

121
-continued
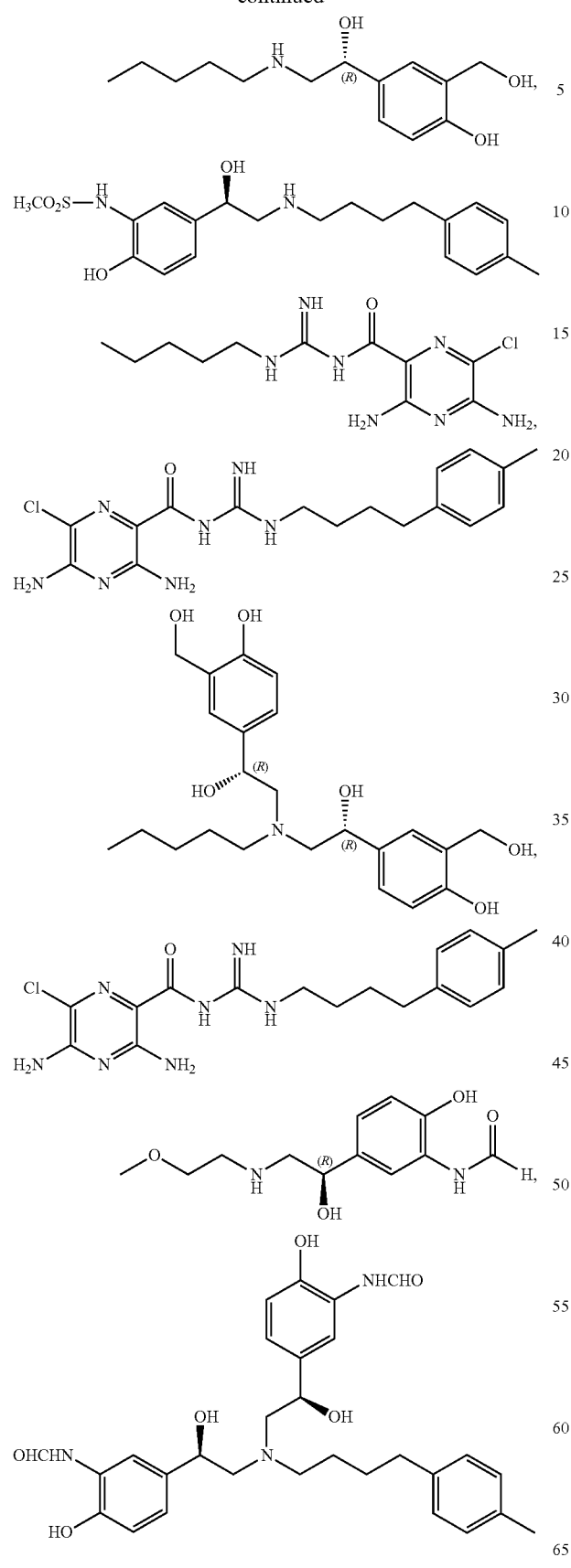
122
-continued
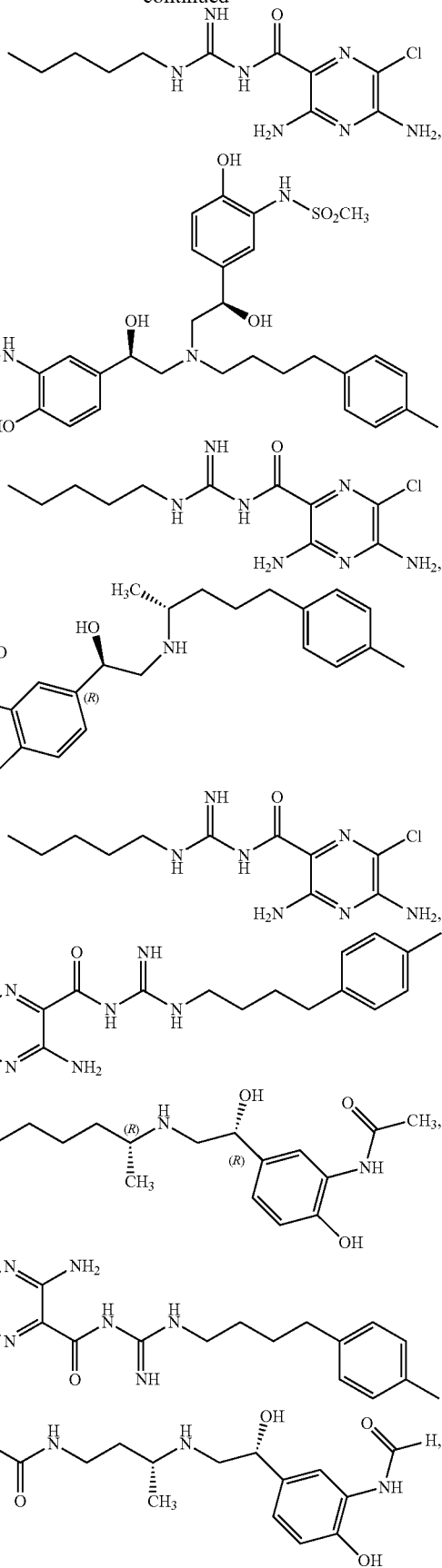

-continued
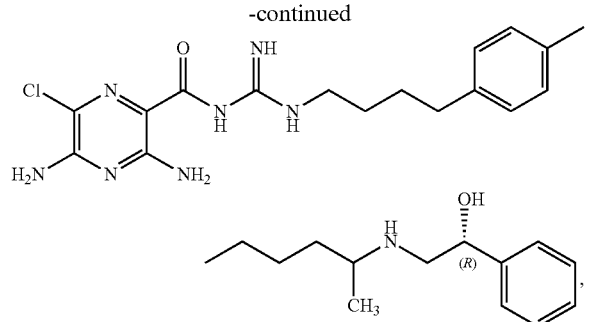
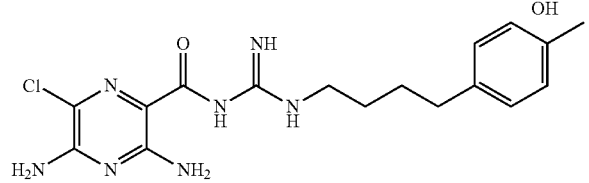
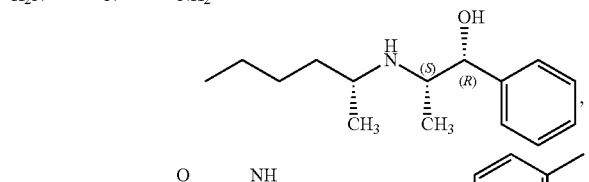
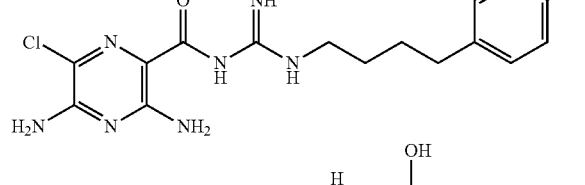
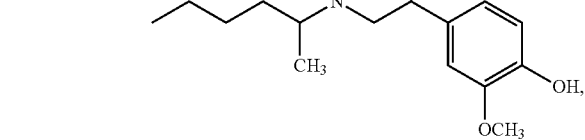
-continued
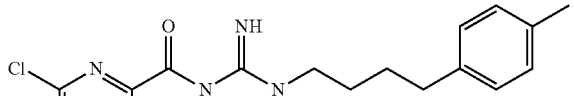
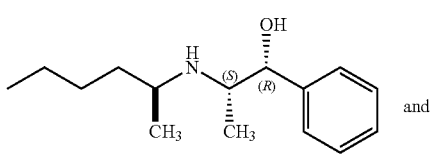 and
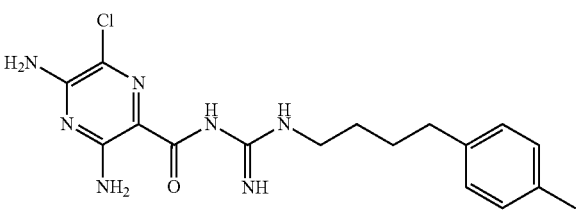
2. The compound of claim 1, which is represented by the formula:
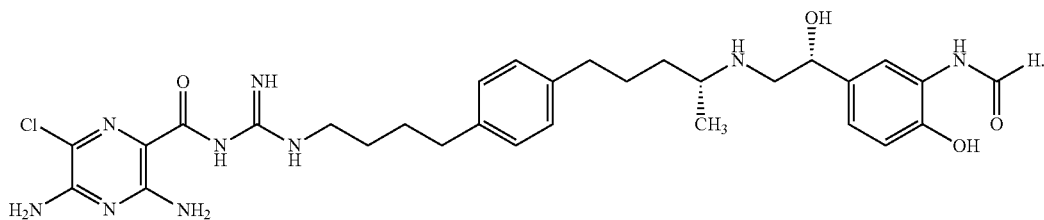
3. A pharmaceutical composition comprising the compound of claim 1 and a pharmaceutically acceptable carrier.
* * * * *